US008853496B2

(12) United States Patent
Poree et al.

(10) Patent No.: US 8,853,496 B2
(45) Date of Patent: Oct. 7, 2014

(54) PLANTS TOLERANT TO HPPD INHIBITOR HERBICIDES

(75) Inventors: Fabien Poree, Frankfurt (DE); Bernd Laber, Idstein (DE); Nathalie Knittel-Ottleben, Kriftel (DE); Gudrun Lange, Kelkheim (DE); Arno Schulz, Eppstein (DE); Ruediger Hain, Frankfurt (DE)

(73) Assignee: Bayer CropScience AG, Monheim (DE)

( * ) Notice: Subject to any disclaimer, the term of this patent is extended or adjusted under 35 U.S.C. 154(b) by 333 days.

(21) Appl. No.: 12/977,211

(22) Filed: Dec. 23, 2010

(65) Prior Publication Data

US 2011/0191897 A1    Aug. 4, 2011

Related U.S. Application Data

(60) Provisional application No. 61/290,575, filed on Dec. 29, 2009, provisional application No. 61/412,087, filed on Nov. 10, 2010.

(30) Foreign Application Priority Data

Dec. 23, 2009  (EP) ..................................... 09015985
Nov. 10, 2010  (EP) ..................................... 10190657

(51) Int. Cl.
*C12N 15/82* (2006.01)
*C12N 9/02* (2006.01)

(52) U.S. Cl.
CPC .......... *C12N 15/8274* (2013.01); *C12N 9/0069* (2013.01)
USPC .......................................... 800/300; 800/298

(58) Field of Classification Search
USPC ....................................................... 800/300
See application file for complete search history.

(56) References Cited

U.S. PATENT DOCUMENTS

| | | | | |
|---|---|---|---|---|
| 6,245,968 B1 * | 6/2001 | Boudec et al. | ................. | 800/278 |
| 6,268,549 B1 * | 7/2001 | Sailland et al. | ................. | 800/295 |
| 7,250,561 B1 * | 7/2007 | Pallett et al. | ................. | 800/300 |
| 2005/0257283 A1 * | 11/2005 | Matringe et al. | ............... | 800/278 |
| 2011/0197307 A1 | 8/2011 | Poree et al. | | |
| 2011/0197308 A1 | 8/2011 | Poree et al. | | |
| 2011/0197309 A1 | 8/2011 | Poree et al. | | |
| 2011/0197310 A1 | 8/2011 | Poree et al. | | |

FOREIGN PATENT DOCUMENTS

| | | |
|---|---|---|
| WO | WO 96/38567 A2 | 12/1996 |
| WO | WO 2009/144079 A1 | 12/2009 |

OTHER PUBLICATIONS

Friedberg I., Automated Protein Function Prediction—the Genomic Challenge, Brief. Bioinformatics (2006) 7:225-242.*
Hausman et al, Resistance to HPPD-inhibiting Herbicides in a Population of Waterhemp (*Amaranthus tuberculatus*) From Illinois, United States, Pest Mgmt. Sci. (2010) 67:258-261.*
Tanaka et al, Cdk1 and Cks Gene Homologs are Transcriptionally Activated During Induction of Conjugating Pairs in Mating-Type II Cells of the Ciliate *Blepharisma japonicum*, Gensei Dobutsugaku Zasshi (2007) 40:131-138, Database Accession No. AB325671, Nov. 2, 2007.*
Campbell et al, Codon usage in higher plants, green algae, and cyanobacteria, Plant Physiol. (1990) 92:1-11.*
EMBL Database, Accession No. AB325671, Tanaka, Y., et al., 2 pages (Nov. 2, 2007).
International Search Report for Application No. PCT/EP2010/070567, European Patent Office, Rijswijk, The Netherlands, mailed on Mar. 22, 2011.

\* cited by examiner

*Primary Examiner* — David H Kruse
*Assistant Examiner* — Mykola Kovalenko
(74) *Attorney, Agent, or Firm* — Sterne, Kessler, Goldstein & Fox P.L.L.C.

(57) ABSTRACT

The present invention relates to nucleic acid sequences encoding a hydroxyphenylpyruvate dioxygenase (EC 1.13.11.27, abbreviated herein as HPPD) obtained from protists belonging to the family Blepharismidae, as well as the proteins encoded thereby, and to a chimeric gene which comprises such nucleic acid sequence, and to the use of such nucleic acid sequences, proteins or chimeric genes for obtaining plants which are tolerant to HPPD inhibitor herbicides.

11 Claims, 2 Drawing Sheets

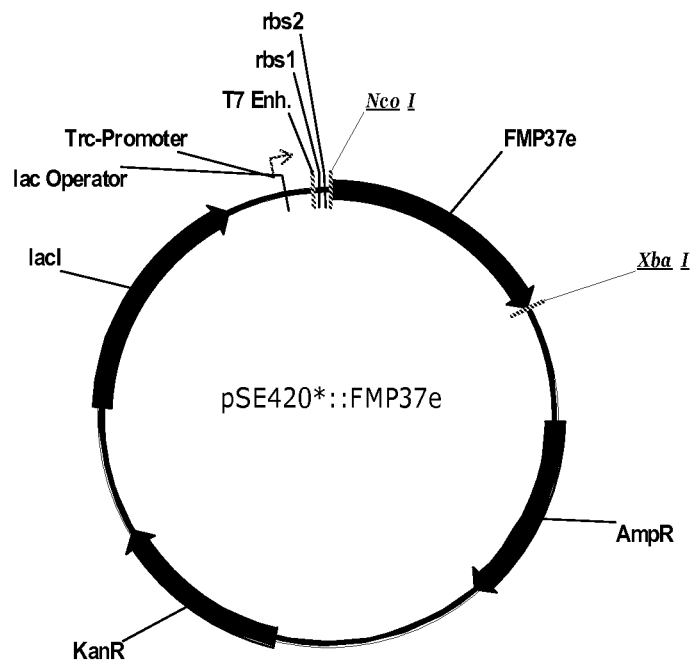
Figure1: map of the plasmid pSE420-FMP37e
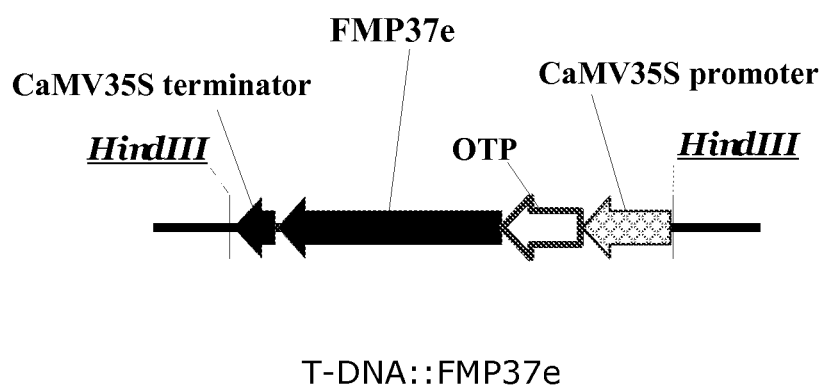
Figure 2: map of the T-DNA inserted into the tobacco plants.

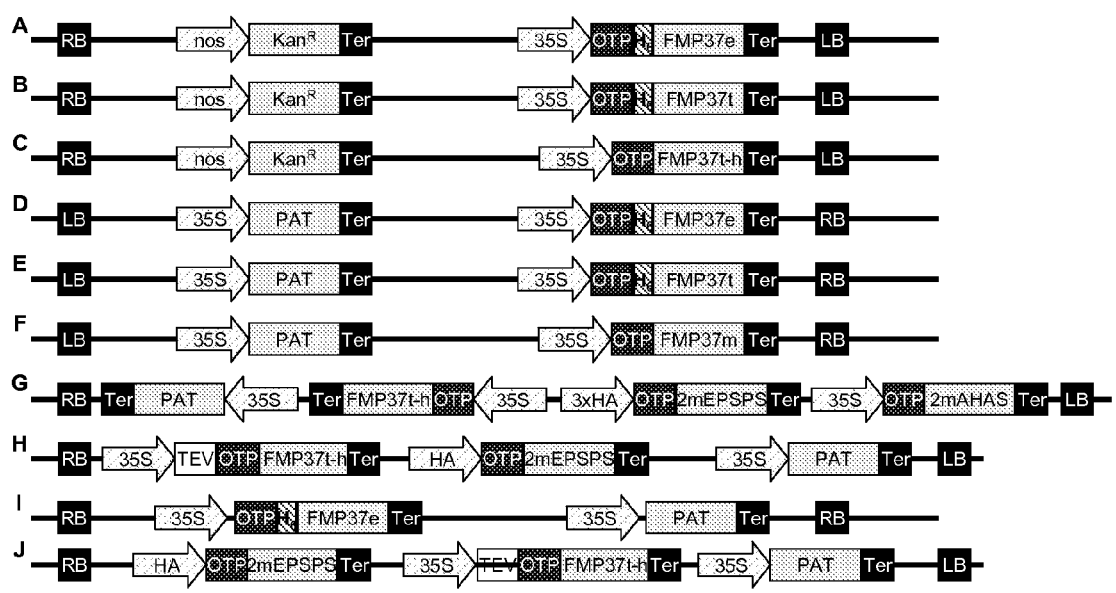
Figure 3: Map of the different T-DNA inserted into plants.

PLANTS TOLERANT TO HPPD INHIBITOR HERBICIDES

REFERENCE TO SEQUENCE LISTING SUBMITTED ELECTRONICALLY VIA EFS-WEB

The content of the electronically submitted sequence listing (name: 2400_3850001_sequencelisting_ascii.txt (59 KB); date of creation: Mar. 4, 2011) submitted in this application is incorporated herein by reference in its entirety.

INTRODUCTION

The present invention relates to nucleic acid sequences encoding a hydroxyphenylpyruvate dioxygenase (EC 1.13.11.27, abbreviated herein as "HPPD") obtained from protists belonging to the family Blepharismidae, as well as the proteins encoded thereby, and to a chimeric gene which comprises such nucleic acid sequence, and to the use of such nucleic acid sequences, proteins or chimeric genes for obtaining plants which are tolerant to HPPD inhibitor herbicides.

BACKGROUND

The HPPDs are enzymes which catalyse the reaction in which para-hydroxyphenylpyruvate (abbreviated herein as HPP), a tyrosine degradation product, is transformed into homogentisate (abbreviated herein as HG), the precursor in plants of tocopherol and plastoquinone (Crouch N. P. et al. (1997) Tetrahedron, 53, 20, 6993-7010, Fritze et al., (2004), Plant Physiology 134:1388-1400). Tocopherol acts as a membrane-associated antioxidant. Plastoquinone, firstly acts as an electron carrier between PSII and the cytochrome b6/f complex and secondly, is a redox cofactor for phytoene desaturase, which is involved in the biosynthesis of carotenoids.

Up to now, more than 700 nucleic acid sequences from various organisms present in NCBI database were annotated as coding for a putative protein having an HPPD domain including the sequence disclosed under the A8R3H6 accession number given in the UniProtKB/TrEMBL database as well as under the BAF91881 accession number given in the NCBI protein database. But for most of those, including the sequence corresponding to the accession number A8R3H6/BAF91881, it has not been proven that the protein would have an HPPD enzymatic activity either in an in vitro assay or an in planta approach, nor that such HPPD protein can confer herbicide tolerance to HPPD inhibitor herbicides when expressed in a plant. Several HPPD proteins and their primary sequences have been described in the state of the art, in particular the HPPD proteins of bacteria such as *Pseudomonas* (Rüetschi et al., Eur. J. Biochem., 205, 459-466, 1992, WO 96/38567), of plants such as *Arabidopsis* (WO 96/38567, Genebank AF047834), carrot (WO 96/38567, Genebank 87257), *Avena sativa* (WO 02/046387), wheat (WO 02/046387), *Brachiaria platyphylla* (WO 02/046387), *Cenchrus echinatus* (WO 02/046387), *Lolium rigidum* (WO 02/046387), *Festuca arundinacea* (WO 02/046387), *Setaria faberi* (WO 02/046387), *Eleusine indica* (WO 02/046387), *Sorghum* (WO 02/046387), *Coccicoides* (Genebank COITRP), of *Coptis japonica* (WO 06/132270), *Chlamydomonas reinhardtii* (ES 2275365), or of mammals such as mouse or pig. The corresponding sequences disclosed in the indicated references are hereby incorporated by reference.

Most plants synthesize tyrosine via arrogenate (Abou-Zeid et al. (1995), Applied Env Microb 41: 1298-1302; Bonner et al., (1995), Plant Cells Physiol. 36, 1013-1022; Byng et al., (1981), Phytochemistry 6: 1289-1292; Connely and Conn (1986), Z. Naturforsch 41c: 69-78; Gaines et al., (1982), Plants 156: 233-240). In these plants, the HPP is derived only from the degradation of tyrosine. On the other hand, in organisms such as the yeast *Saccharomyces cerevisiae* or the bacterium *Escherichia coli*, HPP is a tyrosine precursor, and it is synthesized by the action of an enzyme, prephenate dehydrogenase (hereinafter referred to as PDH), which converts prephenate to HPP (Lingens et al., (1967) European J. Biochem 1: 363-374; Sampathkumar and Morrisson (1982), Bioch Biophys Acta 701: 204-211). In these organisms, the production of HPP is therefore directly connected to the aromatic amino acid biosynthetic pathway (shikimate pathway), and not to the tyrosine degradation pathway.

Inhibition of HPPD leads to uncoupling of photosynthesis, deficiency in accessory light-harvesting pigments and, most importantly, to destruction of chlorophyll by UV-radiation and reactive oxygen species (bleaching) due to the lack of photo protection normally provided by carotenoids (Norris et al. (1995), Plant Cell 7: 2139-2149). Bleaching of photosynthetically active tissues leads to growth inhibition and plant death.

Some molecules which inhibit HPPD, and which bind specifically to the enzyme in order to inhibit transformation of the HPP into homogentisate, have proven to be very effective selective herbicides.

At present, most commercially available HPPD inhibitor herbicides belong to one of these four chemical families:
1) the triketones, e.g. sulcotrione [i.e. 2-[2-chloro-4-(methylsulfonyl)benzoyl]-1,3-cyclohexanedione], mesotrione [i.e. 2-[4-(methylsulfonyl)-2-nitrobenzoyl]-1,3-cyclohexanedione]; tembotrione [i.e. 2-[2-chloro-4-(methylsulfonyl)-3-[(2,2,2,-tri-fluoroethoxy)methyl]benzoyl]-1,3-cyclo-hexanedione]; tefuryltrione [i.e. 2-[2-chloro-4-(methylsulfonyl)-3-[[(tetrahydro-2-furanyl)methoxy]methyl]benzoyl]-1,3-cyclohexanedione]]; bicyclopyrone [i.e. 4-hydroxy-3-[[2-[(2-methoxyethoxy)methyl]-6-(trifluoromethyl)-3-pyridinyl]carbonyl]bicyclo[3.2.1]oct-3-en-2-one]; Benzobicyclon [i.e. 3-(2-chloro-4-mesylbenzoyl)-2-phenylthiobicyclo[3.2.1]oct-2-en-4-one]
2) the diketonitriles, e.g. 2-cyano-3-cyclopropyl-1-(2-methylsulphonyl-4-trifluoromethylphenyl)-propane-1,3-dione and 2-cyano-1-[4-(methylsulphonyl)-2-trifluoromethylphenyl]-3-(1-methylcyclopropyl)propane-1,3-dione;
3) the isoxazoles, e.g. isoxaflutole [i.e. (5-cyclopropyl-4-isoxazolyl)[2-(methylsulfonyl)-4-(trifluoromethyl)phenyl]methanone]. In plants, the isoxaflutole is rapidly metabolized in DKN, a diketonitrile compound which exhibits the HPPD inhibitor property; and
4) the pyrazolinates, e.g. topramezone [i.e. [3-(4,5-dihydro-3-isoxazolyl)-2-methyl-4-(methylsulfonyl)phenyl](5-hydroxy-1-methyl-1H-pyrazol-4-yl)methanone], and pyrasulfotole [(5-hydroxy-1,3-dimethylpyrazol-4-yl(2-mesyl-4-trifluaromethylphenyl)methanone]; pyrazofen [2-[4-(2,4-dichlorobenzoyl)-1,3-dimethylpyrazol-5-yloxy] acetophenone].

These HPPD-inhibiting herbicides can be used against grass and/or broad leaf weeds in crop plants that display metabolic tolerance, such as maize (*Zea mays*) in which they are rapidly degraded (Schulz et al., (1993). FEBS letters, 318, 162-166; Mitchell et al., (2001) Pest Management Science, Vol 57, 120-128; Garcia et al., (2000) Biochem., 39, 7501-7507; Pallett et al., (2001) Pest Management Science, Vol 57, 133-142). In order to extend the scope of these HPPD-inhibiting herbicides, several efforts have been developed in order to confer to plants, particularly plants without or with an underperforming metabolic tolerance, a tolerance level acceptable under agronomic field conditions.

Besides the attempt of by-passing HPPD-mediated production of homogentisate (U.S. Pat. No. 6,812,010), overexpressing the sensitive enzyme so as to produce quantities of the target enzyme in the plant which are sufficient in relation to the herbicide has been performed (WO96/38567). Overexpression of HPPD resulted in better pre-emergence tolerance to the diketonitrile derivative (DKN) of isoxaflutole (IFT), but tolerance was not sufficient for tolerance to post-emergence treatment (Matringe et al., (2005), Pest Management Science 61: 269-276).

A third strategy was to mutate the HPPD in order to obtain a target enzyme which, while retaining its properties of catalysing the transformation of HPP into homogentisate, is less sensitive to HPPD inhibitors than is the native HPPD before mutation.

This strategy has been successfully applied for the production of plants tolerant to 2-cyano-3-cyclopropyl-1-(2-methylsulphonyl-4-trifluoromethylphenyl)-propane-1,3-dione and to 2-cyano-1-[4-(methylsulphonyl)-2-trifluoromethylphenyl]-3-(1-methylcyclopropyl)propane-1,3-dione (EP496630), two HPPD-inhibiting herbicides belonging to the diketonitriles family (WO 99/24585). Pro215Leu, Gly336Glu, Gly336Ile, and more particularly Gly336Trp (positions of the mutated amino acid are indicated with reference to the *Pseudomonas* HPPD) were identified as mutations which are responsible for an increased tolerance to pre-emergence treatment with these diketonitrile herbicides without causing an alteration of the activity of the enzyme.

More recently, introduction of a *Pseudomonas* HPPD gene into the plastid genome of tobacco and soybean has shown to be more effective than nuclear transformation, conferring even tolerance to post-emergence application of isoxaflutole (Dufourmantel et al., 2007, Plant Biotechnol J. 5(1):118-33).

In WO 04/024928, the inventors have sought to increase the prenylquinone biosynthesis (e.g., synthesis of plastoquinones, tocopherols) in the cells of plants by increasing the flux of the HPP precursor into the cells of these plants. This has been done by connecting the synthesis of said precursor to the "shikimate" pathway by overexpression of a PDH enzyme. They have also noted that the transformation of plants with a gene encoding a PDH enzyme makes it possible to increase the tolerance of said plants to HPPD inhibitors.

In the patent application WO 2009/144079, a nucleic acid sequence encoding a mutated hydroxyphenylpyruvate dioxygenase (HPPD) at position 336 of the *Pseudomonas fluorescens* HPPD protein and its use for obtaining plants which are tolerant to HPPD inhibitor herbicides is disclosed.

In WO 2002/046387, several domains of HPPD proteins originating from plants have been identified that may be relevant to confer tolerance to various HPPD inhibitor herbicides but no in planta nor biochemical data have been shown to confirm the impact of the as described domain functions.

In WO 2008/150473, the combination of two distinct tolerance mechanisms—a modified *Avena sativa* gene coding for a mutant HPPD enzyme and a CYP450 Maize monooxygenase (nsf1 gene)—was exemplified in order to obtain an improved tolerance to HPPD inhibitor herbicides, but no data have been disclosed demonstrating the synergistic effects based on the combination of both proteins.

Despite these successes obtained for the development of plants showing tolerance to several HPPD inhibitors herbicides described above, it is still necessary to develop and/or improve the tolerance of plants to newer or to several different HPPD inhibitors, particularly HPPD inhibitors belonging to the classes of the triketones (e.g. sulcotrione, mesotrione, tembotrione, benzobicyclon and bicyclopyrone) and the pyrazolinates (e.g., topramezone and pyrasulfotole).

DESCRIPTION

The present invention therefore relates to the generation of transgenic plants containing a gene encoding an HPPD protein obtainable or obtained from an organism belonging to the family of Blepharismidae, and variants or mutants thereof, more especially to a gene from an organism belonging to the genus *Blepharisma*, variants or mutants thereof coding for an HPPD enzyme showing the properties of catalysing the conversion of para-hydroxyphenylpyruvate to homogentisate and which plants are less sensitive to HPPD inhibitors than plants not containing any such HPPD encoding transgene.

The genes from Blepharismidae coding for HPPD proteins were selected as excellent HPPD-inhibitor tolerant candidates due to their high divergences in the amino acids composition at positions relevant for HPPD inhibitor tolerance as determined experimentally and structurally in the HPPD protein compared to the sensitive *Arabidopsis* HPPD protein which was taken as the HPPD-inhibitor herbicide sensitive reference molecule.

More especially, the present invention therefore relates to the generation of transgenic plants containing a gene obtainable or obtained from an organism belonging to the family of Blepharismidae, especially from the genus *Blepharisma*, more especially obtained from the species *Blepharisma japonicum*, variants or mutants thereof, coding for an HPPD enzyme showing the properties of catalysing the conversion of para-hydroxyphenylpyruvate to homogentisate and which are less sensitive to HPPD inhibitors than plants not containing any such HPPD transgene.

In one embodiment, this invention relates to an HPPD protein named herein "the HPPD protein of this invention" or "the *Blepharisma* HPPD protein", which is an HPPD protein with at least 75%, at least 80%, at least 85%, at least 90%, at least 95%; at least 97%; at least 98%, or at least 99% amino acid sequence identity to the amino acid sequence of SEQ ID No. 4 from amino acid position 2 to 382, particularly to the amino acid sequence of any one of SEQ ID Nos. 4, 5, 6 or 7, preferably SEQ ID No. 6.

In a further embodiment, the invention relates to an HPPD protein named herein "the HPPD protein of this invention" or "the *Blepharisma* HPPD protein", which is an HPPD protein with at least 75%, at least 80%, at least 85%, at least 90%, at least 95%; at least 97%; at least 98%, or at least 99% amino acid sequence identity to the amino acid sequence of SEQ ID No. 4 from amino acid position 2 to 382, particularly to the amino acid sequence of any one of SEQ ID Nos. 4, 5, 6, 7, preferably SEQ ID No. 6, and in which any amino acids from position 185 to position 382 of SEQ ID No. 4 can be amended by any naturally-occurring amino acid, preferentially it can be any conservative substitution.

In a further embodiment, the invention relates to an HPPD protein named herein "the HPPD protein of this invention" or "the *Blepharisma* HPPD protein", which is an HPPD protein with at least 75%, at least 80%, at least 85%, at least 90%, at least 95%; at least 97%; at least 98%, or at least 99% amino acid sequence identity to the amino acid sequence of SEQ ID No. 4 from amino acid position 2 to 382, particularly to the amino acid sequence of any one of SEQ ID Nos. 4, 5, 6, 7, preferably SEQ ID No. 6, and having one or more of the following amino acids at the position defined by its number (relating to the number of SEQ ID No. 4) given in brackets, i.e. His(183), Ser(226), Asn(241), Gln(265), His(266), Tyr (295), Gln(334), Phe(347), Glu(349), Gly(360), and Asn (363).

In a further embodiment, the invention relates to an HPPD protein named herein "the HPPD protein of this invention" or "the Kordia HPPD protein", which is an HPPD protein with at least 75%, at least 80%, at least 85%, at least 90%, at least 95%; at least 97%; at least 98%, or at least 99% amino acid sequence identity to the amino acid sequence of SEQ ID No. 4 from amino acid position 2 to 382, particularly to the amino acid sequence of any one of SEQ ID Nos. 4, 5, 6, 7, preferably SEQ ID No. 6, and at the respective positions given in the second column of Table (i) the originally occurring amino acids can substituted by any of the amino acids listed in column 3 of Table (i).

TABLE (i)

| Amino acid in SEQ ID No. 4 | Position in SEQ ID No. 4 | Substitutions |
| --- | --- | --- |
| Val | 185 | Thr, Cys, Ala, Gly |
| Tyr | 209 | Phe, Ile, Leu, Val, Ala, Gln, Glu, Asp, Gly, Thr, Ser, Met, Arg, Lys |
| Trp | 210 | Ala, Ile, Leu, Ser, Arg, Lys, His, Asp, Glu, Pro, Gly, Asn |
| Ala | 212 | Phe, Val, Ile, Leu, Trp, Met, Gln, His |
| Leu | 224 | Met, Val |
| Val | 227 | Ala, Leu, Met, Ile, Lys, Arg, Gln, Tyr |
| Val | 229 | Leu, Met, Ile, Ala |
| Ala | 230 | Ser, Thr, Val, Arg, Lys, Glu, Leu, Ile, Met, His |
| Ala | 366 | Glu, Gln, Ser, Val, Phe, Thr |
| Leu | 367 | Arg |

TABLE (ii)

| Amino acid in SEQ ID No. 4 | Position in SEQ ID No. 4 | Substitutions |
| --- | --- | --- |
| Ser | 211 | Glu, Thr, Tyr, Phe, His, Gln, Asn, Gly, Leu, Met, Val, Arg, Ile |
| Val | 228 | Ala, Thr |
| Pro | 239 | Ala, Val, Thr, Asn, Ile, |
| Leu | 289 | Met, Ile, Asn |
| Leu | 323 | Met |
| Ile | 361 | Any except Pro |
| Gly | 362 | Ala, Pro, Val, Thr, Met |

In a further embodiment, the invention relates to an HPPD protein named herein "the HPPD protein of this invention" or "the Kordia HPPD protein", which is an HPPD protein with at least 75%, at least 80%, at least 85%, at least 90%, at least 95%; at least 97%; at least 98%, or at least 99% amino acid sequence identity to the amino acid sequence of SEQ ID No. 4 from amino acid position 2 to 382, particularly to the amino acid sequence of any one of SEQ ID Nos. 4, 5, 6, 7, preferably SEQ ID No. 6, and at the respective positions given in the second column of Table (ii) the originally occurring amino acids can substituted by any of the amino acids listed in column 3 of Table (ii).

TABLE (iii)

| Amino acid in SEQ ID No. 4 | Position in SEQ ID No. 4 | Substitutions |
| --- | --- | --- |
| Ser | 211 | Glu, Thr, Arg, Tyr |
| Val | 228 | Ala |
| Pro | 239 | Ala, Val, Thr |
| Leu | 289 | Met |
| Leu | 323 | Met |
| Ile | 361 | Ala, Val, Leu, Lys |
| Gly | 362 | Ala |

In a further embodiment, the invention relates to an HPPD protein named herein "the HPPD protein of this invention" or "the Kordia HPPD protein", which is an HPPD protein with at least 75%, at least 80%, at least 85%, at least 90%, at least 95%; at least 97%; at least 98%, or at least 99% amino acid sequence identity to the amino acid sequence of SEQ ID No. 4 from amino acid position 2 to 382, particularly to the amino acid sequence of any one of SEQ ID Nos. 4, 5, 6, 7, preferably SEQ ID No. 6, and at the respective positions given in the second column of Table (iii) the originally occurring amino acids can substituted by any of the amino acids listed in column 3 of Table (iii).

This invention includes a protein with amino acids substituted, deleted or added compared to the sequence of SEQ ID No. 4 from amino acid position 2 to amino acid position 382, such as a transit peptide fusion protein, or a protein with amino acid changes in the sequence of SEQ ID No. 4 that retains the enzymatic function of an HPPD protein, and that still confers HPPD tolerance when expressed in plants, preferably HPPD tolerance of comparable range to that conferred by the protein of SEQ ID No. 4. This includes variant or mutant proteins derived from the protein of SEQ ID No. 4, such as any of the proteins of SEQ ID NO: 5, 6 or 7, particularly such mutant or variant which is less sensitive than the host plant's endogenous HPPD to an HPPD inhibitor herbicide of the class of isoxazoles, diketonitriles, triketones or pyrazolinates, preferably such mutant or variant which confers agronomically relevant herbicide tolerance to a host plant expressing it when an HPPD inhibitor herbicide of the class of isoxazoles, diketonitriles, triketones and/or pyrazolinates, particularly any one of mesotrione, tembotrione, isoxaflutole or bicyclopyrone is applied on such plants, more particularly when applied post-emergence. This also includes a protein comprising an active portion of the sequence of SEQ ID NO:4, which portion confers HPPD inhibitor tolerance when expressed in plants. This includes a protein with substantially the same amino acid sequence as the sequence of SEQ ID NO:4, such as a protein with the amino acid sequence of any one of SEQ ID No. 4 to 7. This includes isolated proteins as defined below, and also proteins, such as the protein of SEQ ID NO:4 wherein certain amino acids have been replaced by similar amino acids as defined below, preferably conservative amino acid substitutions. Also included herein as HPPD proteins of this invention are HPPD proteins comprising the amino acid sequence of SEQ ID No. 4 from amino acid position 2 to 382, but wherein 1-20, 1-15, 1-10, or 1, 2, 3, 4, 5, 6, 7, 8, or 9 amino acids have been deleted or have been substituted by other amino acids, particularly such protein which retains HPPD enzymatic activity and which confers tolerance to HPPD inhibitor herbicides when expressed in a host plant. Included herein are HPPD proteins encoded by DNA sequences homologous to the DNA sequences of the invention as described below, or HPPD proteins encoded by a DNA sequence which hybridizes to at least a portion (of at least 20-30 nucleotides) of the DNA of SEQ ID NO:1, or which is obtainable using a primer based on SEQ ID NO:1, or HPPD proteins with at least 75% sequence identity to SEQ ID No:4 which are encoded by a DNA sequence found in the genome sequence of a microorganism, such as a eukaryotic microorganism, particularly a protist, such as a microorganism of the family Blepharismidae. Included herein as an HPPD protein of this invention is a Blepharismidae HPPD protein which confers herbicide tolerance to plants when expressed in such plants, wherein such tolerance is to an HPPD inhibitor such as mesotrione, tembotrione, isoxaflutole or bicyclopyrone, particularly such HPPD protein is a *Blepharisma japonicum* HPPD protein, such as a protein comprising the sequence of SEQ ID NO: 4 from amino acid position 2 to 382. This includes the mutant or variant HPPD proteins as described further below.

The present invention includes and provides an antibody capable of specifically binding a substantially purified protein comprising an amino acid sequence selected from the group consisting of SEQ ID NOs: 4, 5, 6, or 7, or derived sequences thereof according to amino acid replacement as disclosed in one or more of tables (i), (ii) or (iii), above.

A further aspect of the invention concerns antibodies, single-chain antigen binding molecules, or other proteins that specifically bind to one or more of the protein or peptide molecules of the invention and their homologs, fusions or fragments. In a particularly preferred embodiment, the antibody specifically binds to a protein having the amino acid sequence set forth in SEQ ID NOs: 4-7 or a fragment thereof, or derived sequences thereof according to amino acid replacement as disclosed in one or more of tables (i), (ii) or (iii), above.

In another embodiment, the antibody specifically binds to a fusion protein comprising an amino acid sequence selected from the amino acid sequence set forth in SEQ ID NOs: 4-7 or a fragment thereof. In another embodiment the antibody specifically binds to a fusion protein comprising an amino acid sequence selected from the amino acid sequence set forth in SEQ ID NOs: 4-7 or a fragment thereof, or derived sequences thereof according to amino acid replacement as disclosed in one or more of tables (i), (ii) or (iii), above.

Antibodies of the invention may be used to quantitatively or qualitatively detect the protein or peptide molecules of the invention, or to detect post translational modifications of the proteins. As used herein, an antibody or peptide is said to "specifically bind" to a protein or peptide molecule of the invention if such binding is not competitively inhibited by the presence of non-related molecules.

In another embodiment this invention relates to an HPPD nucleic acid or DNA, named herein "the HPPD nucleic acid/DNA of this invention", which is a nucleic acid or DNA encoding an HPPD of this invention as defined above. This includes a DNA which comprises a nucleotide sequence selected from the group consisting of the sequence of SEQ ID No. 1 from nucleotide position 4 to nucleotide position 1147, the sequence of SEQ ID No. 2 from nucleotide position 25 to nucleotide position 1167, or the sequence of SEQ ID No. 3 from nucleotide position 4 to nucleotide position 1542, or which comprises a DNA region which encodes an HPPD, or a DNA which is sufficiently complementary to another DNA so that when it is incubated at a temperature of between 60 and 65° C. in 5×SSC (1×SSC (single-strength sodium citrate) means=0.15M NaCl, 0.015 M trisodium-citrate, 50 mM sodium phosphate pH 7.6), containing 0.1% SDS followed by rinsing at the same temperature with 5×SSC containing 0.1% SDS, it still hybridizes with a sequence selected from the group consisting of SEQ ID Nos. 1, 2, and 3. When the test and inventive sequences are double stranded the nucleic acid constituting the test sequence preferably has a TM within 10° C. of that of the sequence selected from the group consisting of SEQ ID Nos 1, 2, and 3. In the case that the test and the sequence selected from the group consisting of SEQ ID Nos. 1, 2, and 3 are mixed together and are denatured simultaneously, the TM values of the sequences are preferably within 5° C. of each other. More preferably the hybridization is performed under relatively stringent hybridization conditions as defined below.

In one embodiment, a denatured test or inventive sequence is preferably first bound to a support and hybridization is effected for a specified period of time at a temperature of between 60 and 65° C. in 5×SSC containing 0.1% SDS followed by rinsing of the support at the same temperature but with 0.1×SSC. Where the hybridization involves a fragment of the sequence selected from the group consisting of SEQ ID Nos. 1, 2, and 3 the hybridization conditions may be less stringent, as will be obvious to the skilled person.

Also included herein as HPPD DNA of this invention, are DNA sequences encoding an HPPD protein of the invention which DNA sequences have been adapted for expression in microorganisms or plants, such as by replacing native codons by codons more preferred in a host cell, or wherein certain restriction sites have been added or removed for ease of cloning, or DNA sequence with a certain number of added, replaced or deleted nucleotides. This also includes isolated DNA sequences and variant, mutant or synthetic DNAs or nucleic acids as described further below.

In a particular embodiment, the *Blepharisma* HPPD DNA of this invention is expressed in plants under the control of a promoter that allows expression of exogenous genes in plants. In a further particular embodiment, at the N-terminus of the so expressed HPPD enzyme a signal transit peptide, such as a transit peptide is located, preferably a plastid transit peptide, such as a chloroplast transit peptide of about 120 amino acids (about 30 to about 120 amino acids) most preferably a double transit peptide, such as an optimized transit peptide of which the first part is originated from Sunflower (*Helianthus annuus*) and the second part from *Zea mays* (described in U.S. Pat. No. 5,188,642) or a plastid transit peptide of that of the plant ribulose biscarboxylase/oxygenase small subunit (RuBisCO ssu), where appropriate including a few amino acids of the N-terminal part of the mature RuBisCO ssu (EP 189 707)

In a further particular embodiment, this invention includes a DNA encoding an HPPD protein of this invention which is derived or is obtainable from SEQ ID No. 1 and is optimized for the expression in *E. coli*, such as a codon-optimized DNA, for example a DNA comprising the sequence of SEQ ID No. 2 from nucleotide position 25 to nucleotide position 1167 (including the positions defined).

In a further particular embodiment, this invention includes a DNA encoding an HPPD protein of this invention which is derived from SEQ ID No. 1 and is optimized for the expression in plants, such as a codon-optimized DNA, for example a DNA comprising the sequence of SEQ ID No. 3 from nucleotide position 400 to nucleotide position 1542 (including the positions defined).

In a further particular embodiment, the HPPD of the invention, such as the HPPD comprising the amino acid sequence of SEQ ID No. 4 from amino acid position 2 to amino acid position 382, or the HPPD comprising the amino acid sequence of any one of SEQ ID Nos. 4 to 7, is less sensitive than the host plant endogenous HPPD to an HPPD inhibitor herbicide of the class of isoxazoles, diketonitriles, triketones or pyrazolinates, or an HPPD inhibitor herbicide selected from isoxaflutole, tembotrione, mesotrione, sulcotrione, pyrasulfotole, topramezone, 2-cyano-3-cyclopropyl-1-(2-$SO_2CH_3$-4-$CF_3$-phenyl)propane-1,3-dione and 2-cyano-3-cyclopropyl-1-(2-$SO_2CH_3$-4-2,3 $Cl_2$ phenyl)propane-1,3-dione, bicyclopyrone, benzobicyclon, tefuryltrione, and pyrazoxyfen.

In a further particular embodiment, this invention includes a DNA encoding an HPPD protein of this invention which is optimized for the expression in *E. coli*, such as a codon-optimized DNA, for example a DNA comprising the sequence of SEQ ID No. 2 from nucleotide position 25 to nucleotide position 1167 (including the positions defined) which encodes an HPPD less sensitive than the host plant endogenous HPPD to at least one HPPD inhibitor herbicide of the class of isoxazoles, diketonitriles, triketones or pyrazolinates, preferably to tembotrione, mesotrione, bicyclopyrone, tefuryltrione, isoxaflutole, diketonitrile, pyrasulfotole, topramezone, sulcotrione, pyrazolate and benzofenap.

In a further particular embodiment, this invention includes a DNA encoding an HPPD protein of this invention which is optimized for the expression in plants, such as a codon-optimized DNA, for example a DNA comprising the sequence of SEQ ID No. 3 from nucleotide position 400 to nucleotide position 1542 (including the positions defined) which encodes an HPPD less sensitive than the host plant endogenous HPPD to at least one HPPD inhibitor herbicide of the class of isoxazoles, diketonitriles, triketones or pyrazolinates, preferably to tembotrione, mesotrione, bicyclopyrone, tefuryltrione, isoxaflutole, diketonitrile, pyrasulfotole, topramezone, sulcotrione, pyrazolate and benzofenap.

In a further particular embodiment, this invention relates to plants, plant parts, plant cells, and progenies of these plants comprising a DNA encoding an HPPD protein of the invention which is optimized for the expression in *E. coli*, or is optimized for the expression in plants such as a codon-optimized DNA, for example a DNA comprising the sequence of SEQ ID No. 2 from nucleotide position 25 to nucleotide position 1167 (including the positions defined) or of SEQ ID No. 3 from nucleotide position 400 to nucleotide position 1542 (including the positions defined) which encodes an HPPD less sensitive than the host plant endogenous HPPD. Such plants include but are not limited to field crops, fruits and vegetables such as canola, sunflower, tobacco, sugarbeet, cotton, maize, wheat, barley, rice, sorghum, tomato, mango, peach, apple, pear, strawberry, banana, melon, potato, carrot, lettuce, cabbage, onion, soya spp, sugar cane, pea, field beans, poplar, grape, citrus, alfalfa, rye, oats, turf and forage grasses, flax and oilseed rape, and nut producing plants.

In a more particular embodiment, this invention relates plants, plant parts, plant cells, and progenies of these plants comprising a DNA encoding an HPPD protein of the invention which is optimized for the expression in *E. coli*, or optimized for the expression in plants such as a codon-optimized DNA, for example a DNA comprising the sequence of SEQ ID No. 2 from nucleotide position 25 to nucleotide position 1167 (including the positions defined) or of SEQ ID No. 3 from nucleotide position 400 to nucleotide position 1542 (including the positions defined) which encodes an HPPD less sensitive than the host plant endogenous HPPD and wherein the plants are selected from the group consisting of canola, sunflower, tobacco, sugarbeet, cotton, maize, wheat, barley, rice, potato, soya spp, sugar cane, pea, field beans, poplar, grape, alfalfa, rye, oats, turf and forage grasses, flax and oilseed rape, and nut producing plants, even more preferably such plants are selected from the group consisting of soya spp, rice, sugarbeet, wheat, cotton canola, oilseed rape or maize.

In another particular embodiment, the HPPD protein of the invention comprises the sequence of SEQ ID No. 7 and is less sensitive to an HPPD inhibitor of the class of triketones (named triketone HPPD inhibitor), such as tembotrione, sulcotrione mesotrione, bicyclopyrone, tefuryltrione, particularly tembotrione, or of the class diketonitrile (isoxaflutole) or of the class of pyrazolinates (named pyrazolinate HPPD inhibitor), such as pyrasulfotole, pyrazolate, topramezone, benzofenap compared to the endogenous unmutated HPPD of a plant, particularly the host plant wherein such HPPD of the invention is expressed or is to be expressed.

The enzymatic activity of HPPD proteins can be measured by any method that makes it possible either to measure the decrease in the amount of the HPP or $O_2$ substrates, or to measure the accumulation of any of the products derived from the enzymatic reaction, i.e. homogentisate or $CO_2$. In particular, the HPPD activity can be measured by means of the method described in Garcia et al. (1997), Biochem. J. 325, 761-769 or Garcia et al. (1999), Plant Physiol. 119, 1507-1516, which are incorporated herein by reference.

According to the invention, an HPPD inhibitor of the class of triketones (or triketone HPPD inhibitor) means an HPPD inhibitor having a triketone skeleton. As an example of such triketone HPPD inhibitor, one can cite the molecules sulcotrione [i.e. 2-[2-chloro-4-(methylsulfonyl)benzoyl]-1,3-cyclohexanedione], mesotrione [i.e. 2-[4-(methylsulfonyl)-2-nitrobenzoyl]-1,3-cyclohexanedione], and tembotrione [i.e. 2-[2-chloro-4-(methylsulfonyl)-3-[(2,2,2,-tri-fluoroethoxy)methyl]benzoyl]-1,3-cyclo-hexanedione], tefuryltrione [i.e. 2-{2-chloro-4-mesyl-3-[(RS)-tetrahydro-2-furylmethoxymethyl]benzoyl}cyclohexane-1,3-dione], bicyclopyrone [i.e. 4-hydroxy-3-{2-[(2-methoxyethoxy)methyl]-6-(trifluoromethyl)-3-pyridylcarbonyl}bicyclo[3.2.1]oct-3-en-2-one], benzobicyclon [i.e. 3-(2-chloro-4-mesylbenzoyl)-2-phenylthiobicyclo[3.2.1]oct-2-en-4-one].

According to the invention, an HPPD of the class of pyrazolinates (or pyrazolinate HPPD inhibitor) means an HPPD inhibitor having a pyrazole radical. As an example of such pyrazolinates HPPD inhibitor, one can cite the molecules topramezone [i.e. [3-(4,5-dihydro-3-isoxazolyl)-2-methyl-4-(methylsulfonyl)phenyl](5-hydroxy-1-methyl-1H-pyrazol-4-yl)methanone] and pyrasulfotole [(5-hydroxy-1,3-dimethylpyrazol-4-yl(2-mesyl-4-trifluaromethylphenyl)methanone].

The present invention also relates to a nucleic acid sequence, particularly an isolated DNA, preferably a plant-expressible chimeric gene, which encodes the *Blepharisma* HPPD of the invention and adapted sequences thereof.

The present invention also relates to a nucleic acid sequence encoding an HPPD enzyme of this invention which retains its properties of catalysing the conversion of para-hydroxyphenylpyruvate to homogentisate and which is less sensitive to HPPD inhibitors of the class of triketones such as tembotrione, sulcotrione and mesotrione, or of the class of pyrazolinates such as pyrasulfotole and topramezone, tefuryltrione, bicyclopyrone, benzobicyclon than the endogenous unmutated plant HPPD, and of which the encoded amino acid sequence shows a sequence identity to SEQ ID No. 4 of at least 75%, 80%, particularly at least 85%, preferably at least 90%, more preferably at least 95%, even more preferably at least 98% and most preferably at least 99%.

In a more particular embodiment, the nucleic acid sequence of the invention encodes an HPPD enzyme which is less sensitive to an HPPD inhibitor of the class of triketones such as tembotrione, sulcotrione, mesotrione, bicyclopyrone, and tefuryltrione, the class of isoxazoles such as isoxaflutole of the class of pyrazolinates (named pyrazolinate HPPD inhibitor), such as pyrasulfotole, pyrazolate, topramezone, benzofenap, or the class of diketones such as diketonitrile than the host plant endogenous HPPD.

According to the present invention, a "nucleic acid sequence" is understood as being a nucleotide sequence which can be of the DNA or RNA type, preferably of the DNA type, and in particular double-stranded, whether it be of natural or synthetic origin, in particular a DNA sequence in which the codons which encode the HPPD according to the invention have been optimized in accordance with the host organism in which it is to be expressed (e.g., by replacing codons with those codons more preferred or most preferred in codon usage tables of such host organism or the group to which such host organism belongs, compared to the original or source organism).

An "isolated nucleic acid/DNA/protein", as used herein, refers to a nucleic acid/DNA/protein which is not naturally occurring (such as an artificial or synthetic DNA with a different nucleotide sequence than the naturally occurring DNA, or a modified protein) or which is no longer in the natural environment wherein it was originally present, e.g., a DNA coding sequence associated with a heterologous regulatory element (such as a bacterial coding sequence operably linked to a plant-expressible promoter) in a chimeric gene, a DNA transferred into another host cell, such as a transgenic plant cell.

In view of a particular embodiment of the invention and the sought-after solution, i.e. an HPPD which is less sensitive to a triketone, an isoxazole, or pyrazolinate HPPD inhibitor, the tolerance level measurement is analyzed using the method extensively described in WO 2009/14407 as described below using a triketone, an isoxazole, or a pyrazolinate HPPD inhibitor, particularly an HPPD inhibitor selected from tembotrione, mesotrione, pyrasulfotole, topramezone sulcotrione, bicyclopyrone, diketonitrile, benzofenap, pyrazolate, tefuryltrione.

The terminology DNA or protein "comprising" a certain sequence "X", as used throughout the text, refers to a DNA or protein including or containing at least the sequence "X", so that other nucleotide or amino acid sequences can be included at the 5' (or N-terminal) and/or 3' (or C-terminal) end, e.g. (the nucleotide sequence of) a selectable marker protein, (the nucleotide sequence of) a transit peptide, and/or a 5' leader sequence or a 3' trailer sequence. Similarly, use of the term "comprise", "comprising" or "comprises" throughout the text and the claims of this application should be understood to imply the inclusion of a stated integer or step or group of integers or steps but not the exclusion of any other integer or step or group of integers or steps.

In one embodiment of the invention, the coding regions encoding HPPD comprise a nucleotide sequence encoding proteins with the amino acid sequences as set forth in SEQ ID Nos 4, 5, 6, and 7 such as the nucleotide sequences of SEQ ID Nos 1, 2, and 3.

However, it will be clear that variants of these nucleotide sequences, including insertions, deletions and substitutions thereof may be also be used to the same effect. Equally, homologues to the mentioned nucleotide sequences from species different from *Blepharisma* can be used.

Variants of the described nucleotide sequence will have a sequence identity which is preferably at least about 70%, 80%, or 85 or 90% or at least 95% with identified nucleotide sequences encoding HPPD enzymes such as the ones identified in the sequence listing.

A protein with "substantially the same amino acid sequence" to a protein as described in the invention, as used herein, refers to a protein with at least 90%, particularly at least 95%, preferably at least 97% sequence identity with a protein according to the invention, wherein the percentage sequence identity is determined by using the blosum62 scoring matrix in the GAP program of the Wisconsin package of GCG (Madison, Wis., USA) version 10.0 (GCG defaults used). "Sequence identity", as used throughout this application, when related to proteins, refers to the percentage of identical amino acids using this specified analysis. The "sequence identity", as used herein, when related to DNA sequences, is determined by using the nwsgapdna scoring matrix in the GAP program of the Wisconsin package of GCG (Madison, Wis., USA) version 10.0 (GCG defaults used).

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970). The computer-assisted sequence alignment above, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

Nucleotide sequences homologous to the nucleotide sequences encoding an HPPD enzyme according to the invention may be identified by in silico analysis of genomic sequence data.

Homologous nucleotide sequence may also be identified and isolated by hybridization under stringent conditions using as probes identified nucleotide sequences encoding HPPD enzymes according to the invention or parts thereof. Such parts should preferably have a nucleotide sequence comprising at least 40 consecutive nucleotides from the coding region of HPPD encoding genes sequences according to the invention, preferably from the coding region of SEQ ID No. 1, SEQ ID No. 2 or SEQ ID No. 3. The probes may however comprise longer regions of nucleotide sequences derived from the HPPD encoding nucleic acids, such as about 50, 60, 75, 100, 200 or 500 consecutive nucleotides from any of the mentioned HPPD genes. Preferably, the probe should comprise a nucleotide sequence coding for a highly conserved region which may be identified by aligning the different HPPD proteins.

"Stringent hybridization conditions" as used herein means that hybridization will generally occur if there is at least 95% and preferably at least 97% sequence identity between the probe and the target sequence. Examples of stringent hybridization conditions are overnight incubation in a solution comprising 5×SSC (150 mM NaCl, 15 mM trisodium-citrate), 50 mM sodium phosphate (pH 7.6), 5×Denhardt's solution, 10% dextran sulfate, and 20 µg/ml denatured, sheared carrier DNA such as salmon sperm DNA, followed by washing the hybridization support in 0.1×SSC at approximately 65° C., preferably twice for about 10 minutes. Other hybridization and wash conditions are well known and are exemplified in Sambrook et al, Molecular Cloning: A Laboratory Manual, Second Edition, Cold Spring Harbor, N.Y. (1989), particularly chapter 11.

Such variant sequences may also be obtained by DNA amplification using oligonucleotides specific for HPPD genes encoding enzymes as primers, such as but not limited to oligonucleotides comprising about 20 to about 50 consecutive nucleotides selected from the nucleotide sequences of SEQ ID Nos 1, 2, 3 or their complement.

The invention also encompasses variant HPPD enzymes which are amino acid sequences similar to the HPPD amino acid sequence of SEQ ID No. 4 wherein one or more amino acids have been inserted, deleted or substituted. In the present context, variants of an amino acid sequence refer to those polypeptides, enzymes or proteins which have a similar catalytic activity as the amino acid sequences described herein, notwithstanding any amino acid substitutions, additions or deletions thereto. Preferably the variant amino acid sequence has a sequence identity of at least about 80%, or 85 or 90% or 95% with the amino acid sequence of SEQ ID No. 4. Also preferably, a polypeptide comprising the variant amino acid sequence has HPPD enzymatic activity. Methods to determine HPPD enzymatic activity are well known in the art and include assays as extensively described in WO 2009/144079 or in WO 2002/046387.

Substitutions encompass amino acid alterations in which an amino acid is replaced with a different naturally-occurring or a non-conventional amino acid residue. Such substitutions may be classified as "conservative', in which an amino acid residue contained in an HPPD protein of this invention is replaced with another naturally-occurring amino acid of similar character, for example Gly↔Ala, Val↔Ile↔Leu, Asp↔Glu, Lys↔Arg, Asn↔Gln or Phe↔Trp↔Tyr. Substitutions encompassed by the present invention may also be "non-conservative", in which an amino acid residue which is present in an HPPD protein of the invention is substituted with an amino acid with different properties, such as a naturally-occurring amino acid from a different group (eg. substituting a charged or hydrophobic amino acid with alanine. Amino acid substitutions are typically of single residues, but may be of multiple residues, either clustered or dispersed. Amino acid deletions will usually be of the order of about 1-10 amino acid residues, while insertions may be of any length. Deletions and insertions may be made to the N-terminus, the C-terminus or be internal deletions or insertions. Generally, insertions within the amino acid sequence will be smaller than amino- or carboxy-terminal fusions and of the order of 1 to 4 amino acid residues. "Similar amino acids", as used herein, refers to amino acids that have similar amino acid side chains, i.e. amino acids that have polar, non-polar or practically neutral side chains. "Non-similar amino acids", as used herein, refers to amino acids that have different amino acid side chains, for example an amino acid with a polar side chain is non-similar to an amino acid with a non-polar side chain. Polar side chains usually tend to be present on the surface of a protein where they can interact with the aqueous environment found in cells ("hydrophilic" amino acids). On the other hand, "non-polar" amino acids tend to reside within the center of the protein where they can interact with similar non-polar neighbours ("hydrophobic" amino acids"). Examples of amino acids that have polar side chains are arginine, asparagine, aspartate, cysteine, glutamine, glutamate, histidine, lysine, serine, and threonine (all hydrophilic, except for cysteine which is hydrophobic). Examples of amino acids that have non-polar side chains are alanine, glycine, isoleucine, leucine, methionine, phenylalanine, proline, and tryptophan (all hydrophobic, except for glycine which is neutral).

Also encompassed by the present invention are antibodies which specifically recognize an HPPD enzyme according to the invention.

The invention also relates to the use, in a method for transforming plants, of a nucleic acid which encodes an HPPD according to the invention as a marker gene or as a coding sequence which makes it possible to confer to the plant tolerance to herbicides which are HPPD inhibitors, and the use of HPPD inhibitors on plants comprising a nucleic acid sequence encoding a HPPD according to the invention. In an embodiment of this invention, in such use the HPPD inhibitors are triketones or pyrazolinates, preferably tembotrione, mesotrione or sulcotrione, bicyclopyrone, and tefuryltrione. It is, of course, understood that this sequence can also be used in combination with (an) other gene marker(s) and/or sequence(s) which encode(s) one or more protein with useful agricultural properties.

In the commercial production of crops, it is desirable to eliminate under reliable pesticidial management unwanted plants (i.e., "weeds") from a field of crop plants. An ideal treatment would be one which could be applied to an entire field but which would eliminate only the unwanted plants while leaving the crop plants unaffected. One such treatment system would involve the use of crop plants which are tolerant to an herbicide so that when the herbicide is sprayed on a field of herbicide-tolerant crop plants, the crop plants would continue to thrive while non-herbicide-tolerant weeds are killed or severely damaged. Ideally, such treatment systems would take advantage of varying herbicide properties so that weed control could provide the best possible combination of flexibility and economy. For example, individual herbicides have different longevities in the field, and some herbicides persist and are effective for a relatively long time after they are applied to a field while other herbicides are quickly broken down into other and/or non-active compounds. An ideal treatment system would allow the use of different herbicides so that growers could tailor the choice of herbicides for a particular situation.

While a number of herbicide-tolerant crop plants are presently commercially available, one issue that has arisen for many commercial herbicides and herbicide/crop combinations is that individual herbicides typically have incomplete spectrum of activity against common weed species. For most individual herbicides which have been in use for some time, populations of herbicide resistant weed species and biotypes have become more prevalent (see, e.g., Tranel and Wright (2002) *Weed Science* 50: 700-712; Owen and Zelaya (2005) *Pest Manag. Sci.* 61: 301-311). Transgenic plants which are resistant to more than one herbicide have been described (see, e.g., WO2005/012515). However, improvements in every aspect of crop production, weed control options, extension of residual weed control, and improvement in crop yield are continuously in demand.

The HPPD protein or gene of the invention is advantageously combined in plants with other genes which encode proteins or RNAs that confer useful agronomic properties to such plants. Among the genes which encode proteins or RNAs that confer useful agronomic properties on the transformed plants, mention can be made of the DNA sequences encoding proteins which confer tolerance to one or more herbicides that, according to their chemical structure, differ from HPPD inhibitor herbicides, and others which confer tolerance to certain insects, those which confer tolerance to certain diseases, DNAs that encodes RNAs that provide nematode or insect control, etc. . . .

Such genes are in particular described in published PCT Patent Applications WO 91/02071 and WO95/06128.

Among the DNA sequences encoding proteins which confer tolerance to certain herbicides on the transformed plant cells and plants, mention can be made of a bar or PAT gene or the *Streptomyces coelicolor* gene described in WO2009/152359 which confers tolerance to glufosinate herbicides, a gene encoding a suitable EPSPS which confers tolerance to herbicides having EPSPS as a target, such as glyphosate and its salts (U.S. Pat. No. 4,535,060, U.S. Pat. No. 4,769,061, U.S. Pat. No. 5,094,945, U.S. Pat. No. 4,940,835, U.S. Pat. No. 5,188,642, U.S. Pat. No. 4,971,908, U.S. Pat. No. 5,145,783, U.S. Pat. No. 5,310,667, U.S. Pat. No. 5,312,910, U.S. Pat. No. 5,627,061, U.S. Pat. No. 5,633,435), or a gene encoding glyphosate oxydoreductase (U.S. Pat. No. 5,463,175).

Among the DNA sequences encoding a suitable EPSPS which confer tolerance to the herbicides which have EPSPS as a target, mention will more particularly be made of the gene which encodes a plant EPSPS, in particular maize EPSPS, particularly a maize EPSPS which comprises two mutations, particularly a mutation at amino acid position 102 and a mutation at amino acid position 106 (WO 2004/074443), and which is described in U.S. Pat. No. 6,566,587, hereinafter named double mutant maize EPSPS or 2mEPSPS, or the gene which encodes an EPSPS isolated from *Agrobacterium* and which is described by SEQ ID No. 2 and SEQ ID No. 3 of U.S. Pat. No. 5,633,435, also named CP4.

Among the DNA sequences encoding a suitable EPSPS which confer tolerance to the herbicides which have EPSPS as a target, mention will more particularly be made of the gene which encodes an EPSPS GRG23 from *Arthrobacter globiformis*, but also the mutants GRG23 ACE1, GRG23 ACE2, or GRG23 ACE3, particularly the mutants or variants of GRG23 as described in WO2008/100353, such as GRG23(ace3) R173K of SEQ ID No. 29 in WO2008/100353.

In the case of the DNA sequences encoding EPSPS, and more particularly encoding the above genes, the sequence encoding these enzymes is advantageously preceded by a sequence encoding a transit peptide, in particular the "optimized transit peptide" described in U.S. Pat. No. 5,510,471 or U.S. Pat. No. 5,633,448.

In WO 2007/024782, plants being tolerant to glyphosate and at least one ALS (acetolactate synthase) inhibitor are disclosed. More specifically plants containing genes encoding a GAT (Glyphosate-N-Acetyltransferase) polypeptide and a polypeptide conferring resistance to ALS inhibitors are disclosed.

In U.S. Pat. No. 6,855,533, transgenic tobacco plants containing mutated *Arabidopsis* ALS/AHAS genes were disclosed.

In U.S. Pat. No. 6,153,401, plants containing genes encoding 2,4-D-monooxygenases conferring tolerance to 2,4-D (2,4-dichlorophenoxyacetic acid) by metabolisation are disclosed.

In US 2008/0119361 and US 2008/0120739, plants containing genes encoding Dicamba monooxygenases conferring tolerance to dicamba (3,6-dichloro-2-methoxybenzoic acid) by metabolisation are disclosed.

All the above mentioned herbicide tolerance traits can be combined with those performing HPPD tolerance which are subject matter of this invention.

Among the DNA sequences encoding proteins concerning properties of tolerance to insects, mention will more particularly be made of the Bt proteins widely described in the literature and well known to those skilled in the art. Mention will also be made of proteins extracted from bacteria such as *Photorhabdus* (WO 97/17432 & WO 98/08932).

Among such DNA sequences encoding proteins of interest which confer novel properties of tolerance to insects, mention will more particularly be made of the Bt Cry or VIP proteins widely described in the literature and well known to those skilled in the art. These include the Cry1F protein or hybrids derived from a Cry1F protein (e.g., the hybrid Cry1A-Cry1F proteins described in U.S. Pat. No. 6,326,169; U.S. Pat. No. 6,281,016; U.S. Pat. No. 6,218,188, or toxic fragments thereof), the Cry1A-type proteins or toxic fragments thereof, preferably the Cry1Ac protein or hybrids derived from the Cry1Ac protein (e.g., the hybrid Cry1Ab-Cry1Ac protein described in U.S. Pat. No. 5,880,275) or the Cry1Ab or Bt2 protein or insecticidal fragments thereof as described in EP451878, the Cry2Ae, Cry2Af or Cry2Ag proteins as described in WO02/057664 or toxic fragments thereof, the Cry1A.105 protein described in WO 2007/140256 (SEQ ID No. 7) or a toxic fragment thereof, the VIP3Aa19 protein of NCBI accession ABG20428, the VIP3Aa20 protein of NCBI accession ABG20429 (SEQ ID No. 2 in WO 2007/142840), the VIP3A proteins produced in the COT 202 or COT 203 cotton events (WO 2005/054479 and WO 2005/054480, respectively), the Cry proteins as described in WO01/47952, the VIP3Aa protein or a toxic fragment thereof as described in Estruch et al. (1996), Proc Natl Acad Sci USA. 28; 93(11): 5389-94 and U.S. Pat. No. 6,291,156, the insecticidal proteins from *Xenorhabdus* (as described in WO98/50427), *Serratia* (particularly from *S. entomophila*) or *Photorhabdus* species strains, such as Tc-proteins from *Photorhabdus* as described in WO98/08932 (e.g., WaterField et al., 2001, Appl Environ Microbiol. 67(11):5017-24; Ffrench-Constant and Bowen, 2000, Cell Mol Life Sci.; 57(5):828-33). Also any variants or mutants of any one of these proteins differing in some (1-10, preferably 1-5) amino acids from any of the above sequences, particularly the sequence of their toxic fragment, or which are fused to a transit peptide, such as a plastid transit peptide, or another protein or peptide, is included herein.

The present invention also relates to a chimeric gene (or expression cassette) which comprises a coding sequence as well as heterologous regulatory elements, at the 5' and/or 3' position, at least at the 5' position, which are able to function in a host organism, in particular plant cells or plants, with the coding sequence containing at least one nucleic acid sequence which encodes an HPPD as previously defined.

In a particular embodiment, the present invention relates to a chimeric gene as previously described, wherein the host organism is selected from bacteria, yeast, *Pichia*, fungi, baculovirus, in vitro cells, protoplasts, plant cells, plants, plant parts, and plant seeds thereof.

In another particular embodiment, the present invention relates to a chimeric gene as previously described, wherein the chimeric gene contains in the 5' position of the nucleic acid sequence which encodes a HPPD according to the invention, a nucleic acid sequence which encodes a plant transit peptide, with this sequence being arranged between the promoter region and the sequence encoding the HPPD according to the invention so as to permit expression of a transit peptide/HPPD fusion protein.

In a further particular embodiment, the present invention relates to the use of HPPD inhibitor herbicides on plants, plant parts, or plant seeds comprising HPPD tolerant gene according to the invention, or to the use of HPPD inhibitor herbicides on soil where such plants, plant parts or seeds are to be grown or sown, either alone or in combination with one or more other known herbicides acting in a different matter to HPPD inhibitors. In a more particular embodiment, the employed HPPD inhibitor herbicide is selected from the group consisting of triketones (named triketone HPPD inhibitor), such as tembotrione, sulcotrione mesotrione, bicyclopyrone, tefuryltrione, particularly tembotrione, of the class diketone such as diketonitrile of the class of isoxazoles such as isoxaflutole or of the class of pyrazolinates (named pyrazolinate HPPD inhibitor), such as pyrasulfotole, pyrazolate, topramezone, benzofenap, even more specifically present invention relates to the application of tembotrione, mesotrione, diketonitrile, bicyclopyrone, tefuryltrione, benzofenap, pyrasulfotole, pyrazolate and sulcotrione to such HPPD inhibitor tolerant plants, plant parts or plant seeds.

As a regulatory sequence which functions as a promoter in plant cells and plants, use may be made of any promoter sequence of a gene which is naturally expressed in plants, in particular a promoter which is expressed especially in the leaves of plants, such as for example "constitutive" promoters of bacterial, viral or plant origin, or "light-dependent" promoters, such as that of a plant ribulose-biscarboxylase/oxygenase (RuBisCO) small subunit gene, or any suitable known promoter-expressible which may be used. Among the promoters of plant origin, mention will be made of the histone promoters as described in EP 0 507 698 A1, the rice actin promoter (U.S. Pat. No. 5,641,876), or a plant ubiquitin promoter (U.S. Pat. No. 5,510,474). Among the promoters of a plant virus gene, mention will be made of that of the cauliflower mosaic virus (CaMV 19S or 35S, Sanders et al. (1987), Nucleic Acids Res. 15(4):1543-58), the circovirus (AU 689 311) or the Cassava vein mosaic virus (CsVMV, U.S. Pat. No. 7,053,205).

In one embodiment of this invention, a promoter sequence specific for particular regions or tissues of plants can be used to express the HPPD proteins of the invention, such as promoters specific for seeds (Datla, R. et al., 1997, Biotechnology Ann. Rev. 3, 269-296), especially the napin promoter (EP 255 378 A1), the phaseolin promoter, the glutenin promoter, the helianthinin promoter (WO 92/17580), the albumin promoter (WO 98/45460), the oleosin promoter (WO 98/45461), the SAT1 promoter or the SAT3 promoter (PCT/US98/06978).

Use may also be made of an inducible promoter advantageously chosen from the phenylalanine ammonia lyase (PAL), HMG-CoA reductase (HMG), chitinase, glucanase, proteinase inhibitor (PI), PR1 family gene, nopaline synthase (nos) and vspB promoters (U.S. Pat. No. 5,670,349, Table 3), the HMG2 promoter (U.S. Pat. No. 5,670,349), the apple beta-galactosidase (ABG1) promoter and the apple aminocyclopropane carboxylate synthase (ACC synthase) promoter (WO 98/45445).

According to the invention, use may also be made, in combination with the promoter, of other regulatory sequences, which are located between the promoter and the coding sequence, such as transcription activators ("enhancers"), for instance the translation activator of the tobacco mosaic virus (TMV) described in Application WO 87/07644, or of the tobacco etch virus (TEV) described by Carrington & Freed 1990, J. Virol. 64: 1590-1597, for example, or introns such as the adh1 intron of maize or intron 1 of rice actin.

In a further particular embodiment, the gene of the invention is present in plants in multiple, preferably two copies, each of these controlled by a different plant expressible promoter.

In a further particular embodiment, the chimeric gene of the invention can be combined with any further chimeric gene coding for an HPPD protein, preferably these different genes are controlled by different regulatory elements being active in plants.

In a further particular embodiment, the chimeric gene of the invention can be combined with a CYP450 Maize monooxygenase (nsf1 gene) gene being under the control of an identical or different plant expressible promoter.

As a regulatory terminator or polyadenylation sequence, use may be made of any corresponding sequence of bacterial origin, such as for example the nos terminator of *Agrobacterium tumefaciens*, of viral origin, such as for example the CaMV 35S terminator, or of plant origin, such as for example a histone terminator as described in published Patent Application EP 0 633 317 A1.

The term "gene", as used herein refers to a DNA coding region flanked by 5' and/or 3' regulatory sequences allowing a RNA to be transcribed which can be translated to a protein, typically comprising at least a promoter region. A "chimeric gene", when referring to an HPPD encoding DNA of this invention, refers to an HPPD encoding DNA sequence having 5' and/or 3' regulatory sequences different from the naturally occurring protist 5' and/or 3' regulatory sequences which drive the expression of the HPPD protein in its native host cell (also referred to as "heterologous promoter" or "heterologous regulatory sequences").

The terms "DNA/protein comprising the sequence X" and "DNA/protein with the sequence comprising sequence X", as used herein, refer to a DNA or protein including or containing at least the sequence X in their nucleotide or amino acid sequence, so that other nucleotide or amino acid sequences can be included at the 5' (or N-terminal) and/or 3' (or C-terminal) end, e.g., a N-terminal transit or signal peptide. The term "comprising", as used herein, is open-ended language in the meaning of "including", meaning that other elements then those specifically recited can also be present. The term "consisting of", as used herein, is closed-ended language, i.e., only those elements specifically recited are present. The term "DNA encoding a protein comprising sequence X", as used herein, refers to a DNA comprising a coding sequence which after transcription and translation results in a protein containing at least amino acid sequence X. A DNA encoding a protein need not be a naturally occurring DNA, and can be a semi-synthetic, fully synthetic or artificial DNA and can include introns and 5' and/or 3' flanking regions. The term "nucleotide sequence", as used herein, refers to the sequence of a DNA or RNA molecule, which can be in single- or double-stranded form.

HPPD proteins according to the invention may be equipped with a signal peptide according to procedures known in the art, see, e.g., published PCT patent application WO 96/10083, or they can be replaced by another peptide such as a chloroplast transit peptide (e.g., Van Den Broeck et al., 1985, Nature 313, 358, or a modified chloroplast transit peptide of U.S. Pat. No. 5,510,471) causing transport of the protein to the chloroplasts, by a secretory signal peptide or a peptide targeting the protein to other plastids, mitochondria, the ER, or another organelle, or it can be replaced by a methionine amino acid or by a methionine-alanine dipeptide. Signal sequences for targeting to intracellular organelles or for secretion outside the plant cell or to the cell wall are found in naturally targeted or secreted proteins, preferably those described by Klösgen et al. (1989, Mol. Gen. Genet. 217, 155-161), Klösgen and Weil (1991, Mol. Gen. Genet. 225, 297-304), Neuhaus & Rogers (1998, Plant Mol. Biol. 38, 127-144), Bih et al. (1999, J. Biol. Chem. 274, 22884-22894), Morris et al. (1999, Biochem. Biophys. Res. Commun. 255, 328-333), Hesse et al. (1989, EMBO J. 8 2453-2461), Tavladoraki et al. (1998, FEBS Lett. 426, 62-66), Terashima et al. (1999, Appl. Microbiol. Biotechnol. 52, 516-523), Park et al. (1997, J. Biol. Chem. 272, 6876-6881), Shcherban et al. (1995, Proc. Natl. Acad. Sci. USA 92, 9245-9249), all of which are incorporated herein by reference, particularly the signal peptide sequences from targeted or secreted proteins of corn, cotton, soybean, or rice. A DNA sequence encoding such a plant signal peptide can be inserted in the chimeric gene encoding the HPPD protein for expression in plants.

Unless otherwise stated in the examples, all procedures for making and manipulating recombinant DNA are carried out by the standard procedures described in Sambrook et al., Molecular Cloning—A Laboratory Manual, Second Ed., Cold Spring Harbor Laboratory Press, NY (1989), and in Volumes 1 and 2 of Ausubel et al. (1994) Current Protocols in Molecular Biology, Current Protocols, USA. Standard materials and methods for plant molecular biology work are described in Plant Molecular Biology Labfax (1993) by R. R. D. Croy, jointly published by BIOS Scientific Publications Ltd (UK) and Blackwell Scientific Publications (UK). Procedures for PCR technology can be found in "PCR protocols: a guide to methods and applications", Edited by M. A. Innis, D. H. Gelfand, J. J. Sninsky and T. J. White (Academic Press, Inc., 1990).

The terms "tolerance", "tolerant" or "less sensitive" are interchangeable used and mean the relative levels of inherent tolerance of the HPPD screened according to a visible indicator phenotype of the strain or plant transformed with a nucleic acid comprising the gene coding for the respective HPPD protein in the presence of different concentrations of the various HPPD inhibitors. Dose responses and relative shifts in dose responses associated with these indicator phenotypes (formation of brown colour, growth inhibition, bleaching, herbicidal effect etc) are conveniently expressed in terms, for example, of GR50 (concentration for 50% reduction of growth) or MIC (minimum inhibitory concentration) values where increases in values correspond to increases in inherent tolerance of the expressed HPPD, in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance of the expressed HPPD. Herbicides can suitably be applied pre-emergence or post emergence.

Likewise, tolerance level of the nucleic acid or gene encoding an HPPD protein according to the invention, or the HPPD protein of the invention is screened via transgenesis, regeneration, breeding and spray testing of a test plant such as tobacco, or a crop plant such as soybean or cotton and according to these results, such plants are at least 2-4× more tolerant to HPPD inhibitors like tembotrione, mesotrione, diketonitrile and/or bicyclopyrone, than plants that do not contain any exogenous gene encoding an HPPD protein, or than plants that contain a gene comprising an *Arabidopsis thaliana* HPPD-encoding DNA, under control of the same promoter as the HPPD DNA of the invention.

"Host organism" or "host" is understood as being any unicellular or multicellular heterologous organism into which the nucleic acid or chimeric gene according to the invention can be introduced for the purpose of producing HPPD according to the invention. These organisms are, in particular, bacteria, for example *E. coli*, yeasts, in particular of the genera *Saccharomyces* or *Kluyveromyces, Pichia*, fungi, in particular *Aspergillus*, a baculovirus or, preferably, plant cells and plants.

"Plant cell" is understood, according to the invention, as being any cell which is derived from or found in a plant and which is able to form or is part of undifferentiated tissues, such as calli, differentiated tissues such as embryos, parts of plants, plants or seeds. This includes protoplasts and pollen, cultivated plants cells or protoplasts grown in vitro, and plant cells that can regenerate into a complete plant.

"Plant" is understood, according to the invention, as being any differentiated multicellular organism which is capable of photosynthesis, in particular a monocotyledonous or dicotyledonous organism, more especially cultivated plants which are or are not intended for animal or human nutrition, such as maize or corn, wheat, *Brassica* spp. plants such as *Brassica napus* or *Brassica juncea*, soya spp, rice, sugarcane, beetroot, tobacco, cotton, vegetable plants such as cucumber, leek, carrot, tomato, lettuce, peppers, melon, watermelon, etc. Transgenic plants, as used herein, refer to plants comprising a foreign or heterologous gene stably inserted in their genome.

In one embodiment the invention relates to the transformation of plants. Any promoter sequence of a gene which is expressed naturally in plants, or any hybrid or combination of promoter elements of genes expressed naturally in plants, including *Agrobacterium* or plant virus promoters, or any promoter which is suitable for controlling the transcription of a herbicide tolerance gene in plants, can be used as the promoter sequence in the plants of the invention (named "plant-expressible promoter" herein). Examples of such suitable plant-expressible promoters are described above. In one embodiment of this invention, such plant-expressible promoters are operably-linked to a coding sequence encoding an HPPD protein of the invention to form a chimeric HPPD gene of this invention.

According to the invention, it is also possible to use, in combination with the promoter regulatory sequence, other regulatory sequences which are located between the promoter and the coding sequence, such as intron sequences, or transcription activators (enhancers). Examples of such suitable regulatory sequences are described above.

Any corresponding sequence of bacterial or viral origin, such as the nos terminator from *Agrobacterium tumefaciens*, or of plant origin, such as a histone terminator as described in application EP 0 633 317 A1, may be used as transcription termination (and polyadenylation) regulatory sequence.

In one particular embodiment of the invention, a nucleic acid sequence which encodes a transit peptide is employed 5' (upstream) of the nucleic acid sequence encoding the exogenous HPPD according to the invention, with this transit peptide sequence being arranged between the promoter region and the sequence encoding the exogenous HPPD so as to permit expression of a transit peptide-HPPD fusion protein, such as the protein of SEQ ID No. 6 or SEQ ID No. 7. The transit peptide makes it possible to direct the HPPD into the plastids, more especially the chloroplasts, with the fusion protein being cleaved between the transit peptide and the HPPD protein of the invention when the latter enters the plastid. The transit peptide may be a single peptide, such as an EPSPS transit peptide (described in U.S. Pat. No. 5,188,642) or a transit peptide of the plant ribulose bisphosphate carboxylase/oxygenase small subunit (RuBisCO ssu), where appropriate, including a few amino acids of the N-terminal part of the mature RuBisCO ssu (EP 189 707 A1), or else may be a fusion of several transit peptides such as a transit peptide which comprises a first plant transit peptide which is fused to a part of the N-terminal sequence of a mature protein having a plastid location, with this part in turn being fused to a second plant transit peptide as described in patent EP 508 909 A1, and, more especially, the optimized transit peptide which comprises a transit peptide of the sunflower RuBisCO ssu fused to 22 amino acids of the N-terminal end of the maize RuBisCO ssu, in turn fused to the transit peptide of the maize RuBisCO ssu, as described, with its coding sequence, in patent EP 508 909 A1.

The present invention also relates to the transit peptide-HPPD fusion protein and a nucleic acid or plant-expressible chimeric gene encoding such fusion protein, wherein the two elements of this fusion protein are as defined above.

The present invention also relates to a cloning, transformation and/or expression vector, which vector contains at least one chimeric gene as defined above. In addition to the above chimeric gene, this vector can contain an origin of replication. This vector can be a plasmid or plasmid portion, a cosmid, or a bacteriophage or a virus which has been transformed by introducing the chimeric gene according to the invention. Transformation vectors are well known to the skilled person and widely described in the literature. The transformation vector which can be used, in particular, for transforming plant cells or plants may be a virus, which can be employed for transforming plant cells or plants and which additionally contains its own replication and expression elements. According to the invention, the vector for transforming plant cells or plants is preferably a plasmid, such as a disarmed *Agrobacterium* Ti plasmid.

The present invention also relates to the host organisms, in particular plant cells, seeds or plants, which comprise a chimeric gene which comprises a sequence encoding an HPPD protein of the invention, such as a protein comprising the amino acid sequence of SEQ ID Nos 4, 5, 6, or 7 as defined above, and the use of the plants or seeds of the invention in a field to grow a crop and harvest a plant product, e.g., soya spp, rice, wheat, barley or corn grains or cotton bolls, where in one embodiment said use involves the application of an HPPD inhibitor herbicide to such plants to control weeds. In one embodiment of this invention, in such use the HPPD inhibitors are triketones or pyrazolinates, preferably tembotrione, mesotrione, topramezone or sulcotrione, bicyclopyrone, pyrasulfotole, pyrazolate, benzofenap and tefuryltrione, particularly tembotrione.

Therefore, the present invention relates to a host organism, in particular a plant cell, seed, or plant, characterized in that it contains at least one HPPD chimeric gene as described above, or at least an HPPD nucleic acid sequence as previously described.

In a particular embodiment, the present invention relates to a plant cell or plant characterized in that it contains at least a nucleic acid sequence which encodes an HPPD protein of this invention which retain its properties of catalysing the conversion of para-hydroxyphenylpyruvate to homogentisate and which makes this plant more tolerant than plants of the same species not comprising such HPPD protein of the present invention, particularly to triketones, or pyrazolinates, preferably tembotrione, mesotrione, topramezone or sulcotrione, bicyclopyrone, pyrasulfotole, pyrazolate, benzofenap and tefuryltrione, particularly tembotrione and such plants containing the HPPD of the invention have an agronomically acceptable tolerance to an HPPD inhibitor herbicide particularly to triketones, or pyrazolinates, preferably tembotrione, mesotrione, topramezone or sulcotrione, bicyclopyrone, pyrasulfotole, pyrazolate, benzofenap and tefuryltrione, particularly tembotrione.

In another particular embodiment, the present invention relates to a plant cell or plant characterized in that it contains at least a nucleic acid sequence which encodes an HPPD of this invention which retain its properties of catalysing the conversion of para-hydroxyphenylpyruvate to homogentisate and which is less sensitive to an HPPD inhibitor than the host plant endogenous HPPD, such as the HPPD from *Arabidopsis thaliana*, particularly the HPPD comprising the amino acid sequence of SEQ ID No. 11 (from the amino acid position 126 to the amino acid position 568), or comprising the amino acid sequence of SEQ ID No. 11 or SEQ ID No. 12 (from the amino acid position 134 to the amino acid position 575).

In a particular embodiment, the present invention relates to a host plant cell, seed or host plant characterized in that it contains at least a nucleic acid sequence which encodes an HPPD of the invention as defined herein, wherein the HPPD of the invention is less sensitive than the host plant endogenous HPPD to an HPPD inhibitor herbicide of the class of isoxazoles, diketonitriles, triketones or pyrazolinates more especially from isoxaflutole, tembotrione, mesotrione, sulcotrione, pyrasulfotole, bicyclopyrone, tefuryltrione, topramezone, 2-cyano-3-cyclopropyl-1-(2-$SO_2CH_3$-4-$CF_3$-phenyl)propane-1,3-dione and 2-cyano-3-cyclopropyl-1-(2-$SO_2CH_3$-4-2,3 $Cl_2$ phenyl)propane-1,3-dione, even more particularly tembotrione, mesotrione, diketonitrile, bicyclopyrone, topramezone, pyrazolate, benzofenap, sulcotrione, tefuryltrione, and pyrasulfotole, most particularly tembotrione, mesotrione and bicyclopyrone.

In another particular embodiment, the present invention relates to a plant cell or plant characterized in that it contains at least a nucleic acid sequence encoding an HPPD of the invention as previously described, and in addition a chimeric gene comprising a plant-expressible promoter as described above, operably-linked to a nucleic acid sequence encoding a PDH (prephenate dehydrogenase) enzyme (US 2005/0257283).

The present invention also relates to the plants which contain transformed cells, in particular the plants which are regenerated from the transformed cells, and progeny plants or seeds thereof, comprising the chimeric HPPD gene of the invention. The regeneration can be obtained by any appropriate method, with the method depending on the nature of the species, as described, for example, in the above references. The following patents and patent applications may be cited, in particular, with regard to the methods for transforming plant cells and regenerating plants: U.S. Pat. No. 4,459,355, U.S. Pat. No. 4,536,475, U.S. Pat. No. 5,464,763, U.S. Pat. No. 5,177,010, U.S. Pat. No. 5,187,073, EP 267,159 A1, EP 604 662 A1, EP 672 752 A1, U.S. Pat. No. 4,945,050, U.S. Pat. No. 5,036,006, U.S. Pat. No. 5,100,792, U.S. Pat. No. 5,371,014, U.S. Pat. No. 5,478,744, U.S. Pat. No. 5,179,022, U.S. Pat. No. 5,565,346, U.S. Pat. No. 5,484,956, U.S. Pat. No. 5,508,468, U.S. Pat. No. 5,538,877, U.S. Pat. No. 5,554,798, U.S. Pat. No. 5,489,520, U.S. Pat. No. 5,510,318, U.S. Pat. No. 5,204,253, U.S. Pat. No. 5,405,765, EP 442 174 A1, EP 486 233 A1, EP 486 234 A1, EP 539 563 A1, EP 674 725 A1, WO 91/02071 and WO 95/06128.

The present invention also relates to the transgenic plants or part thereof, which are derived by cultivating and/or crossing the above transgenic plants, and to the seeds of the transgenic plants, comprising the HPPD chimeric gene of the invention.

The present invention also relates to the end products such as the meal or oil which are obtained from the plants, part thereof, or seeds of the invention.

The transformed plants which can be obtained in accordance with the invention can be of the monocotyledonous type, such as wheat, barley, sugarcane, rice, onion, and corn or maize, or of the dicotyledonous type, such as tobacco, soya spp, alfalfa *Brassica* spp. plants such as oilseed rape, cotton, sugarbeet clover, vegetables, etc.

The invention relates to a method for transforming host organisms, in particular plant cells or plants, by integrating in such organisms at least one nucleic acid sequence or one chimeric gene as previously defined, wherein it is possible to obtain the transformation by any appropriate known means, which means are amply described in the specialist literature and, in particular, the references cited in the present application, e.g., by using the vector according to the invention.

One transformation method in accordance with this invention comprises bombarding cells, protoplasts or tissues with solid or liquid particles to which DNA is attached, or containing DNA. Another transformation method comprises using, as mean for transfer into the plant, a chimeric gene which is inserted into an *Agrobacterium tumefaciens* Ti plasmid or an *Agrobacterium rhizogenes* Ri plasmid. Other methods may be used, such as microinjection or electroporation or otherwise direct gene transfer using PEG. The skilled person can select any appropriate method for transforming the host organism of choice, in particular the plant cell or the plant. As examples, the technology for soybean transformation has been extensively described in the examples 1 to 3 disclosed in EP 1186666 A1, incorporated herein by reference. For rice, *Agrobacterium*-mediated transformation (Hiei et al., 1994 Plant J 6:271-282, and Hiei et al., 1997 Plant Mol. Biol. 35:205-21, incorporated herein by reference), electroporation (U.S. Pat. No. 5,641,664 and U.S. Pat. No. 5,679,558, incorporated herein by reference), or bombardment (Christou et al., 1991, Biotechnology 9:957 incorporated herein by reference) could be performed. A suitable technology for transformation of monocotyledonous plants, and particularly rice, is described in WO 92/09696, incorporated herein by reference. For cotton, *Agrobacterium*-mediated transformation (Gould J. H. and Magallanes-Cedeno M., 1998 Plant Molecular Biology reporter, 16:1-10 and Zapata C., 1999, Theoretical Applied Genetics, 98(2):1432-2242 incorporated herein by reference), polybrene and/or treatment-mediated transformation (Sawahel W. A., 2001, —Plant Molecular Biology reporter, 19:377a-377f, incorporated herein by reference) have been described.

In a particular embodiment of the invention, the HPPD of the invention is targeted into the chloroplast. This may be done by fusing a nucleic acid sequence which encodes a transit peptide to the nucleic acid sequence encoding the HPPD protein of the invention to obtain a nucleic acid encoding a fusion protein as described above. Alternatively, the HPPD of the invention may be expressed directly in the plastids, such as the chloroplasts, using transformation of the plastid, such as the chloroplast genome. A suitable method comprises the bombardment of plant cells or tissue by solid particles coated with the DNA or liquid particles comprising the DNA, and integration of the introduced gene encoding the protein of the invention by homologous recombination. Suitable vectors and selection systems are known to the person skilled in the art. An example of means and methods which can be used for such integration into the chloroplast genome of tobacco plants is given in WO 06/108830, the content of which is hereby incorporated by reference The present invention also relates to a method for obtaining a plant to an HPPD inhibitor, characterized in that the plant is transformed with a chimeric HPPD gene of the invention as previously described.

Therefore, the present invention also relates to a method for obtaining a plant tolerant to an HPPD inhibitor, characterized in that the plant contains a chimeric HPPD gene of the invention which comprises a coding sequence as well as a heterologous regulatory element in the 5' and optionally in the 3' positions, which are able to function in a host organism, characterized in that the coding sequence comprises at least a nucleic acid sequence defining a gene encoding an HPPD of the invention as previously described.

In one embodiment of this invention, the HPPD inhibitor in the above method is a triketone or pyrazolinate herbicide, preferably tembotrione, mesotrione, bicyclopyrone, tefuryltrione pyrasulfotole, pyrazolate, diketonitrile, benzofenap, or sulcotrione, particularly tembotrione.

According to this invention, a method for obtaining a plant tolerant to an HPPD inhibitor as described above is also provided, characterized in that a plant is obtained comprising a first transgene which is a chimeric HPPD gene of the invention, and a second transgene, which is a chimeric gene comprising a plant-expressible promoter operably-linked to a nucleic acid encoding a PDH (prephenate dehydrogenase) enzyme. A plant comprising such two transgenes can be obtained by transforming a plant with one transgene, and then re-transforming this transgenic plant with the second transgene, or by transforming a plant with the two transgenes simultaneously (in the same or in 2 different transforming DNAs or vectors), or by crossing a plant comprising the first transgene with a plant comprising the second transgene, as is well known in the art.

The invention also relates to a method for selectively removing weeds or preventing the germination of weeds in a field to be planted with plants or to be sown with seeds, or in a plant crop, by application of an HPPD inhibitor to such field or plant crop, in particular an HPPD inhibitor herbicide as previously defined, which method is characterized in that this HPPD inhibitor herbicide is applied to plants which have been transformed in accordance with the invention, either before sowing the crop (hereinafter named pre-planting application), before emergence of the crop (hereinafter named pre-emergence application), or after emergence of the crop (hereinafter named post-emergence application).

The invention also relates to a method for controlling in an area or a field which contains transformed seeds as previously described in the present invention, which method comprises applying, to the said area of the field, a dose of an HPPD inhibitor herbicide which is toxic for the said weeds, without significantly affecting the seeds or plants which contain the HPPD nucleic acid or the chimeric HPPD gene of the invention as previously described in the present invention.

The present invention also relates to a method for cultivating the plants which have been transformed with a chimeric gene according to the invention, which method comprises planting seeds comprising a chimeric gene of the invention, in an area of a field which is appropriate for cultivating the said plants, and in applying, if weeds are present, a dose, which is toxic for the weeds, of a herbicide whose target is the above-defined HPPD to the said area of the said field, without significantly affecting the said transformed seeds or the said transformed plants, and in then harvesting the cultivated plants or plant parts when they reach the desired stage of maturity and, where appropriate, in separating the seeds from the harvested plants.

In the above methods, the herbicide whose target is the HPPD enzyme can be applied in accordance with the invention, either before sowing the crop, before the crop emerges or after the crop emerges.

The present invention also relates to a process for obtaining oil, particularly soya spp, corn or cotton oil, or meal, comprising growing a crop, particularly a soya spp crop, expressing an HPPD protein of the invention optionally treating such crop with an HPPD inhibitor herbicide, harvesting the grains and milling the grains to make meal and extract the oil. Also the seeds or grains, either whole, broken or crushed, comprising the chimeric gene of the invention are part of this invention.

Therefore, the present invention relates to a method for obtaining oil or meal comprising growing a transformed plant as described above, optionally treating such plant with an HPPD inhibitor herbicide, harvesting the grains and milling the grains to make meal and extract the oil.

Further provided in this invention, are the above methods involving an HPPD inhibitor herbicide selected from isoxaflutole, tembotrione, mesotrione, pyrasulfotole, sulcotrione, bicyclopyrone, tefuryltrione, topramezone, 2-cyano-3-cyclopropyl-1-(2-methylsulphonyl-4-trifluoromethylphenyl)-propane-1,3-dione and to 2-cyano-1-[4-(methylsulphonyl)-2-trifluoromethylphenyl]-3-(1-methylcyclopropyl)propane-1,3-dione.

Also provided herein are the above methods of the invention involving an HPPD inhibitor herbicide of the class of triketones, such as tembotrione, sulcotrione and mesotrione, or of the class of pyrazolinates, such as pyrasulfotole and topramezone, particularly selected from tembotrione, sulcotrione, topramezone, bicyclopyrone, tefuryltrione and mesotrione, more particularly tembotrione.

Within the meaning of the present invention, "herbicide" is understood as being a herbicidally active substance on its own or such a substance which is combined with an additive which alters its efficacy, such as, for example, an agent which increases its activity (a synergistic agent) or which limits its activity (a safener). It is of course to be understood that, for their application in practice, the above herbicides are combined, in a manner which is known per se, with the formulation adjuvants which are customarily employed in agricultural chemistry.

HPPD inhibitor herbicides like those of the class of triketones, such as tembotrione, sulcotrione and mesotrione, or of the class of pyrazolinates, such as pyrasulfotole and topramezone, particularly selected from tembotrione, sulcotrione, topramezone, bicyclopyrone, tefuryltrione and mesotrione, more particularly tembotrione, have an outstanding herbicidal activity against a broad spectrum of economically important monocotyledonous and dicotyledonous annual harmful plants. The active substances also act efficiently on perennial harmful plants which produce shoots from rhizomes, wood stocks or other perennial organs and which are difficult to control.

The present invention therefore also relates to a method of controlling undesired plants or for regulating the growth of plants in crops of plants comprising an HPPD according to the invention, where one or more HPPD inhibitor herbicides of the class of triketones, such as tembotrione, sulcotrione and mesotrione, or of the class of pyrazolinates, such as pyrasulfotole and topramezone, particularly selected from tembotrione, sulcotrione, topramezone, bicyclopyrone, tefuryltrione and mesotrione, more particularly tembotrione are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, an HPPD inhibitor herbicide of the class of triketones, such as tembotrione, sulcotrione and mesotrione, or of the class of pyrazolinates, such as pyrasulfotole and topramezone, particularly selected from tembotrione, sulcotrione, topramezone, bicyclopyrone, tefuryltrione and mesotrione, more particularly tembotrione can be applied for example pre-planting (if appropriate also by incorporation into the soil), pre-emergence or post-emergence. Examples of individual representatives of the monocotyledonous and dicotyledonous weeds which can be controlled with an HPPD inhibitor herbicide of the class of triketones, such as tembotrione, sulcotrione and mesotrione, or of the class of pyrazolinates, such as pyrasulfotole and topramezone, particularly selected from tembotrione, sulcotrione, topramezone, bicyclopyrone, tefuryltrione and mesotrione, more particularly tembotrione are hereby mentioned, without this mentioning being intended as a limitation to certain species only:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

In transgenic crops according to the invention, comprising an HPPD protein, DNA or chimeric gene according invention and which may also show one more further herbicide resistances against herbicides that differ from HPPD inhibitor herbicides, the use of HPPD inhibitor herbicide of the class of triketones, such as tembotrione, sulcotrione and mesotrione, or of the class of pyrazolinates, such as pyrasulfotole and topramezone, particularly selected from tembotrione, sulcotrione, topramezone, bicyclopyrone, tefuryltrione and mesotrione, more particularly tembotrione in economically important transgenic crops of useful plants and ornamentals, for example of cereals such as wheat, barley, rye, oats, sorghum and millet, rice and maize or else crops of sugar beet, cotton, soya spp, oil seed rape, potato, tomato, peas and other vegetables is preferred.

As it relates to plant properties other than the tolerance to HPPD inhibitor herbicides as described in the present invention, conventional ways of generating novel plants which, in comparison with existing plants, have modified properties are, for example, traditional breeding methods and the generation of mutants. Alternatively, novel plants with modified properties can be generated with the aid of recombinant methods (see, for example, EP-A-0221044 A1, EP-A-0131624 A1). For example, the following have been described in several cases:

recombinant modifications of crop plants for the purposes of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or of the glyphosate type (WO 92/00377) or of the sulfonylurea type (EP-A-0257993, U.S. Pat. No. 5,013,659), transgenic crop plants, for example corn, cotton or soya spp, which are capable of producing *Bacillus thuringiensis* toxins (Bt toxins), or hybrids or mutants thereof, which make the plants resistant to certain pests (EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination of novel properties such as a combination of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431).

To carry out such recombinant manipulations, it is possible to introduce nucleic acid molecules into plasmids, which permit a mutagenesis or sequence modification by recombination of DNA sequences. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2. ed., Cold Spring Harbor Laboratory Press, Cold Spring Harbor, N.Y.; or Winnacker "Gene and Klone", VCH Weinheim 2. ed., 1996

The generation of plant cells with a reduced activity for a gene product can be achieved for example by the expression of at least one corresponding antisense RNA, a sense RNA for achieving a cosuppression effect, or a combination of both an antisense and sense RNA forming a double-stranded silencing RNA molecule (RNAi), or by the expression of at least one correspondingly constructed ribozyme, which specifically cleaves transcripts of the abovementioned gene product. To do this, it is possible firstly to use DNA molecules which comprise all of the coding sequence of a gene product, including any flanking sequences which may be present, or else DNA molecules which only comprise parts of the coding sequence, it being necessary for these parts to be long enough to bring about an antisense effect in the cells. It is also possible to use DNA sequences which have a high degree of homology with the coding sequences of a gene product, but which are not entirely identical.

When expressing nucleic acid molecules in plants, the obtained protein may be localized in any compartment of the plant cell. In order to achieve localization in a particular compartment, however, it is possible for example to link the coding region to DNA sequences which ensure the localization in a specific compartment. Such sequences are known to the skilled person (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). However, the nucleic acid molecules can also be expressed in the organelles of the plant cells.

The transgenic plant cells can be regenerated by known techniques to give intact plants. In principle, the transgenic plants may be plants of any plant species, including monocotyledonous or dicotyledonous plants.

Thus, transgenic plants can be obtained which—in addition to the chimeric HPPD gene of the invention—have modified properties as the result of overexpression, suppression or inhibition of homologous (=natural) genes or gene sequences or expression of heterologous (=foreign) genes or gene sequences.

On the plants, plant cells or seeds of the invention, it is preferred to employ the HPPD inhibitor herbicide of the class of triketones, such as tembotrione, sulcotrione and mesotrione, or of the class of pyrazolinates, such as pyrasulfotole and topramezone, particularly selected from tembotrione, sulcotrione, topramezone, bicyclopyrone, tefuryltrione and mesotrione, more particularly tembotrione in transgenic crops which are also resistant to growth regulators such as, for example, 2,4-D or dicamba, or against herbicides which inhibit essential plant enzymes, for example acetolactate synthases (ALS), EPSP synthases, or glutamine synthases (GS), or against herbicides from the group of the sulfonylureas, glyphosate, or glufosinate and analogous active substances.

The invention therefore also relates to the use of herbicides applied to this HPPD tolerant plants according to the invention for controlling harmful plants (i.e. weeds) which also extends to transgenic crop plants comprising a second or more herbicide resistance(s) beside the resistance against HPPD inhibitor herbicide of the class of triketones, such as tembotrione, sulcotrione and mesotrione, of the class of isoxazoles such as isoxaflutole or of the class of pyrazolinates, such as pyrasulfotole and topramezone, particularly selected from tembotrione, sulcotrione, topramezone, bicyclopyrone, tefuryltrione and mesotrione, more particularly tembotrione.

HPPD inhibitor herbicide of the class of triketones, such as tembotrione, sulcotrione and mesotrione, or of the class of pyrazolinates, such as pyrasulfotole and topramezone, particularly selected from tembotrione, sulcotrione, topramezone, bicyclopyrone, tefuryltrione and mesotrione, more particularly tembotrione can be employed in the customary preparations in the form of wettable powders, emulsifiable concentrates, sprayable solutions, dusts or granules.

HPPD inhibitor herbicide of the class of triketones, such as tembotrione, sulcotrione and mesotrione, or of the class of pyrazolinates, such as pyrasulfotole and topramezone, particularly selected from tembotrione, sulcotrione, topramezone, bicyclopyrone, tefuryltrione and mesotrione, more particularly tembotrione can be formulated in various ways, depending on the prevailing biological and/or physicochemical parameters. Examples of possible formulations are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for application by broadcasting and on the soil, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical technology], volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are also known and are described, for example, in: Watkins, "Handbook of Insecticide Dust Diluents and Carriers", 2nd Ed., Darland Books, Caldwell N. J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie" [Chemical technology], volume 7, C. Hanser Verlag Munich, 4th Ed. 1986.

Based on these formulations, it is also possible to prepare combinations with other pesticidally active substances such as, for example, insecticides, acaricides, herbicides, fungicides, and with safeners, fertilizers and/or growth regulators, for example in the form of a ready mix or a tank mix.

Wettable powders are preparations which are uniformly dispersible in water and which, besides the active substance, also comprise ionic and/or nonionic surfactants (wetters, dispersers), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, besides a diluent or inert substance. To prepare the wettable powders, the herbicidally active substances are ground finely, for example in customary apparatuses such as hammer mills, blower mills and air-jet mills, and mixed with the formulation auxiliaries, either simultaneously or subsequently.

Emulsifiable concentrates are prepared by dissolving the active substance in an organic solvent, for example butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylarylpolyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials such as, for example, talcum, natural clays such as kaolin, bentonite and pyrophyllite, or diatomaceous earth.

Suspension concentrates can be water- or oil-based. They can be prepared for example by wet-grinding by means of commercially available bead mills, if appropriate with addition of surfactants as already listed above for example in the case of the other formulation types.

Emulsions, for example oil-in-water emulsions (EW), can be prepared for example by means of stirrers, colloid mills and/or static mixers using aqueous organic solvents and, if appropriate, surfactants, as have already been mentioned for example above for the other formulation types.

Granules can be prepared either by spraying the active substance onto adsorptive, granulated inert material, or by applying active substance concentrates to the surface of carriers such as sand, kaolinites or granulated inert material with the aid of stickers, for example polyvinyl alcohol, sodium polyacrylate or else mineral oils. Suitable active substances can also be granulated in the manner which is customary for the production of fertilizer granules, if desired as a mixture with fertilizers.

Water-dispersible granules are generally prepared by customary methods such as spray drying, fluidized-bed granulation, disk granulation, mixing with high-speed stirrers, and extrusion without solid inert material.

To prepare disk granules, fluidized-bed granules, extruder granules and spray granules, see, for example, methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57.

For further details of the formulation of crop protection products see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise from 0.1 to 99% by weight, in particular from 0.1 to 95% by weight, of compounds according to the invention. In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise from 1 to 30% by weight of active substance, preferably in most cases from 5 to 20% by weight of active substance, and sprayable solutions comprise approximately from 0.05 to 80, preferably from 2 to 50% by weight of active substance. In the case of water-dispersible granules, the active substance content depends partly on whether the active compound is in liquid or solid form, and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the auxiliaries which are conventional in each case, such as stickers, wetters, dispersants, emulsifiers, penetrations, preservatives, antifreeze agents, solvents, fillers, carriers, colorants, antifoams, evaporation inhibitors, and pH and viscosity regulators.

Based on these formulations, it is also possible to prepare combinations of an HPPD inhibitor herbicide of the class of triketones, such as tembotrione, sulcotrione and mesotrione, or of the class of pyrazolinates, such as pyrasulfotole and topramezone, particularly selected from tembotrione, sulcotrione, topramezone, bicyclopyrone, tefuryltrione and mesotrione, more particularly tembotrione with other pesticidally active substances such as, for example, insecticides, acaricides, herbicides, fungicides, and with safeners, fertilizers and/or growth regulators, for example in the form of a ready mix or a tank mix to be applied to HPPD tolerant plants according to the invention.

Active substances which can be applied to HPPD tolerant plants according to the present invention in combination with HPPD inhibitor herbicide of the class of triketones, such as tembotrione, sulcotrione and mesotrione, or of the class of pyrazolinates, such as pyrasulfotole and topramezone, particularly selected from tembotrione, sulcotrione, topramezone, bicyclopyrone, tefuryltrione and mesotrione, more particularly tembotrione in mixed formulations or in the tank mix are, for example, known active substances which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as are described in, for example, Weed Research 26 (1986) 441-445 or "The Pesticide Manual", 14th edition, The British Crop Protection Council and the Royal Soc. of Chemistry, 2003 and the literature cited therein. Known herbicides or plant growth regulators which can be combined with the compounds according to the invention are, for example, the following active substances (the compounds are either designated by the common name according to the International Organization for Standardization (ISO) or by a chemical name, if appropriate together with the code number) and always comprise all use forms such as acids, salts, esters and isomers such as stereoisomers and optical isomers. In this context, one and in some cases also several use forms are mentioned by way of example:

acetochlor, acibenzolar, acibenzolar-S-methyl, aciflurofen, aciflurofen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlorotoluron, chlorsulfuron, cinidon, cinidon-ethyl, cinmethylin, cinosulfuron, clethodim, clodinafop clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), di-allate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoro-propyl)-4,5-dihydro-5-oxo-1H-tetrazol-1-yl]-phenyl]ethanesulfonamide, fenoprop, fenoxaprop, fenoxaprop-P, fenoxaprop-ethyl, fenoxaprop-P-ethyl, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, L-glufosinate, L-glufosinate-ammonium, glufosinate-ammonium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HOK-201, HW-02, imazamethabenz, imazamethabenz-methyl, imazamox, imazapic, imazapyr, imazaquin, imazethapyr, imazosulfuron, inabenfide, indanofan, indoleacetic acid (IAA), 4-indol-3-ylbutyric acid (IBA), iodosulfuron, iodosulfuron-methyl-sodium, ioxynil, isocarbamid, isopropalin, isoproturon, isouron, isoxaben, isoxachlortole, isoxaflutole, isoxapyrifop, KUH-043, KUH-071, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, methabenzthiazuron, metam, metamifop, metamitron, metazachlor, methazole, methoxyphenone, methyldymron, 1-methylcyclopropene, methyl isothiocyanate, metobenzuron, metobenzuron, metobromuron, metolachlor, S-metolachlor, metosulam, metoxuron, metribuzin, metsulfuron, metsulfuron-methyl, molinate, monalide, monocarbamide, monocarbamide dihydrogen sulfate, monolinuron, monosulfuron, monuron, MT 128, MT-5950, i.e. N-[3-chloro-4-(1-methylethyl)-phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolat-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyzamide, prosulfalin, prosulfocarb, prosulfuron, prynachlor, pyraclonil, pyraflufen, pyraflufen-ethyl, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, sulf-allate (CDEC), sulfentrazone, sulfometuron, sulfometuron-methyl, sulfosate (glyphosate-trimesium), sulfosulfuron, SYN-523, SYP-249, SYP-298, SYP-300, tebutam, tebuthiuron, tecnazene, tepraloxydim, terbacil, terbucarb, terbuchlor, terbumeton, terbuthylazine, terbutryne, TH-547, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, tralkoxydim, tri-allate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, ZJ-0862 and the following compounds

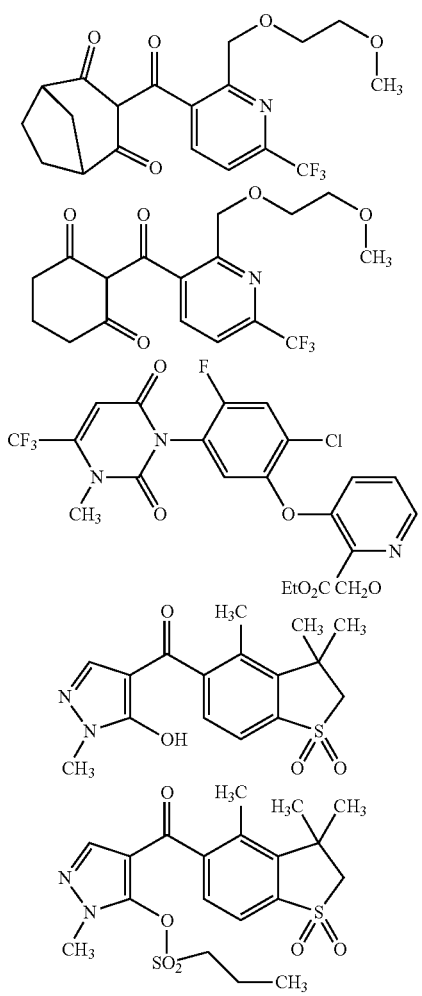

The application rate required of the HPPD inhibitor herbicide of the class of triketones, such as tembotrione, sulcotrione and mesotrione, or of the class of pyrazolinates, such as pyrasulfotole and topramezone, particularly selected from tembotrione, sulcotrione, topramezone, bicyclopyrone, tefuryltrione and mesotrione, more particularly tembotrione to be applied to areas where HPPD tolerant plants according to the present invention are growing varies as a function of the external conditions such as temperature, humidity, the nature of the herbicide used and the like. It can vary within wide limits, for example between 0.001 and 1.0 kg/ha and more of active substance, but it is preferably between 0.005 and 750 g/ha.

In case of combined applications of HPPD inhibitor herbicides with herbicides that differ from HPPD inhibitor herbicides to the HPPD tolerant plants according to the present invention, these mixtures may cause crop injury, based on the presence of the non HPPD inhibitor herbicides. In order to reduce/eliminate such crop injuries, appropriate safeners may be added. These safeners, which are employed in antidotically active amounts, reduce the phytotoxic side effects of herbicides/pesticides used, for example in economically important crops, such as cereals (wheat, barley, rye, corn, rice, millet), alfalfa, sugar beet, sugarcane, oilseed rape, cotton and soya spp., preferably corn, cotton, sugarbeet, or soya spp.

The safeners are preferably selected from the group consisting of:

A) Compounds of the Formula (S-I)

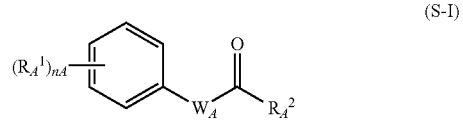

where the symbols and indices have the following meanings:

$n_A$ is a natural number from 0 to 5, preferably from 0 to 3;

$R_A^1$ is halogen, $(C_1-C_4)$-alkyl, $(C_1-C_4)$-alkoxy, nitro or $(C_1-C_4)$-haloalkyl;

$W_A$ is an unsubstituted or substituted divalent heterocyclic radical from the group consisting of partially unsaturated or aromatic five-membered heterocycles having 1 to 3 hetero ring atoms of the type N or O, where at least one nitrogen atom and at most one oxygen atom is present in the ring, preferably a radical from the group consisting of $(W_A^1)$ to $(W_A^4)$,

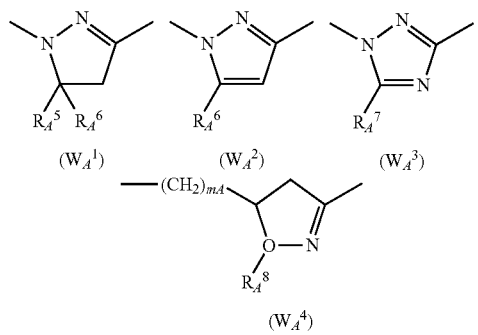

$m_A$ is 0 or 1;

$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S-I) and which is unsubstituted or substituted by radicals from the group consisting of $(C_1-C_4)$-alkyl, $(C_1-C_4)$-alkoxy and optionally substituted phenyl, preferably a radical of the formula $OR_A^3$, $NHR_A^4$ or $N(CH_3)_2$, in particular of the formula $OR_A^3$;

$R_A^3$ is hydrogen or an unsubstituted or substituted aliphatic hydrocarbon radical having preferably a total of 1 to 18 carbon atoms;

$R_A^4$ is hydrogen, $(C_1-C_6)$-alkyl, $(C_1-C_6)$-alkoxy or substituted or unsubstituted phenyl;

$R_A^5$ is H, $(C_1-C_8)$-alkyl, $(C_1-C_8)$-haloalkyl), $(C_1-C_4)$-alkoxy-$(C_1-C_8)$-alkyl, cyano or $COOR_A^9$ where $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;

$R_A^6$, $R_A^7$, $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;

preferably:

a) compounds of the type of the dichlorophenylpyrazoline-3-carboxylic acid, preferably compounds such as ethyl 1-(2,4-dichlorophenyl)-5-(ethoxycarbonyl)-5-methyl-2-pyrazoline-3-carboxylate (S1-1) ("mefenpyr-diethyl", see Pestic. Man.), and related compounds, as described in WO 91/07874;

b) derivatives of dichlorophenylpyrazolecarboxylic acid, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4), ethyl 1-(2,4-dichlorophenyl)-5-phenylpyrazole-3-carboxylate (S1-5) and related compounds, as described in EP-A-333 131 and EP-A-269 806;

c) compounds of the type of the triazolecarboxylic acids, preferably compounds such as fenchlorazole(-ethyl ester), i.e. ethyl 1-(2,4-dichlorophenyl)-5-trichloro-methyl-(1H)-1,2,4-triazole-3-carboxylate (S1-6), and related compounds, as described in EP-A-174 562 and EP-A-346 620;

d) compounds of the type of the 5-benzyl- or 5-phenyl-2-isoxazoline-3-carboxylic acid or the 5,5-diphenyl-2-isoxazoline-3-carboxylic acid, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds, as described in WO 91/08202, or ethyl 5,5-diphenyl-2-isoxazolinecarboxylate (S1-9) ("isoxadifen-ethyl") or n-propyl 5,5-diphenyl-2-isoxazolinecarboxylate (S1-10) or ethyl 5-(4-fluorophenyl)-5-phenyl-2-isoxazoline-3-carboxylate (S1-11), as described in the patent application WO-A-95/07897.

B) Quinoline Derivatives of the Formula (S-II)

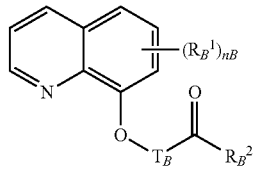

where the symbols and indices have the following meanings:
$R_B^1$ is halogen, $(C_1-C_4)$-alkyl, $(C_1-C_4)$-alkoxy, nitro or $(C_1-C_4)$-haloalkyl;
$n_B$ is a natural number from 0 to 5, preferably from 0 to 3;
$R_B^2$ $OR_B^3$, $SR_B^3$ or $NR_B^3R_B^4$ or a saturated
or unsaturated 3- to 7-membered heterocycle having at least one nitrogen atom and up to 3 heteroatoms, preferably from the group consisting of O and S, which is attached via the nitrogen atom to the carbonyl group in (S-II) and is unsubstituted or substituted by radicals from the group consisting of $(C_1-C_4)$-alkyl, $(C_1-C_4)$-alkoxy or optionally substituted phenyl, preferably a radical of the formula $OR_B^3$, $NHR_B^4$ or $N(CH_3)_2$, in particular of the formula $OR_B^3$;
$R_B^3$ is hydrogen or an unsubstituted or substituted aliphatic hydrocarbon radical having preferably a total of 1 to 18 carbon atoms;
$R_B^4$ is hydrogen, $(C_1-C_6)$-alkyl, $(C_1-C_6)$-alkoxy or substituted or unsubstituted phenyl;
$T_B$ is a $(C_1-$ or $C_2)$-alkanediyl chain which is unsubstituted or substituted by one or two $(C_1-C_4)$-alkyl radicals or by [$(C_1-C_3)$-alkoxy]carbonyl;
preferably:

a) compounds of the type of the 8-quinolinoxyacetic acid (S2), preferably 1-methylhexyl (5-chloro-8-quinolinoxy)acetate (common name "cloquintocet-mexyl" (S2-1) (see Pestic. Man.),
1,3-dimethylbut-1-yl (5-chloro-8-quinolinoxy)acetate (S2-2),
4-allyloxybutyl (5-chloro-8-quinolinoxy)acetate (S2-3),
1-allyloxyprop-2-yl (5-chloro-8-quinolinoxy)acetate-(S2-4),
ethyl (5-chloro-8-quinolinoxy)acetate (S2-5),
methyl (5-chloro-8-quinolinoxy)acetate (S2-6),
allyl (5-chloro-8-quinolinoxy)acetate (S2-7),
2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as described in EP-A-86 750, EP-A-94 349 and EP-A-191 736 or EP-A-0 492 366, and also their hydrates and salts, as described in WO-A-2002/034048.

b) Compounds of the type of the (5-chloro-8-quinolinoxy) malonic acid, preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

C) Compounds of the Formula (S-III)

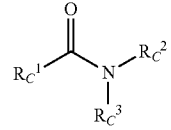

where the symbols and indices have the following meanings:
$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;
$R_C^2$, $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring,
preferably an oxazolidine, thiazolidine, piperidine, morpholine, hexahydropyrimidine or benzoxazine ring;
preferably:
Active compounds of the type of the dichloroacetamides which are frequently used as pre-emergence safener (soil-acting safeners), such as, for example,
"dichlormid" (see Pestic.Man.) (=N,N-diallyl-2,2-dichloroacetamide),
"R-29148" (=3-dichloroacetyl-2,2,5-trimethyl-1,3-oxazolidine from Stauffer),
"R-28725" (=3-dichloroacetyl-2,2,-dimethyl-1,3-oxazolidine from Stauffer),
"benoxacor" (see Pestic. Man.) (=4-dichloroacetyl-3,4-dihydro-3-methyl-2H-1,4-benzoxazine),
"PPG-1292" (=N-allyl-N-[(1,3-dioxolan-2-yl)methyl]dichloroacetamide from PPG Industries),
"DKA-24" (=N-allyl-N-[(allylaminocarbonyl)methyl]dichloroacetamide from Sagro-Chem),
"AD-67" or "MON 4660" (=3-dichloroacetyl-1-oxa-3-azaspiro[4,5]decane from Nitrokemia or Monsanto),
"TI-35" (=1-dichloroacetylazepane from TRI-Chemical RT)
"diclonon" (diclyclonone) or "BAS145138" or "LAB145138" (=3-dichloroacetyl-2,5,5-trimethyl-1,3-diazabicyclo[4.3.0]nonane from BASF) and
"furilazole" or "MON 13900" (see Pestic. Man.) (=(RS)-3-dichloroacetyl-5-(2-furyl)-2,2-dimethyloxazolidine).

D) N-Acylsulfonamides of the Formula (S-IV) and their Salts

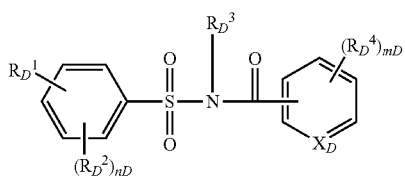

(S-IV)

in which
$X_D$ is CH or N;
$R_D{}^1$ is CO—$NR_D{}^5R_D{}^6$ or NHCO—$R_D{}^7$;
$R_D{}^2$ is halogen, $(C_1\text{-}C_4)$-haloalkyl, $(C_1\text{-}C_4)$-haloalkoxy, nitro, $(C_1\text{-}C_4)$-alkyl, $(C_1\text{-}C_4)$-alkoxy, $(C_1\text{-}C_4)$-alkylsulfonyl, $(C_1\text{-}C_4)$-alkoxycarbonyl or $(C_1\text{-}C_4)$-alkylcarbonyl;
$R_D{}^3$ is hydrogen, $(C_1\text{-}C_4)$-alkyl, $(C_2\text{-}C_4)$-alkenyl or $(C_2\text{-}C_4)$-alkynyl;
$R_D{}^4$ is halogen, nitro, $(C_1\text{-}C_4)$-alkyl, $(C_1\text{-}C_4)$-haloalkyl, $(C_1\text{-}C_4)$-haloalkoxy, $(C_3\text{-}C_6)$-cycloalkyl, phenyl, $(C_1\text{-}C_4)$-alkoxy, cyano, $(C_1\text{-}C_4)$-alkylthio, $(C_1\text{-}C_4)$-alkylsulfinyl, $(C_1\text{-}C_4)$-alkylsulfonyl, $(C_1\text{-}C_4)$-alkoxycarbonyl or $(C_1\text{-}C_4)$-alkylcarbonyl;
$R_D{}^5$ is hydrogen, $(C_1\text{-}C_6)$-alkyl, $(C_3\text{-}C_6)$-cycloalkyl, $(C_2\text{-}C_6)$-alkenyl, $(C_2\text{-}C_6)$-alkynyl, $(C_5\text{-}C_6)$-cycloalkenyl, phenyl or 3- to 6-membered heterocyclyl containing $v_D$ heteroatoms from the group consisting of nitrogen, oxygen and sulfur, where the seven last-mentioned radicals are substituted by $v_D$ substituents from the group consisting of halogen, $(C_1\text{-}C_6)$-alkoxy, $(C_1\text{-}C_6)$-haloalkoxy, $(C_1\text{-}C_2)$-alkylsulfinyl, $(C_1\text{-}C_2)$-alkylsulfonyl, $(C_3\text{-}C_6)$-cycloalkyl, $(C_1\text{-}C_4)$-alkoxycarbonyl, $(C_1\text{-}C_4)$-alkylcarbonyl and phenyl and, in the case of cyclic radicals, also $(C_1\text{-}C_4)$-alkyl and $(C_1\text{-}C_4)$-haloalkyl;
$R_D{}^6$ is hydrogen, $(C_1\text{-}C_6)$-alkyl, $(C_2\text{-}C_6)$-alkenyl or $(C_2\text{-}C_6)$-alkynyl, where the three last-mentioned radicals are substituted by $v_D$ radicals from the group consisting of halogen, hydroxy, $(C_1\text{-}C_4)$-alkyl, $(C_1\text{-}C_4)$-alkoxy and $(C_1\text{-}C_4)$-alkylthio, or
$R_D{}^5$ and $R_D{}^6$ together with the nitrogen atom carrying them form a pyrrolidinyl or piperidinyl radical;
$R_D{}^7$ is hydrogen, $(C_1\text{-}C_4)$-alkylamino, di-$(C_1\text{-}C_4)$-alkylamino, $(C_1\text{-}C_6)$-alkyl, $(C_3\text{-}C_6)$-cycloalkyl, where the 2 last-mentioned radicals are substituted by $v_D$ substituents from the group consisting of halogen, $(C_1\text{-}C_4)$-alkoxy, halogen-$(C_1\text{-}C_6)$-alkoxy and $(C_1\text{-}C_4)$-alkylthio and, in the case of cyclic radicals, also $(C_1\text{-}C_4)$-alkyl and $(C_1\text{-}C_4)$-haloalkyl;
$n_D$ is 0, 1 or 2;
$m_D$ is 1 or 2;
$v_D$ is 0, 1, 2 or 3;
from among these, preference is given to compounds of the type of the N-acylsulfonamides, for example of the formula (S-V) below, which are known, for example, from WO 97/45016

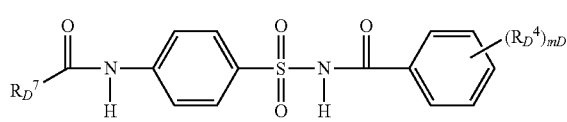

(S-V)

in which
$R_D{}^7$ is $(C_1\text{-}C_6)$-alkyl, $(C_3\text{-}C_6)$-cycloalkyl, where the 2 last-mentioned radicals are substituted by $v_D$ substituents from the group consisting of halogen, $(C_1\text{-}C_4)$-alkoxy, halogen-$(C_1\text{-}C_6)$-alkoxy and $(C_1\text{-}C_4)$-alkylthio and, in the case of cyclic radicals, also $(C_1\text{-}C_4)$-alkyl and $(C_1\text{-}C_4)$-haloalkyl;
$R_D{}^4$ is halogen, $(C_1\text{-}C_4)$-alkyl, $(C_1\text{-}C_4)$-alkoxy, $CF_3$,
$m_D$ is 1 or 2;
$v_D$ is 0, 1, 2 or 3;
and also
acylsulfamoylbenzamides, for example of the formula (S-VI) below, which are known, for example, from WO 99/16744,

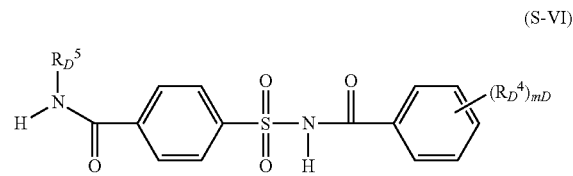

(S-VI)

for example those in which
$R_D{}^5$=cyclopropyl and $(R_D{}^4)$=2-OMe ("cyprosulfamide", S3-1),
$R_D{}^5$=cyclopropyl and $(R_D{}^4)$=5-Cl-2-OMe (S3-2),
$R_D{}^5$=ethyl and $(R_D{}^4)$=2-OMe (S3-3),
$R_D{}^5$=isopropyl and $(R_D{}^4)$=5-Cl-2-OMe (S3-4) and
$R_D{}^5$=isopropyl and $(R_D{}^4)$=2-OMe (S3-5);
and also
compounds of the type of the N-acylsulfamoylphenylureas of the formula (S-VII), which are known, for example, from EP-A-365484

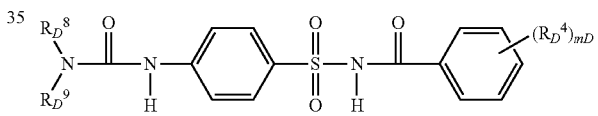

(S-VII)

in which
$R_D{}^8$ and $R_D{}^9$ independently of one another are hydrogen, $(C_1\text{-}C_8)$-alkyl, $(C_3\text{-}C_8)$-cycloalkyl, $(C_3\text{-}C_6)$-alkenyl, $(C_3\text{-}C_6)$-alkynyl,
$R_D{}^4$ is halogen, $(C_1\text{-}C_4)$-alkyl, $(C_1\text{-}C_4)$-alkoxy, $CF_3$
$m_D$ is 1 or 2;
from among these in particular
1-[4-(N2-methoxybenzoylsulfamoyl)phenyl]-3-methylurea,
1-[4-(N2-methoxybenzoylsulfamoyl)phenyl]-3,3-dimethylurea,
1-[4-(N4,5-dimethylbenzoylsulfamoyl)phenyl]-3-methylurea,
1-[4-(N-naphthoylsulfamoyl)phenyl]-3,3-dimethylurea,
G) active compounds from the class of the hydroxyaromatics and aromatic-aliphatic carboxylic acid derivatives, for example
ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 1,2-dihydro-2-oxo-6-trifluoromethylpyridine-3-carboxamide, 2-hydroxycinnamic acid, 2,4-dichlorocinnamic acid, as described in WO 2004084631, WO 2005015994, WO 2006007981, WO 2005016001;
H) active compounds from the class of the 1,2-dihydroquinoxalin-2-ones, for example
1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thie-nyl)-1,2-dihydroquinoxalin-2-one, as described in WO 2005112630, I) active compounds which, in addition to a herbicidal action against harmful plants, also have safener action on crop plants such as rice, such as, for example, "dimepiperate" or "MY-93" (see Pestic. Man.) (=S-1-methyl-1-phenylethyl piperidine-1-thiocarboxylate), which is known as safener for rice against damage by the herbicide molinate, "daimuron" or "SK 23" (see Pestic. Man.) (=1-(1-methyl-1-phenylethyl)-3-p-tolyl-urea), which is known as safener for rice against damage by the herbicide imazosulfuron, "cumyluron"="JC-940" (=3-(2-chlorophenylmethyl)-1-(1-methyl-1-phenyl-ethyl)urea, see JP-A-60087254), which is known as safener for rice against damage by a number of herbicides, "methoxyphenone" or "NK 049" (=3,3'-dimethyl-4-methoxybenzophenone), which is known as safener for rice against damage by a number of herbicides, "CSB" (=1-bromo-4-(chloromethylsulfonyl)benzene) (CAS Reg. No. 54091-06-4 from Kumiai), which is known as safener against damage by a number of herbicides in rice, K) compounds of the formula (S-IX),
as described in WO-A-1998/38856

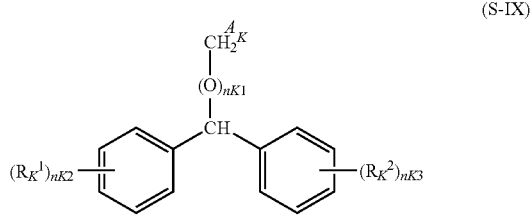

(S-IX)

in which the symbols and indices have the following meanings:

$R_K^1$, $R_K^2$ independently of one another are halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;

$A_K$ is $COOR_K^3$ or $COOR_K^4$ $R_K^3$, $R_K^4$ independently of one another are hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl or alkylammonium, $n_K^1$ is 0 or 1, $n_K^2$, $n_K^3$ independently of one another are 0, 1 or 2 preferably: methyl (diphenylmethoxy)acetate (CAS Reg. No.: 41858-19-9),

L) compounds of the formula (S-X),
as described in WO A-98/27049

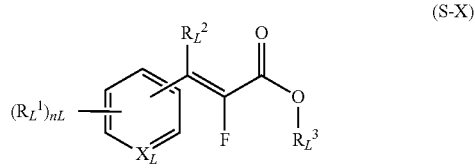

(S-X)

in which the symbols and indices have the following meanings:

$X_L$ is CH or N, $n_L$ is, in the case that X=N, an integer from 0 to 4 and,
in the case that X=CH, an integer from 0 to 5, $R_L^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulfonyl, $(C_1-C_4)$-alkoxycarbonyl, optionally substituted phenyl, optionally substituted phenoxy, $R_L^2$ is hydrogen or $(C_1-C_4)$-alkyl, $R_L^3$ is hydrogen, $(C_1-C_8)$-alkyl, $(C_2-C_4)$-alkenyl, $(C_2-C_4)$-alkynyl or aryl, where each of the carbon-containing radicals mentioned above is unsubstituted or substituted by one or more, preferably by up to three, identical or different radicals from the group consisting of halogen and alkoxy; or salts thereof, M) active compounds from the class of the 3-(5-tetrazolylcarbonyl)-2-quinolones, for example
1,2-dihydro-4-hydroxy-1-ethyl-3-(5-tetrazolylcarbonyl)-2-quinolone (CAS Reg. No.: 219479-18-2), 1,2-dihydro-4-hydroxy-1-methyl-3-(5-tetrazolylcarbonyl)-2-quinolone (CAS Reg. No.: 95855-00-8), as described in WO-A-1999000020, N) compounds of the formula (S-XI) or (S-XII),
as described in WO-A-2007023719 and WO-A-2007023764

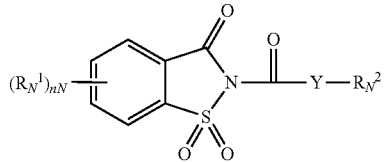

(S-XI)

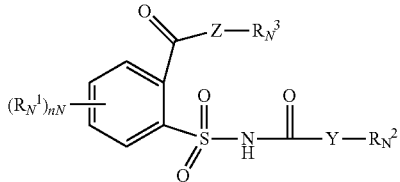

(S-XII)

in which $R_N^1$ is halogen, $(C_1-C_4)$-alkyl, methoxy, nitro, cyano, $CF_3$, $OCF_3$ Y, Z independently of one another are O or S, $n_N$ is an integer from 0 to 4, $R_N^2$ is $(C_1-C_{16})$-alkyl, $(C_2-C_6)$-alkenyl, $(C_3-C_6)$-cycloalkyl, aryl, benzyl, halobenzyl, $R_N^3$ is hydrogen, $(C_1-C_6)$alkyl, O) one or more compounds from the group consisting of:
1,8-naphthalic anhydride,
O,O-diethyl S-2-ethylthioethyl phosphorodithioate (disulfoton),
4-chlorophenyl methylcarbamate (mephenate),
O,O-diethyl O-phenyl phosphorothioate (dietholate),
4-carboxy-3,4-dihydro-2H-1-benzopyran-4-acetic acid (CL-304415, CAS Reg. No.: 31541-57-8),
2-propenyl 1-oxa-4-azaspiro[4.5]decane-4-carbodithioate (MG-838, CAS Reg. No.: 133993-74-5),
methyl [(3-oxo-1H-2-benzothiopyran-4(3H)-ylidene)methoxy]acetate (from WO-A-98/13361; CAS Reg. No.: 205121-04-6),
cyanomethoxyimino(phenyl)acetonitrile (cyometrinil),
1,3-dioxolan-2-ylmethoxyimino(phenyl)acetonitrile (oxabetrinil),
4'-chloro-2,2,2-trifluoroacetophenone O-1,3-dioxolan-2-ylmethyloxime (fluxofenim),
4,6-dichloro-2-phenylpyrimidine (fenclorim), benzyl 2-chloro-4-trifluoromethyl-1,3-thiazole-5-carboxylate (flurazole),
2-dichloromethyl-2-methyl-1,3-dioxolane (MG-191),
including the stereoisomers, and the salts customary in agriculture.

A mixture with other known active compounds, such as fungicides, insecticides, acaricides, nematicides, bird repellents, plant nutrients and soil structure improvers is likewise possible.

Some of the safeners are already known as herbicides and accordingly, in addition to the herbicidal action against harmful plants, also act by protecting the crop plants.

The weight ratios of herbicide (mixture) to safener generally depend on the herbicide application rate and the effectiveness of the safener in question and may vary within wide limits, for example in the range from 200:1 to 1:200, preferably from 100:1 to 1:100, in particular from 20:1 to 1:20. The safeners may be formulated analogously to the compounds of the formula (I) or their mixtures with other herbicides/pesticides and be provided and used as a finished formulation or as a tank mix with the herbicides.

The required application rate of the compound of the formula (I) varies depending, inter alia, on external conditions such as temperature, humidity and the type of herbicide used. It can vary within wide limits, for example between 0.001 and 10 000 g/ha or more of active substance; however, it is preferably between 0.5 and 5000 g/ha, particularly preferably between 0.5 and 1000 g/ha and very particularly preferably between 0.5 and 500 g/ha.

When the transgenic plant of the invention contains one or more other genes for tolerance towards other herbicides (as, for example, a gene which encodes a mutated or unmutated EPSPS which confers on the plant tolerance to glyphosate herbicides or a pat or bar gene conferring tolerance to glufosinate herbicides), or when the transgenic plant is naturally resistant to another herbicide (such as sulfonylurea tolerance), the method according to the invention can comprise the simultaneous or chronologically staggered application of an HPPD inhibitor in combination with the said herbicide or herbicide combination, for example glyphosate and/or glufosinate and/or sulfonylurea herbicides.

The invention also relates to the use of the chimeric gene encoding the HPPD of the invention as a marker gene during the transformation of a plant species, based on the selection on the abovementioned HPPD inhibitor herbicides.

The present invention also relates to a method for obtaining a plant resistant to a triketone or a pyrazolinate HPPD inhibitor, characterized in that the plant is transformed with a chimeric gene expressing in the plant an HPPD of the invention as defined herein.

In a particular embodiment, the invention relates to said method for obtaining a plant resistant to a triketone or a pyrazolinate HPPD inhibitor, characterized in that the HPPD of the invention comprises SEQ ID No. 4 (from the amino acid position 2 to the amino acid position 382), or a synthetic DNA encoding the HPPD of the invention adapted to the codon usage of corn, rice, wheat, soya spp, sugarcane, onion, Brassica species plants, or cotton.

In another particular embodiment, the invention relates to said method for obtaining a plant resistant to a triketone HPPD inhibitor selected from tembotrione, mesotrione, diketonitrile, isoxaflutole, sulcotrione, tefuryltrione, and bicyclopyrone.

In another particular embodiment, the invention relates to said method for obtaining a plant resistant to a triketone or a pyrazolinate HPPD inhibitor, characterized in that the plant also comprises a plant-expressible chimeric gene encoding a PDH (prephenate dehydrogenase) enzyme, or an enzyme with at least PDH.

The invention also relates to a method for controlling weeds in an area or a field, which method comprises planting in this area or field transformed plants resistant to a triketone or a pyrazolinate HPPD inhibitor which has been obtained according to the method described above, or transformed seeds which originates from them, and in applying a dose which is toxic for the weeds of said triketone or pyrazolinate HPPD inhibitor without significantly affecting the said transformed seeds or the said transformed plants.

The invention also relates to a method for obtaining oil or meal comprising growing a transformed plant resistant to a triketone or a pyrazolinate HPPD inhibitor which has been obtained according to the method described above, or a transformed seed which originates from such plant, optionally treating such plant or seed with a triketone or a pyrazolinate HPPD inhibitor, harvesting the grains and milling the grains to make meal and extract the oil.

The invention also relates to the use of an HPPD of the invention as described above, characterized in that the HPPD inhibitor is a triketone HPPD inhibitor selected from tembotrione, mesotrione, topramezone, bicyclopyrone, tefuryltrione and sulcotrione.

The present invention also relates to a host organism, in particular plant cells or plants, which contain a chimeric gene comprising a sequence encoding an HPPD according to the invention, and which also contain a gene functional in this host organism allowing overexpression of a prephenate dehydrogenase (abbreviated herein as PDH) enzyme.

The term "PDH enzyme", as used herein, refers to any natural or mutated PDH enzyme exhibiting the PDH activity of conversion of prephenate to HPP. In particular, said PDH enzyme can originate from any type of organism. An enzyme with PDH activity can be identified by any method that makes it possible either to measure the decrease in the amount of prephenate substrate, or to measure the accumulation of a product derived from the enzymatic reaction, i.e. HPP or one of the cofactors NADH or NADPH.

Many genes encoding PDH enzymes are described in the literature, and their sequences can be identified on the website ncbi.nlm.nih.gov/entrez/. Particularly known is the gene encoding the PDH enzyme of the yeast *Saccharomyces cerevisiae* (Accession No. S46037) as described in Mannhaupt et al. (1989) Gene 85, 303-311, of a bacterium of the *Bacillus* genus, in particular of the species *B. subtilis* (Accession No. P20692) as described in Henner et al. (1986) Gene 49 (1) 147-152, of a bacterium of the *Escherichia* genus, in particular of the species *E. coli* (Accession No. KMECTD) as described in Hudson et al. (1984) J. Mol. Biol. 180(4), 1023-1051, or of a bacterium of the *Erwinia* genus, in particular of the species *E. herbicola* (Accession No. S29934) as described in Xia et al. (1992) J. Gen. Microbiol. 138(7), 1309-1316.

The invention further relates to a method for obtaining a host organism, particularly a plant cell or a plant, resistant to an HPPD inhibitor by integrating in such organism at least one nucleic acid sequence or one chimeric gene as defined above, and by further transforming it, simultaneously or successively, with a gene functional in this host organism allowing expression of a PDH (prephenate dehydrogenase) enzyme. In a particular embodiment, the invention relates to a method for obtaining a host organism, particularly a plant cell or a plant, resistant to a triketone or pyrazolinate HPPD inhibitor, particularly tembotrione, mesotrione topramezone, bicyclopyrone, isoxaflutole, pyrasulfotole, tefuryltrione, or sulcotrione.

Means and methods which could be used for obtaining a host organism, particularly a plant cell or a plant, transformed both with a gene allowing overexpression of an HPPD enzyme, and with a gene allowing overexpression of a PDH enzyme are extensively described in WO 04/024928, the content of which is hereby incorporated by reference.

The reference in this specification to any prior publication (or information derived from it), or to any matter which is known, is not, and should not be taken as an acknowledgement or admission or any form of suggestion that such prior publication (or information) or known matter forms part of the common general knowledge in the field of this invention.

FIGURES

FIG. 1 Map of the plasmid pSE420::FMP37e
FIG. 2 Map of the T-DNA inserted into the tobacco plants
FIG. 3 Map of the T-DNA inserted in the differents plants according to Examples 5 to 13; Abbreviations having the following meanings A, B, C and G, tobacco plants, D, E and F, Zea mays plants, H, soybean plants, I, rice plants, and J, cotton plants. 35S: CaMV35S promoter, KanR: gene conferring resistance to the antibiotic kanamycin, nos: nopaline synthase promoter, Ter: terminator, H6: sequence coding for an His TAG, OTP: optimized transit peptide, BAR (Bialaphos resistant, WO 8705629) and PAT (phosphinothricin N-Acetyltransferase, EP 257542): genes conferring tolerance to Bialaphos, phosphinothricin or glufosinate, 2mEPSPS: gene coding for the double mutant (Thr102Ile and Pro106Ser) EPSPS (5-enolpyruvylshikimate synthase) from Zea mays (US 20030027312), 2 mAHAS: gene coding for the double mutant ALS (acetolactate synthase) from Arabidopsis (Pro197Ala and Trp574Leu; U.S. Pat. No. 5,378,824, HA: histone promoter from Arabidopsis gene, TEV: tobacco etch virus, FMP37e: gene coding for FMP37 optimized for the expression in E coli with an sequence coding for an His TAG at its 5' extremity, FMP37t: gene coding for FMP37 optimized for the expression in dicotyledoneous plants with an sequence coding for an His TAG at its 5' extremity, FMP37t-h, gene coding for FMP37 optimized for the expression in dicotyledoneous plants, FMP37m, gene coding for FMP37 optimized for the expression in Zea mays plants, LB, left border, RB, right border.

SEQUENCES LISTING

SEQ ID No. 1: Nucleic acid sequence encoding *Blepharisma japonicum* HPPD
SEQ ID No. 2: Nucleic acid sequence encoding *Blepharisma japonicum* HPPD optimized for *E. coli*, containing at the 5' end a nucleic acid encoding an alanine and 6 histidine amino acids.
SEQ ID No. 3: Nucleic acid sequence encoding *Blepharisma japonicum* HPPD optimized for *Nicotiana tabaccum* containing at the 5' end a nucleic acid sequence encoding an optimized transit peptide and an HIS Tag.
SEQ ID No. 4: *Blepharisma japonicum* HPPD amino acid sequence derived from SEQ ID No. 1
SEQ ID No. 5: Protein encoded by SEQ ID No. 2
SEQ ID No. 6: *Blepharisma japonicum* HPPD amino acid sequence (SEQ ID No. 4) fused with OTP (optimized transit peptide (WO 2009/144079))
SEQ ID No. 7: Protein encoded by SEQ ID No. 3
SEQ ID No. 8: Nucleic acid sequence encoding *Arabidopsis thaliana* HPPD
SEQ ID No. 9: *Arabidopsis thaliana* HPPD amino acid sequence
SEQ ID No. 10: Protein encoded by SEQ ID No. 8 plus an additional alanine directly downstream of the initial amino acid methionine followed by 6 histidine amino acids
SEQ ID No. 11: Protein of SEQ ID No. 9 plus the OTP sequence located at the N-terminal extremity of the protein.
SEQ ID No. 12: Protein of SEQ ID No. 10 plus the OTP sequence directly located at the N-terminal extremity of the protein.
SEQ ID No. 13: Primer sequence Xho-OTP-for
SEQ ID No. 14: Primer sequence Ncol-OTP-rev
SEQ ID No. 15: Nucleic acid sequence encoding *Blepharisma japonicum* HPPD optimized for dicotyledoneous plants
SEQ ID No. 16 Nucleic acid sequence encoding *Blepharisma japonicum* HPPD optimized for *Zea mays* plants
SEQ ID No. 17 Nucleic acid sequence encoding *Blepharisma japonicum* HPPD optimized for *Brassica napus* plants
SEQ ID No. 18 Nucleic acid sequence encoding *Blepharisma japonicum* HPPD optimized for *Beta vulgaris* plants
SEQ ID No. 19 Nucleic acid sequence encoding *Blepharisma japonicum* HPPD optimized for *Gossypium hirsutum* plants
SEQ ID No. 20 Nucleic acid sequence encoding *Blepharisma japonicum* HPPD optimized for *Glycine max* plants
SEQ ID No. 21 Nucleic acid sequence encoding *Blepharisma japonicum* HPPD optimized for *Hordeum vulgare* plants
SEQ ID No. 22 Nucleic acid sequence encoding *Blepharisma japonicum* HPPD optimized for *Oryza sativa* plants
SEQ ID No. 23 Nucleic acid sequence encoding *Blepharisma japonicum* HPPD optimized for *Triticum aestivum* plants

EXAMPLES

The various aspects of the invention will be better understood with the aid of the experimental examples which follow. All the methods or operations which are described below in these examples are given by way of example and correspond to a choice which is made from among the different methods which are available for arriving at the same or similar result. This choice has no effect on the quality of the result and, as a consequence, any suitable method can be used by the skilled person to arrive at the same or similar result. The majority of the methods for manipulating DNA fragments are described in "Current Protocols in Molecular Biology" Volumes 1 and 2, Ausubel F. M. et al., published by Greene Publishing Associates and Wiley Interscience (1989) or in Molecular cloning, T. Maniatis, E. F. Fritsch, J. Sambrook, 1982, or in Sambrook J. and Russell D., 2001, Molecular Cloning: a laboratory manual (Third edition)

Example 1

Preparation of *Blepharisma japonicum* HPPD (named FMP37e) of SEQ ID No. 5 and of the *Arabidopsis thaliana* HPPD identified by SEQ ID No. 10.

The *Arabidopsis thaliana* AtHPPD coding sequence (1335 bp; Genebank AF047834; WO 96/38567) was initially cloned into the expression vector pQE-30 (QIAGEN, Hilden, Germany) in between the restriction sites of BamHI and HindIII. The obtained vector was called "pQE30-AtHPPD".

The original *Blepharisma japonicum* HPPD sequence (1149 bp) coding for the protein listed under the accession number A8R3H6 at UniProtKB/TrEMBL was modified and synthesized using an *Escherichia coli* K12 optimized codon usage (Eurofins MWG operon (Ebersberg, Germany), GENEius software) and cloned in a modified pBluescript vector (Eurofins MWG operon, Ebersberg, Germany). In this vector, the sequence corresponding to the MCS (multiple cloning site) was partially removed that only the sequences corresponding to the recognition of the restriction enzyme HindIII remained on the both side of the insert.

At the 5' end, directly downstream to the ATG was inserted a nucleic acid sequence coding for an alanine amino acid and a nucleic acid sequence encoding a N-terminal HIS6-Tag (6×HIS, encoded by: cat cat cat cac cat cac). Upstream to the ATG, two additional cytosine base pairs were added in order to obtain a sequence corresponding to the recognition site of the restriction enzyme NcoI and downstream to the stop codon the sequences corresponding to the recognition site of the restriction enzyme XbaI were added. The resulting vector "pBluescript-FMP37e" was digested with the restriction enzymes NcoI and XbaI, the band migrating not to the length of the size of the vector approximately 3000 bp corresponding to the DNA was separated on an agarose gel per electrophoresis. Then the DNA coding for the HPPD was purified using the MinElute™ Gel Extraction Kit (Qiagen, Hilden, Germany) and cloned into the pSE420(RI)NX vector (see below) previously cut with the same restriction enzymes.

The cloning and expression vector pSE420(RI)NX (5261 bp) is based on the plasmid pSE420 by Invitrogen (Karlsruhe, Germany). Modifications of this vector include the addition of a nptII gene (neomycin phosphotransferase; Sambrook and Russell, 2001, Molecular Cloning: a laboratory manual (Third edition)) conferring tolerance to the antibiotic kanamycin and is missing the majority of the superlinker region (multiple cloning site).

The plasmid possesses the trp-lac (trc) promoter and the lacI$^q$ gene that provides the lac repressor in every $E.$ $coli$ host strain. The lac repressor binds to the lac operator (lacO) and restricts expression of the target gene; this inhibition can be alleviated by induction with Isopropyl β-D-1-thiogalactopyranoside (IPTG).

The resulting vector was called "pSE420(RI)NX-FMP37e" (see FIG. 1) and it was used to transform $Escherichia$ $coli$ BL21 cells (Merck, Darmstadt, Germany). For the AtHPPD ($Arabidopsis$ $thaliana$ HPPD) that was used as reference see WO 2009/144079.

Expression of HPPD was carried out in $E.$ $coli$ K-12 BL21 containing pQE30-AtHPPD or pSE420(RI)NX-FMP37e. Cells were allowed to grow until OD reached 0.5, then expression was initiated from the trp-lac (trc) promoter by induction with 1 mM IPTG which binds to the lac repressor and causes its dissociation from the lac operon. Expression was carried out over 15 h at 28° C.

To prepare the pre-starter culture, 2 mL of TB medium (100 μg*mL$^{-1}$ carbenicillin) were inoculated with 50 μL of an $E.$ $coli$ K-12 BL21 glycerol stock. The pre-starter culture was incubated at 37° C. with shaking at 140 rpm for 15 h. 200 μl of the pre-starter culture was used to initiate the starter culture (5 mL TB supplement with 100 μg*L$^{-1}$), which was incubated 3 h at 37° C.

To prepare the main culture, 400 mL of TB medium (100 μg*mL$^{-1}$ carbenicillin) were inoculated with 4 mL of the starter culture. This starter culture was incubated at 37° C. with shaking at 140 rpm until OD$_{600}$ 0.5 was reached. Then recombinant protein expression was induced with 400 μl of 1M IPTG solution. The cells were allowed to grow for an additional hour under these conditions, then the temperature was lowered to 28° C. and the culture was shaken at 140 rpm for 15 h. Cells were harvested by centrifugation at 6000×g for 15 min at 4° C. Then cell pellets were stored at −80° C.

Isolation and Purification of His$_6$-AtHPPD and His$_6$-FMP37E in Native Form Lysis of Cells Cells were lysed using Lysozyme, an enzyme that cleaves the 1,4-β-linkages between N-acetylmuramic acid and N-acetyl-D-glucosamine residues in peptidoglycan which forms the bacterial cell wall. Cell membranes were then disrupted by the internal pressure of the bacterial cell. In addition, the lysis buffer contained Benzonase® Nuclease, an endonuclease that hydrolyzes all forms of DNA and RNA without damaging proteins and thereby largely reduces viscosity of the cell lysate. Lysis under native conditions was carried out on ice.

For purification of His$_6$-tagged proteins the QIAexpress® Ni-NTA Fast Start Kit was used following the user manual instruction.

Purification of His$_6$-Tagged Proteins by Immobilized Metal Ion Affinity Chromatography (IMAC)

The cleared cell lysate (10 mL) obtained after centrifugation of the lysis reaction was loaded onto a Ni-NTA Fast Start Column from the QIAexpress® Ni-NTA Fast Start Kit (Qiagen, Hilden, Germany) and purification was carried out according to the instruction manual. The His$_6$-tagged protein was eluted with 2.5 mL of elution buffer.

Desalting of HPPD Solutions by Gel Filtration

HPPD solutions eluted from a Ni-NTA Fast Start Column with 2.5 mL of elution buffer were applied to a Sephadex G-25 PD-10 column (GE Healthcare, Freiburg, Germany) following the user manual instruction. After the whole sample had entered the gel bed, elution was performed with 3.5 mL of storage buffer. The HPPD solutions eluted from the desalting column were frozen at −80° C. in 1 mL aliquots.

Determination of HPPD protein concentration using the Bradford protein assay Protein concentration was determined using the standard Bradford assay (Bradford, (1976), Anal Biochem 72: 248-254).

Determination of Purity of HPPD Solutions Using SDS-Page

The integrity of the eluted protein was checked by SDS-PAGE protein gel electrophoresis using the gel NuPAGE® Novex 4-12% Bis-Tris Gels (Invitrogen, Karlsruhe, Germany), approximately 10 μg of protein were loaded. 10 μL of Laemmli Sample Buffer was added to 1-10 μL of protein solution and the mixture was incubated at 90° C. for 10 min. After short centrifugation step, the whole mixture was loaded into a slot of an SDS gel previously fixed in a XCell Sure-Lock™ Novex Mini-Cell gel chamber filled with NuPAGE® MOPS SDS Running Buffer (diluted from the 20×-solution with ddH$_2$O). A voltage of 150 was then applied to the gel chamber for 1 h. For staining of protein bands, the gel was immersed in Coomassie Brilliant Blue R-250 Staining Solution. For destaining of the polyacrylamide gel, it was immersed in Coomassie Brilliant Blue R-250 Destaining Solution until protein bands appear blue on a white gel.

Example 2

Kinetic characterization and evaluation of tolerance to HPPD inhibitors of HPPD enzymes "SEQ ID No. 5" and "SEQ ID No. 10".

The HPPD activity was checked by the standard spectrophotometric assay (method extensively described in WO 2009/144079)

Determination of HPPD In Vitro Kinetic Properties $K_m$, $V_{max}$, and $k_{cat}$ values for different HPPD enzyme preparations and $K_i$, $K_1=K_{on}$, and $K_{-1}=K_{off}$ for different HPPD inhibitors were determined using a HPLC assay for measurements of HPPD activity. The assay mixtures contained in a volume of 1 ml 150 mM Tris-HCl buffer at pH 7.8, 10 mM sodium ascorbate, 650 units of bovine catalase (Sigma C30 (Sigma-Aldrich, Munich, Germany), 34 mg protein/ml, 23,000 units/mg), and appropriate amounts of HPP, purified HPPD enzyme and HPPD inhibitors. For $K_m$, $V_{max}$, and $k_{cat}$ value determination HPP concentrations in the assay mixture were varied between 10 and 400 µM. For $K_i$, $K_1=K_{on}$, and $K_{-1}=K_{off}$ value determination 2 mM HPP was used. All assays were started by the addition of HPPD enzyme to the assay mixture and stopped at a series of times between 0 and 240 s by addition of 200 µl of the reaction mixture to reaction assay tubes containing 20 µl 10% perchloric acid. Precipitated protein was pelleted by a 5 minute centrifugation at 10,000 g. 100 µl of the supernatant were loaded onto a 250×4 mm Knauer (Berlin, Germany) Eurospher 100-5 C18-column equilibrated with 10% methanol, 0.1% trifluoroacetic acid (buffer A). The column was eluted, also at 1.5 ml/min, using a 4 minute wash with buffer A, followed by a 3 min wash with 95% methanol and by a further 2 minute wash with buffer A. The elution of HGA (homogentisic acid) and HPP (hydroxyphenylpyruvate) was monitored at 292 nm. HGA elutes at around 5 minutes and HPP elutes later. A standard set of concentrations of HGA were used to provide a standard curve in order to calibrate the 292 nm absorbance of the HGA peak versus HGA concentration. For $K_m$ and $V_{max}$ value determinations the initial rates of the HPPD reaction at different substrate concentrations were determined from plots of HGA formed versus time and fitted to the Michaelis-Menten equation for unireactant enzymes using the ID Business Solutions Ltd. (idbs.com) XLfit software suite. For the determination of $K_i$, $K_1=K_{on}$, and $K_{-1}=K_{off}$ values the time-courses of the HPPD reaction at different inhibitor concentrations were fitted to the equations for Mechanism A, competitive inhibition, for tight-binding inhibitors (Cha, S. (1975) Tight-binding inhibitors—I. Kinetic behaviour. Biochemical Pharmacology 24, 2177-2185) using the ID Business Solutions Ltd. XLfit software suite Table1: Kinetic characterization of HPPD enzymes (*Arabidopsis thaliana* "SEQ ID No. 10" and *Blepharisma japonicum* "SEQ ID No. 5") and their respective tolerance to the HPPD inhibitor diketonitrile.

In below given table1, "Km" (Michaelis-Menten constant) means the kinetic parameter that is used to characterise an enzyme, and it is defined as the concentration of substrate that permits half maximal rate of the reaction. Km is further defined as the substrate concentration at which the reaction rate reaches half of its maximum value ($V_{max}/2$) where Vmax has the meaning of being the maximum velocity of the reaction.

$K_{on}=K_1$ equals the association rate constant of the enzyme-substrate binding and $K_{off}=K_{-1}$ equals the rate constant of the enzyme-inhibitor complex dissociation. KI defines the inhibition constant.

TABLE 1

| | HPP | | Diketonitrile | | |
|---|---|---|---|---|---|
| | $K_m$ (µM) | $V_{max}$ (µM) | $k_1$ (M$^{-1}$ s$^{-1}$) | $k_{-1}$ (s$^{-1}$) | $K_i$ (µM) |
| SEQ ID No. 10 | 6.3 | 1.2 | 6.1E+05 | 1.1E−02 | 0.018 |
| SEQ ID No. 5 | 83 | 0.1 | 9.8E+02 | 6.5E−03 | 6.6 |

On the above Table 1, it can be clearly seen, that the kinetic parameters Km and Vmax of the protist HPPD "SEQ ID No. 5" and of the plant HPPD "SEQ ID No. 10" already showed significant differences (6.3 µM vs. 83 µM) which are even higher concerning the tolerance level to diketonitrile (0.018 µM vs. 6.6 µM). The protist HPPD "SEQ ID No. 5" was far more tolerant to the HPPD inhibitor tested than the plant HPPD "SEQ ID No. 10".

Table 2: in vitro tolerance measurement of both HPPD enzymes from *Arabidopsis* (SEQ ID No. 10) and *Blepharisma japonicum* (SEQ ID No. 5) to the HPPD inhibitor herbicide tembotrione. The given numbers represent the percentage of inhibition of the enzyme activity at different concentrations of the HPPD inhibitor herbicide tembotrione compared to the activity in absence of the HPPD inhibitor herbicide. These measurements were done using the spectrophotometric method extensively described in WO 2009/144079.

TABLE 2

| Tembotrione | % Inhibition | |
|---|---|---|
| Concentration (M) | SEQ ID No. 10 | SEQ ID No. 5 |
| 2.5E−04 | 97 | 100 |
| 6.3E−05 | 97 | 86 |
| 2.5E−05 | 93 | 56 |
| 1.0E−05 | 97 | 13 |
| 5.0E−06 | 90 | 0 |
| 2.5E−06 | 82 | 0 |

On the Table 2, it can be clearly seen that the HPPD from *Blepharisma japonicum* (SEQ ID No. 5) is far more tolerant to the HPPD inhibitor herbicide tembotrione than the HPPD obtained from *Arabidopsis thaliana* (SEQ ID No. 10).

Determination of HPPD Activity in Presence of Several HPPD Inhibitors

In this content, $pI_{50}$-value means the log value of the concentration of inhibitor necessary to inhibit 50% of the enzyme activity in molar concentration.

$pI_{50}$-values for HPPD inhibitors were determined from dose-response plots of HPPD activity versus inhibitor concentration using the assay extensively described in WO 2009/144079 at 2 mM fixed HPP concentration and 3 minutes fixed incubation time using the ID Business Solutions Ltd. XLfit software suite.

Table 3: Determination of pI50 HPPD enzymes (*Arabidopsis thaliana* "SEQ ID No. 10" and *Blepharisma japonicum* "SEQ ID No. 5") and their respective tolerance to the several listed below HPPD inhibitors tembotrione, diketonitrile, mesotrione, bicyclopyrone, pyrasulfotole, sulcotrione, pyrazolate, tefuryltrione, and benzofenap. The symbol ">>" means that the value was far higher than the one indicated but could not be precisely calculated within in the range of concentration of inhibitor tested ($2.5\times10^{-6}$, $5.0\times10^{-6}$, $1.0\times10^{-5}$, $2.5\times10^{-5}$, $6.3\times10^{-5}$, and $2.5>10^{-4}$M).

TABLE 3

|  | Tembotrione | Diketonitrile | Mesotrione | Bicyclopyrone |
|---|---|---|---|---|
| SEQ ID No. 10 | >>5.6 | >>5.6 | >>5.6 | 5.2 |
| SEQ ID No. 5 | 4.6 | 5.3 | 4.2 | 3.7 |

|  | Pyrasulfotole | Sulcotrione | Pyrazolate | Tefuryltrione | Benzofenap |
|---|---|---|---|---|---|
| SEQ ID No. 10 | 5.4 | >>5.6 | 5.4 | >>5.6 | >>5.6 |
| SEQ ID No. 5 | 4.4 | 4.8 | 4.7 | n.d. | 5.5 |

Table 4: Determination of percentage of inhibition in presence of $5.0 \times 10^{-6}$ M inhibitors compared to the activity measured in absence of the inhibitor for the HPPD originated from *Arabidopsis thaliana* (SEQ ID No. 10) and from *Blepharisma japonicum* (SEQ ID No. 5).

TABLE 4

|  | Tembotrione | Diketonitrile | Mesotrione | Bicyclopyrone |
|---|---|---|---|---|
| SEQ ID No. 10 | 92 | 87 | 86 | 29 |
| SEQ ID No. 5 | 0 | 49 | 0 | 0 |

|  | Pyrasulfotole | Sulcotrione | Pyrazolate | Tefuryltrione | Benzofenap |
|---|---|---|---|---|---|
| SEQ ID No. 10 | 69 | 74 | 61 | 100. | 90 |
| SEQ ID No. 5 | 0 | 7 | 0 | n.d. | 85 |

On the above Tables 3 and 4, it can be clearly seen, that the protist HPPD "SEQ ID No. 5" showed superior level of tolerance to all tested HPPD inhibitors than the plant at all tested HPPD inhibitor concentrations than observed by employing the HPPD "SEQ ID No. 10" under identical experimental conditions.

Example 3

Construction of Chimeric Genes for the Evaluation HPPD Inhibitor Herbicide Tolerance in Tobacco Plants A) Construction of the Chimeric Genes The vector pRP-RD224 (extensively described in WO 2009/144079) containing the sequence coding for the OTP was used for PCR-mediated attachment upstream of the nucleic acid sequence corresponding to the recognition site of the restriction enzyme XhoI and downstream of the nucleic acid sequence corresponding to the recognition site of the restriction enzyme NcoI. The obtained PCR product was cloned in the vector pCR®-Blunt II-TOPO® (Invitrogen, Karlsruhe, Germany) following the user manual instruction. The resulting vector was called "pCR-TOPO-OTP". The insertion of the correct sequence was confirmed per standard DNA sequencing. The DNA corresponding to the OTP was digested with the restriction enzymes NcoI and XhoI, separated per appropriate gel electrophoresis and cloned into the plasmid pRT100 (Toepfer, (1987), Nucleic Acids Res 15:5890) previously and correspondingly digested with NcoI and XhoI restriction enzymes. The plasmid pRT100 is containing the CaMV35S promoter and CaMV35S terminator. The resulting vector was subsequently digested with the restriction enzymes NcoI and XbaI. The vector pSE420(RI)NX-FMP37e (see FIG. 1) was subjected to the restriction enzymes NcoI and XbaI in order to obtain the DNA fragment corresponding to the SEQ ID No. 2. The resulting vector was digested by employing the restriction enzyme HindIII to sub-clone the CaMV35S::OTP::FMP37e::CaMV35-term cassette (see FIG. 2) into the binary vector pBin19 (Bevan (1984), Nucleic Acids Res. 12:8711-8721.) previously digested with the same enzyme and dephosphorylated. The resulting vector was called "FMP37ebv".

The vectors pQE-30-AtHPPD was used for PCR-mediated attachment of an NcoI restriction site and of a sequence encoding an N-terminal His$_6$-Tag to the 5' ends and a XbaI restriction site to the 3' ends of AtHPPD.

The PCR product of the AtHPPD gene was isolated from an agarose gel, cut with the restriction enzymes NcoI and XbaI, purified with the MinElute™ PCR Purification Kit (Qiagen, Hilden, Germany) and cloned into the pSE420(RI)NX vector cut with the same restriction enzymes.

The generated vector was called "pSE420(RI)NX-AtHPPD" and was digested with the restriction enzymes NcoI and XbaI and cloned into the previously opened vector pRT100 (Toepfer et al., (1987), Nucleic Acids Res 15:5890) containing the CaMV35S promoter and CaMV35S terminator. The generated vector was called "pRT100-AtHPPD".

The vector pCR-TOPO-OTP was digested with the restriction enzymes NcoI and XhoI, and the DNA band corresponding to the OTP was cloned in the previously opened vector pRT100-AtHPPD with the above mentioned restriction enzymes. The resulting vector was subsequently digested with restriction enzyme HindIII and the expression cassette of interest was cloned into the previously opened and dephosphorylated binary vector pBin19. The resulting vector was called "AtHPPDbv".

The binary vectors FMP37ebv and AtHPPDbv were used to transform *Agrobacterium tumefaciens* (ATHV derived from EHA101) competent cells selected on YEB media supplemented with the antibiotics kanamycin and rifampicin (extensively described in the patent application US005925808A).

These *Agrobacterium* strains containing the binary vectors of interest (FMP37ebv or AtHPPDbv) were used to transform leaf discs from tobacco *Nicotiana tabacum* L. cv Samsun NN plants, having approximately a size of 5×5 mm² as extensively described in Horsch et al., (1985), Science 227; 1229-1231.

The leaf disks were co-cultivated for 2 days with *Agrobacterium tumefaciens* cells containing either the binary vector FMP37ebv or AtHPPDbv. Then the leaf disks were transferred to a media allowing the regeneration of shoots for 6 weeks on MS (Musharige and Skoog, (1962), Physiol Plant 15(3): 473-497) media supplemented with BAP (1 mg/mL; Benzylaminopurine), carbenicillin (250 mg/mL), cefotaxine (250 mg/mL), kanamycin (75 mg/mL) and tembotrione ($10^{-6}$ M)

Regenerated calli were transferred on media to induce the development of roots for 6 to 12 weeks: MS (½), supplemented with carbenicillin (250 mg/mL), cefotaxine (250 mg/mL), kanamycin (75 mg/mL), and tembotrione ($10^{-6}$ M).

After 6 weeks on this media, the shoots transformed with *Agrobacterium tumefaciens* cells containing the binary vector AtHPPDbv, were transferred on the same media depleted of HPPD inhibitor tembotrione.

The results are summarized on Table 5, below.

During the entire experiment, the plates containing the leaf disk were located in a growth chamber under controlled conditions (light 16 h, night 8 h, 25° C.).

Rooting of Calli

Regenerated shoot calli from a cell transformed with a nucleic acid sequence encoding an HPPD comprising SEQ ID No. 11 (*Arabidopsis thaliana*) or SEQ ID No. 7 (*Blepharisma japonicum*) were transferred to a media inducing rot growth which media was further supplemented with the HPPD inhibitor tembotrione for 6 to 12 weeks. On none of the events containing the HPPD defined by SEQ ID No. 11 (*Arabidopsis thaliana*) or none transformed calli, root growth was observed under the above given conditions. Contrary to this, under the identical conditions, the calli containing the HPPD defined by SEQ ID No. 7 clearly developed numerous and healthy roots (see Table 5, below).

TABLE 5

| Calli containing: | Events selected for molecular analysis | % Elongation & rooting on $10^{-6}$M tembotrione | Numbers of events rooted on media without tembotrione |
|---|---|---|---|
| SEQ ID No. 11 | 21 | 0 | 5 |
| SEQ ID No. 7 | 31 | 65 | 20 |

Leaf Disk Regeneration

Leaf disks were cut from plants containing HPPD SEQ ID No. 11 (*Arabidopsis thaliana*) or SEQ ID No. 7 (*Blepharisma japonicum*), followed by regeneration for 6 weeks under standard culture conditions on MS media supplemented with BAP (1 mg/mL; Benzylaminopurine), carbenicillin (250 mg/mL), cefotaxine (250 mg/mL) and further comprising one of the following listed HPPD inhibitors at the mentioned concentration (tembotrione ($10^{-6}$M), diketonitrile ($5 \cdot 10^{-6}$ M), Mesotrione ($10^{-6}$ M) and bicyclopyrone ($10^{-6}$ M)) with a media containing none HPPD inhibitors as the positive control. At the end of the experiments the level of regeneration was evaluated as followed:

"−" means that the leaf disks looked the same as leaf disk from wild type tobacco plants on media supplemented with the inhibitor mentioned above.

"++++" means that the leaf disks looked like the leaf disks from the wild type tobacco plants on media without inhibitor.

"+", "++", and "+++" indicate regenerated leaf disks were heavily (+), medium (++) and less (+++) affected by the presence of the inhibitors.

The results of the experiments are summarized in Table 6.

Table 6: Effects of various HPPD inhibitors the regeneration of leaf disk originating from transgenic plants comprising either a gene coding for an HPPD obtained from *Arabidopsis* (SEQ ID No. 11) or from *Blepharisma japonicum* SEQ ID No. 7.

TABLE 6

| Leaf disks containing | Control | Tembotrione | Diketonitrinile | Mesotrione | Bicyclopyrone |
|---|---|---|---|---|---|
| SEQ ID NO 11 | ++++ | − | − | − | − |
| SEQ ID NO 7 | ++++ | ++++ | +++ | ++++ | ++++ |

Whereas in case of plants containing HPPD defined by SEQ ID No. 7 (*Blepharisma japonicum*) showed the same or only slightly reduced regeneration compared to this un-treated control, the corresponding plants containing HPPD defined by SEQ ID No. 11 (*Arabidopsis thaliana*) did not show any regeneration but developed clearly visible bleaching phenotype compared to the untreated control in the presence of all tested HPPD inhibitors.

Example 4

Glasshouse Trials to Evaluate Tolerance to HPPD Inhibitor Herbicides of Transgenic Tobacco Plants Expressing a Gene Coding for Tolerant HPPD Protein Preparation of transgenic plant lines expressing either *Arabidopsis* or FMP37 HPPD enzymes. Glasshouse testing for herbicide tolerance.

Response to Tembotrione, Isoxaflutole and Bicyclopyrone

T0 Tobacco plants containing either the gene from *Arabidopsis* coding for HPPD or the gene FMP37e from *Blepharisma japonicum* coding for FMP37 HPPD, mentioned above (Example 3), were transferred to the glasshouse (28/20° C.), to develop further and produce seeds. Those seeds were harvested and put on soil (ED73 mixed with sand and osmocote Pro) to germinate in the glasshouse (28/20° C.). Three to four weeks later, plantlets were transferred to single pots containing the soil mentioned above. Two weeks later, plants of a size 4-6 cm diameter were sprayed with either

- tembotrione at 100 g AI/ha prepared from a WP20 (wettable powder 20%) formulation supplemented with ammonium sulfate and methyl ester raps oil, or
- isoxaflutole at 100 g AI/ha prepared from a WP20 formulation supplemented with ammonium sulfate and methyl ester raps oil, or
- bicyclopyrone at 100 g AI/ha prepared from a WP20 formulation supplemented with ammonium sulfate and methyl ester raps oil, or
- "blind formulation" made from a WP20 formulation without active ingredient (AI) supplemented with ammonium sulfate and methyl ester raps oil, and were then transferred to a growth chamber with adequate light conditions (20000Lux).

Seven days after the application (DAT) of the different herbicides, the symptoms in tranformed plants were evaluated in comparison to the response observed on the wild type tobacco plants sprayed at the same time and under the same conditions as the tobacco plants containing the transgenes (100% means the plants displayed the same bleaching phenotype as the wild type plants, 0% means that the plants looked like the wild type plants treated with the "blind formulation", and intermediate percentage represent the degree of observed symptoms).

Table 7: Wild type tobacco plants (A) and T1 populations of tobacco events containing alternatively, the expression cassettes described above having the promoter CaMV 35S, the sequence coding for OTP and the sequence coding for *Arabidopsis* HPPD (B) or the promoter CaMV35S, the sequence encoding OTP, and the sequence FMP37e coding for the HPPD FMP37 (C). Assessments of herbicidal damage at 7 days after application (DAT) per spray with 100 g AI/ha of tembotrione or isoxaflutole supplemented with ammonium sulfate and methyl ester raps oil. It is clear that plants containing FMP37e gene were far more tolerant to tembotrione and isoxaflutole. Plants belonging to categories (B) and (C) have not been selected for the presence of the respective transgene prior to the herbicide application.

TABLE 7

| | | | % injury, 7DAT, 100 g AI/ha | |
|---|---|---|---|---|
| | Line | | Tembotrione | Isoxaflutole |
| A | WT | 1 | 100 | 100 |
| Wild Type | WT | 2 | 100 | 100 |
| | WT | 3 | 100 | 100 |
| | WT | 4 | 100 | 98 |
| | WT | 5 | 100 | 99 |
| | WT | 6 | 100 | 99 |
| | WT | 7 | 100 | 100 |
| | WT | 8 | 100 | n.d. |
| | WT | 9 | 100 | n.d. |
| | WT | 10 | 100 | n.d. |
| | WT | 11 | 100 | n.d. |
| | WT | 12 | 100 | n.d. |
| | WT | 13 | 100 | n.d. |
| | WT | 14 | 100 | n.d. |
| B | 258 | 1 | 100 | 100 |
| *Arabidopsis* HPPD | 258 | 2 | 100 | 100 |
| | 258 | 3 | 100 | 100 |
| | 258 | 4 | 100 | 100 |
| | 258 | 5 | 100 | 100 |
| | 258 | 6 | 30 | 100 |
| | 252 | 1 | 30 | 30 |
| | 252 | 2 | 40 | 70 |
| | 252 | 3 | 40 | 95 |
| | 252 | 4 | 40 | 98 |
| | 252 | 5 | 50 | 98 |
| | 252 | 6 | 60 | 99 |
| | 252 | 7 | 60 | 99 |
| | 252 | 8 | 70 | 99 |
| | 252 | 9 | 70 | 99 |
| | 252 | 12 | 75 | 100 |
| | 252 | 13 | 75 | 100 |
| | 252 | 14 | 75 | 100 |
| | 252 | 15 | 80 | 100 |
| | 327 | 1 | 10 | 10 |
| | 327 | 2 | 20 | 20 |
| | 327 | 3 | 20 | 60 |
| | 327 | 4 | 40 | 60 |
| | 327 | 5 | 50 | 70 |
| | 327 | 6 | 50 | 80 |
| | 327 | 7 | 70 | 95 |
| | 327 | 8 | 70 | 98 |
| | 327 | 9 | 70 | 99 |
| | 327 | 10 | 70 | 100 |
| | 327 | 11 | 70 | 100 |
| | 327 | 12 | 80 | 100 |
| | 327 | 13 | 80 | 100 |
| | 327 | 14 | 80 | 100 |
| | 327 | 15 | 80 | 100 |
| C | 113 | 1 | 5 | |
| FMP37e | 113 | 2 | 10 | |
| | 113 | 3 | 10 | |
| | 113 | 4 | 40 | |
| | 113 | 5 | 70 | |
| | 113 | 6 | n.d. | 30 |
| | 113 | 7 | n.d. | 30 |
| | 113 | 8 | n.d. | 30 |
| | 113 | 9 | n.d. | 30 |

TABLE 7-continued

| | % injury, 7DAT, 100 g AI/ha | |
|---|---|---|
| Line | Tembotrione | Isoxaflutole |
| 113  10 | n.d. | 50 |
| 207  1 | | |
| 207  2 | | |
| 207  3 | | |
| 207  4 | | |
| 207  5 | | |
| 207  6 | | |
| 207  7 | | |
| 207  8 | | |
| 207  9 | | |
| 207  10 | n.d. | |
| 207  11 | n.d. | |
| 207  12 | n.d. | 40 |
| 208  1 | | |
| 208  2 | | |
| 208  3 | | |
| 208  4 | | |
| 208  5 | | |
| 208  6 | | |
| 208  7 | | |
| 208  8 | | |
| 208  9 | | |
| 208  10 | | |
| 208  11 | | |
| 208  12 | | n.d. |
| 208  13 | | n.d. |
| 208  14 | | n.d. |
| 208  15 | | n.d. |

Response to Bicyclopyrone.

Seeds of wild type tobacco plants and T1 tobacco plants carrying the gene from *Blepharisma japonicum* FMP37e coding for HPPD were sown on MS media (Murashige and Skoog 1964) supplemented with 50 g/L kanamycin. After 4 weeks, rooted green plantlets were transferred to soil and grown for 3 weeks in the glasshouse as described above then sprayed with a mixture containing bicyclopyrone (100 g AI/ha), ammonium sulfate and methyl ester raps oil. The plants were classified in two categories based on the phenotype developed in response to the herbicide seven days after the treatment. Class I was defined as plants displayed no injuries to light injuries in response to the herbicide treatment (injury: 0-30%), Class II was defined as plants displaying strong injuries to similar injuries as seen with wild type plants submitted to the same treatment (injury: 31-100%). In this case, only plants containing at least one T-DNA were exposed to the herbicidal treatment. In general, it can be seen that even the plants containing only one T-DNA insert already showed up a significant and sufficient level of tolerance to an expose a field dose of the HPPD inhibitor herbicide bicyclopyrone.

TABLE 8

| | | Bicyclopyrone, 100 g AI/ha 7 DAT | | |
|---|---|---|---|---|
| Transgene | Line | Class I | Class II | % of tolerant plant |
| — | WT | 0 | 12 | 0 |
| FMP37e | 113 | 60 | 78 | 56 |
| FMP37e | 207 | 65 | >100 | >60 |
| FMP37e | 208 | 44 | 90 | 67 |

The plants containing the HPPD FMP37 displayed tolerance to the HPPD inhibitor herbicide bicyclopyrone.

It can be summarized from the above presented data, that the plants expressing the gene FMP37e from *Blepharisma japonicum* coding for the FMP37 HPPD obtained from several independent transgenic events are highly tolerant to several HPPD inhibitor herbicides at doses applied under standard agronomic conditions.

Example 5

Construction of Binary Vectors to Express Several Dicotyledoneous Optimized Variants in Plants and Glasshouse Trial to Evaluate Tolerance of Tobacco Plants Containing Such Variants Cloning into pBin19 of FMP37t (SEQ Id No. 3), FMP37t-h (SEQ Id No. 15)

A gene with codon usage optimized for the expression in dicotyledoneous plants coding for the HPPD protein FMP37 were designed, and named FMP37t-h (SEQ ID No. 15) and the same gene with an additional sequences coding for an OTP and for an HIS TAG at its 5' extremity called FMP37t (SEQ ID No. 3). The sequence corresponding to FMP37t-h gene was cloned using the restriction enzymes NcoI and XbaI in the previously described vector pRT100-OTP, containing a CaMV35S promoter and terminator. The resulting vector was called pRT100-OTP-FMP37t-h. The sequence corresponding to FMP37t was cloned in the previously described vector pRT100 using the restriction enzymes XhoI and XbaI, and the resulting vector was called pRT100-OTP-FMP37t. The fragments corresponding to PromCaMV35S-OTP-FMP37t-h-TerCaMV35S and PromCaMV35S-OTP-HIS6-FMP37t-TerCaMV35S were subcloned in the pBIN19 vector (described above) using the restriction enzyme Sbfl. The binary vectors were respectively called pBin19-FMP37t-h (FIG. 3C) and pBin19-FMP37t (FIG. 3B) and can be used for example to transform dicotyledenous plants, such as tobacco plants as described above. Sufficiently grown transformant plants are then tested for their tolerance to HPPD inhibitor herbicides, such as tembotrione. The development of the observed symptoms in response to the herbicidal treatment is evaluated and compared to the response of wild type plants under the same conditions.

Plant Transformation, and Selection of T0 with 100 g AI/TBT

As an example, rooted plants containing the T-DNA PromCaMV35S-OTP-HIS6—FMP37t-TerCaMV35S, will be transferred to the greenhouse under standard growth conditions. Following a period of acclimation of two weeks, the T0 plants will be treated with a mixture containing 100 g tembotrione/ha prepared from a WP20 (wettable powder 20%) formulation supplemented with ammonium sulfate and methyl ester raps oil. Two weeks after the treatment, the symptoms due to the application of the herbicides will be evaluated. The plants are classified in four categories. The treated plants evaluated as "0" are looking like the untreated tobacco plants. The plants evaluated as "1" display temporary light bleaching phenotype due to the application of the herbicides. The plants evaluated as "2" display permanent light to strong bleaching symptoms. Finally the plants evaluated as "3" are looking like wild type tobacco plants submitted to the same treatment. The results are summarized in the following table 9.

TABLE 9

Response of T0 tobacco plants expressing the FMP37 HPPD.

| Gene | Number of Transformants obtained on media containing Kanamycin | Categories corresponding to the intensity of symptoms due to the application of Tembotrione at a rate of 100 g AI/ha on the treated plants | | | |
|---|---|---|---|---|---|
| | | 0 | 1 | 2 | 3 |
| FMP37t | 38 | 6 | 10 | 13 | 7 |

In conclusion, several tobacco plants expressing the FMP37 HPPD are tolerant to tembotrione.

Example 6

Cloning of Gene FMP37e, FMP37t and FMP37m Coding for FMP37 HPPD in a Vector to Transform *Zea mays* Plants FMP37e (SEQ ID No. 2), FMP37t (SEQ ID No. 3), FMP37m-h (SEQ ID No. 16)

a—FMP37e in pHoe6/Ac: Gene with a codon usage optimized for *E. coli*, plus at its 5' extremity a sequence coding for OTP and sequence coding for an His TAG.

The vector pRT100-FMP37e containing the gene coding for the HPPD FMP37, optimized for the expression in *E. coli* under the control of the CaMV35S promoter, was digested with the restriction enzyme HindIII.

The CaMV35S::OTP::FMP37e::CaMV35S-term cassette was further cloned into the binary vector pHoe6/Ac (U.S. Pat. No. 6,316,694) previously digested with the same restriction enzyme and dephosphorylated. The resulting vector was called pHoe6/Ac/FMP37e.

b—FMP37t in pHoe6/Ac (SEQ ID No. 3): Gene with a codon usage optimized for dicotyledoneous plants, plus at its 5' extremity a sequence coding for OTP and sequence coding for an His TAG.

FMP37t in pRT100. A version of the gene coding for the protein FMP37 optimized for the expression in *Nicotiana tobaccum* plus containing at the 5' end a nucleic acid sequence encoding an optimized transit peptide and an HIS tag was ordered and called FMP37t. Upstream to this sequence was added the recognition sequence for the restriction enzyme XhoI and downstream the recognition sequence for the restriction enzyme XbaI. The DNA corresponding to the OTP and FMP37t were digested with the restriction enzymes XhoI and XbaI, separated per appropriate gel electrophoresis and cloned into the vector pRT100 (Toepfer, (1987), Nucleic Acid Res 15:5890) previously digested with XhoI and NcoI restriction enzymes. The plasmid pRT100 contains the CaMV35S promoter and CaMV35S terminator. The resulting vector was called pRT100-FMP37t, and digested with the restriction enzyme HindIII to separate the DNA corresponding to CaMV35S::OTP::FMP37t:: CaMV35S-term cassette from the rest of the vector, in order to clone it into the previously restricted vector pHoe6/Ac (U.S. Pat. No. 6,316,694). The resulting vector was called pHoe6/Ac/FMP37t (FIG. 3).

c—FMP37m in pHoe6/Ac (SEQ ID No. 16): Gene with a codon usage optimized for monocotyledoneous plants plus at its 5' extremity a sequence coding for OTP. FMP37m in pRT100-OTP (NcoI-XbaI) then HindIII The variant of the gene optimized for the expression in monocotyledon plants coding for FMP37, called FMP37m was ordered, and upstream of the start codon was added a NcoI restriction site while downstream of the stop codon was added the recognition sequence for the restriction enzyme XbaI. The DNA sequence corresponding to FMP37m was digested with the restriction enzymes NcoI and XbaI, then separated per gel electrophoresis, finally isolated from the gel. The isolated DNA fragment was mixed with the vector pRT100-OTP (mentioned above) previously also digested with the same restriction enzymes. The resulting vector was called pRT100-OTP-FMP37m, containing the expression cassette CaMV35S::OTP::FMP37m::CaMV35Sterm, which was isolated using the restriction enzyme HindIII then further cloned into the previously opened and dephosphorylated vector pHOE6/Ac containing the gene coding for the PAT (Phosphinothricin acetyl transferase) enzyme, conferring resistance to the herbicide glufosinate (U.S. Pat. No. 6,316,694). The resulting plasmid was called pHoe/Ac/FMP37m (FIG. 3F)

Maize Transformation:

The plasmids pHoe6/Ac (U.S. Pat. No. 6,316,694), pHoe6/Ac/FMP37e, pHoe6/Ac/FMP37t and pHoe6/Ac/FMP37m were used to transform maize culture.

The maize culture, protoplast isolation, transformation and regeneration of fertile transgenic maize plants were performed according to the U.S. Pat. No. 6,284,945, *"Zea mays* (L.) with capability of long term, highly efficient plant regeneration including fertile transgenic maize having a heterologous gene, and their preparation"*. Transformed calli were selected on media containing phosphinothricin. Regenerated rooted plants were then transferred to soil, and allow to grow and produce seeds in the glasshouse under standard conditions (28/20° C.). Adult plants were grown until seed production and seeds were collected for further sowing, sufficiently developed plants will be treated with the respective HPPD inhibitor herbicides.

Example 7

Construction of Vector Containing FMP37e Gene to be Expressed into Rice Plants

A binary vector for rice plant transformation is, for example, constructed with the CaMV35 promoter driving the expression of the gene FMP37e, with a codon usage optimized for the expression in *E coli* bacteria and at its 5' extremity was added a sequence coding for an His TAG, and further upstream a sequence coding for an OTP, followed by the CaMV35S terminator. Additionally, the transformation vector also contains a PAT gene cassette in which the gene is driven by a CaVM35S promoter and followed by a CaMV35S terminator for glufosinate based selection during the transformation process (see FIG. 3 I). The binary vector was called pTMV370. A similar binary vector is similarly constructed but comprising an expression cassette expressing the *Arabidopsis* gene coding for the HPPD enzyme.

Example 8

Transformation of Rice Plants

Rice transformation is achieved using methods well known in the art. Briefly, the *Agrobacterium tumefaciens* mediated transformation of rice was performed using immature embryos, from the restorer line 6G4317. Briefly, panicles from donor plants were harvested 8-12 days after pollination. The lemma of the immature seed was removed. Seeds were thereafter sterilized using a NaOCl based solution and Tween. The seeds were preinduced with acetylsalicylic acid. *Agrobacterium tumefaciens* cells were then co-cultivated with the preinduced seeds in presence of acetosyringone for 4 days at 24° C. in the dark. Thereafter, coleoptile from embryos were removed and washed, then put on a media supplemented with phosphinothricin for 3 weeks at 28° C. under a photoperiod rhythm of 16 hours. Then the growing calli were cut off from the embryos, and transferred to fresh media containing triacillin, phosphinothricin, L-proline and copper (II) sulfate.

For each callusline and per Tembotrione concentration, 3 shoots, and randomly isolated from different callus pieces, were transferred to MS/2 with Tembotrione. As a general rule, transfer of the shoots from regeneration medium to MS/2 occurred 9 weeks after calli had been put on regeneration medium.

Cultures were incubated at 26.5° C. (16 hrs. photoperiod) and evaluation of symptoms occurred 2 weeks later.

New developing leaves of the shoots transferred have been scored on the basis of bleaching and categorized in 3 groups:

a) no bleaching b) intermediate bleaching c) complete bleaching

Within the category 'intermediate bleaching' a distinction has been made between shoots having new leaves showing only very little bleaching symptoms and thus tending to green leaves, and shoots with new leaves almost completely bleached.

TABLE 10

| Tembotrione concentration. | | AtHPPD | FMP37e |
|---|---|---|---|
| 1 μM | N° of shoots without bleaching | 27 | 19 |
| | N° of shoots with intermediate bleaching | 19 | 24 |
| | N° of shoots completely bleached | 12 | 17 |
| 5 μM | N° of shoots without bleaching | 0 | 0 |
| | N° of shoots with intermediate bleaching | 2 | 17 |
| | N° of shoots completely bleached | 58 | 43 |

T0 rooted plantlets were transferred to soil in the glasshouse. Following an acclimation period, sufficiently grown plants were treated with the different HPPD inhibitor herbicides. As an example, T0 plants were sprayed with tembotrione WP20 100 g AI/ha supplemented with ammonium sulfate and methyl ester raps oil. Seven days after the spray application, the symptoms due to the application of the herbicide were evaluated and compared the symptoms observed on wild type plants submitted to the same treatment.

Response to Tembotrione in Glasshouse Trials.

T0 rooted plantlets (either selected on phosphinothricin alone or on phosphinothricin supplemented with tembotrione) were transferred to soil in the glasshouse. Following an acclimation period, sufficiently grown plants were treated with the different HPPD inhibitor herbicides. As an example, T0 plants were sprayed with tembotrione of formulation type WP20 100 g AI/ha supplemented with ammonium sulfate and methyl ester raps oil. Seven days after the spray application, the symptoms due to the application of the herbicide were evaluated and compared the symptoms observed on wild type plants submitted to the same treatment.

The plants were classified in three categories based on the phenotype developed in response to the herbicide seven days after the treatment. Class I was defined as plants displayed no injuries, ClassII was defined as plants displayed temporary light injuries in response to the herbicide treatment (injury: 10-40%), Class III was defined as plants displaying strong injuries to similar injuries as seen with wild type plants submitted to the same treatment (injury: 41-100%).

In general, it can be seen that even the plants containing only one T-DNA insert already showed up a significant and sufficient level of tolerance to an exposed field dose of the HPPD inhibitor herbicide tembotrione.

TABLE 11

| Transgene | Number of treated plants | Tembotrione, 100 g AI/ha 7 DAT | | |
|---|---|---|---|---|
| | | Class I | Class II | Class III |
| — | 20 | 0 | 0 | 20 |
| AtHPPD | 23 | 1 | 13 | 9 |
| FMP37e | 23 | 1 | 6 | 16 |

In conclusion, it can be seen that the rice plants expressing the protein FMP37 are more tolerant to the application of the HPPD inhibitor herbicide tembotrione than the wild type rice plants.

Example 9

Construction of Binary Soybean Transformation Vectors

A binary vector for soybean transformation is, for example, constructed with the CaMV35 promoter driving the expression of the gene FMP37t-h (SEQ ID No. 15), with a codon usage optimized for the expression in dicotyledoneous plants and at its 5' extremity was added a sequence coding for an OTP, and further upstream a sequence TEV (Tobacco etch virus) to improve the stability of the mRNA in plants followed by the CaMV35S terminator. The nucleotide sequence of the gene FMP37t-h is given in SEQ ID No. 15. Additionally, the transformation vector also contains a PAT gene cassette in which the gene is driven by a CaVM35S promoter and followed by a CaMV35S terminator for glufosinate based selection during the transformation process and a 2mEPSPS gene cassette in which the gene is driven by an histone promoter from *Arabidopsis* to confer tolerance to the herbicide glyphosate to the transformed plants (see FIG. 3 H). The binary vector was called pFCO112.

Example 10

Soybean T0 Plant Establishment and Selection

Soybean transformation is achieved using methods well known in the art, such as the one described using the *Agrobacterium tumefaciens* mediated transformation soybean half-seed explants described by Paz et al. (2006, Plant cell Rep. 25:206). Transformants were identified using Isoxaflutole as selection marker. The appearance of green shoots was observed, and documented as an indicator of tolerance to the herbicide isoxaflutole. In total, 1.5% of the transgenic tested shoots showed normal greening comparable to wild-type soybean shoots not treated with isoxaflutole, whereas wild-type soybean shoots treated with the same amount of isoxaflutole were entirely bleached. This indicates that the presence of FMP37 protein enables the tolerance to HPPD inhibitor herbicides, like isoxaflutole.

Tolerant green shoots were transferred to rooting media or grafted. Rooted plantlets were transferred to the glasshouse after an acclimation period.

Plants containing the transgene were then sprayed with HPPD inhibitor herbicides, as for example with tembotrione at a rate of 100 g AI/ha. Ten days after the application the symptoms due to the application of the herbicide were evaluated and compared to the symptoms observed on a wild type plants under the same conditions.

Eight events expressing the FMP37 HPPD protein have been generated from the green shoots of above and were transferred to the greenhouse. Four weeks after acclimation, i.e. plants at a developmental stage of 3-4 internodes were treated with 100 g AI/ha tembotrione prepared from a WP 20 formulation supplemented with ammonium sulfate and methyl ester raps oil. Ten days after application, the symptoms caused by the application of the HPPD inhibitor herbicide were evaluated and compared to the symptoms observed on treated non-transgenic wild-type soybean plants. Four of the eight events didn't show any bleaching phenotype and looked like non-treated wild-type soybean plants. One event showed transitory light bleaching symptoms but recovered 14 days after tembotrione application. One other event showed local transitory bleaching symptoms but recovered completely 7 days after tembotrione application. The remaining two events exhibited the bleaching like non-transgenic wild-type soybean plant after treatment with tembotrione. All these data confirm that FMP37 confers tolerance to HPPD inhibitor herbicides, like tembotrione, in soybean plants.

Example 11

Construction of Binary Cotton Transformation Vectors

A binary vector for cotton transformation is, for example, constructed with the CaMV35 promoter driving the expression of the gene FMP37t-h (SEQ ID No. 15), with a codon usage optimized for the expression in dicotyledoneous plants and at its 5' extremity was added a sequence coding for an OTP, and further upstream a sequence TEV (Tobacco etch virus) to improve the stability of the mRNA in plants followed by the CaMV35S terminator. The nucleotide sequence of the gene FMP37t-h is given in SEQ ID No. 15. Additionally, the transformation vector also contains a PAT gene cassette in which the gene is driven by a CaVM35S promoter and followed by a CaMV35S terminator for glufosinate based selection during the transformation process and a 2mEPSPS gene cassette in which the gene is driven by an histone promoter from *Arabidopsis* to confer tolerance to the herbicide glyphosate to the transformed plants (see FIG. 3 J). The binary vector was called pTSIH21.

Example 12

Cotton T0 Plant Establishment and Selection

Cotton transformation is achieved using methods well known in the art, especially preferred method in the one described in the PCT patent publication WO 00/71733.

Regenerated plants are transferred to the glasshouse. Following an acclimation period, sufficiently grown plants are sprayed with HPPD inhibitor herbicides as for example tembotrione 100 g AI/ha supplemented with ammonium sulfate and methyl ester raps oil. Seven days after the spray application, the symptoms due to the treatment with the herbicide are evaluated and compared to the symptoms observed on wild type cotton plants subjected to the same treatment under the same conditions.

Example 13

Construction of Binary Transformation Vectors to Generate Plants Tolerant to Four Herbicides with Distinct Modes of Action A binary vector for dicotyledoneous plant transformation is, for example, constructed with the CaMV35 promoter driving the expression of the gene FMP37t-h (SEQ ID No. 15), with a codon usage optimized for the expression in dicotyledoneous plants and at its 5'-extremity was added a sequence coding for an OTP followed by the CaMV35S terminator. The nucleotide sequence of the gene FMP37t-h is given in SEQ ID No. 15. Additionally, the transformation vector also contains a PAT gene cassette in which the gene is driven by a CaVM35S promoter and followed by a CaMV35S terminator to confer tolerance to glufosinate to the plant expressing the gene, a 2mEPSPS gene cassette coding for the double mutant (Thr102Ile and Pro106Ser) EPSPS in which the gene is driven by an histone promoter from *Arabidopsis* to confer tolerance to the herbicide glyphosate to the transformed plants, and an *Arabidopsis thaliana* 2 mAHAS gene cassette encoding a tolerant ALS enzyme (Acetolactate synthase, Pro197Ala, Trp574Leu) driven by a CaMV35S promoter to confer tolerance to herbicides from the sulfonylurea or imidazolinone classes to the plant expressing this gene (see FIG. 3 G). The gene cassettes is finally cloned into the vector pHoe6/Ac (U.S. Pat. No. 6,316,694), and the final vector is called pHoe6/FMP37t-h/PAT/EPSPS/AHAS, and is used to transform dicotyledoneous plants via *Agrobacterium tumefaciens* mediated state of the art methods. T0 plants are transferred to soil, and after an acclimation period, sufficiently grown plants are sprayed successively with an herbicide from the HPPD inhibitor class, then with glyphosate, then with glufosinate and finally with an herbicide from the sulfonylurea class for example.

Example 14

Generation of Transgenic Plants Showing Tolerance to Herbicides of Three Different Mode of Action A binary vector for tobacco transformation is, for example, constructed with the CaMV35 promoter driving the expression of the gene FMP37t-h (SEQ ID No. 15), with a codon usage optimized for the expression in dicotyledoneous plants and at its 5' extremity was added a sequence coding for an OTP, and further upstream a sequence TEV (Tobacco etch virus) to improve the stability of the mRNA in plants followed by the CaMV35S terminator. The nucleotide sequence of the gene FMP37t-h is given in SEQ ID No. 15. Additionally, the transformation vector also contains a PAT gene cassette in which the gene is driven by a CaVM35S promoter and followed by a CaMV35S terminator for glufosinate based selection during the transformation process and a 2mEPSPS gene cassette in which the gene is driven by an histone promoter from *Arabidopsis* to confer tolerance to the herbicide glyphosate to the transformed plants (see FIG. 3 H). The binary vector was called pFCO112. The above vector was used to transform leaf disks obtained from *Nicotiana tobacum* plants, according to Example 3.

Transgenic tobacco plants were transferred to the greenhouse and treated with glyphosate at a rate of 1121 g AI/ha. Seeds were produced from such tolerant tobacco plants and harvested. These seeds were put on soil to germinate in the glasshouse. Three to four weeks later, 50 plantlets per event were transferred to single pots. Two weeks later, plants of a size 4-6 cm were sprayed either with:

| | |
|---|---|
| glufosinate-ammonium | 1000 gAI/ha, |
| glyphosate | 1121 gAI/ha, |
| tembotrione | 100 g AI/ha, or |
| tembotrione + glyphosate | 100 g AI/ha + 1121 gAI/ha |

After nine days, the symptoms caused by the respective herbicide applications were evaluated as summarized in Table 12, below.

The plants were classified in three categories based on the phenotype developed in response to the respective herbicide(s) seven days after the treatment. Class I was defined as plants displayed no injuries, Class II was defined as plants displayed temporary light injuries in response to the herbicide treatment (injury: 10-40%), Class III was defined as plants displaying strong injuries to similar injuries as seen with wild type plants submitted to the same treatment (injury: 41-100%). Non-transgenic tobacco plants were completely killed by treatment using one or more of the above herbicides.

TABLE 12

| Transgene | Line | Class I | Class II | Class III |
|---|---|---|---|---|
| | | Glufosinate-ammonium 1000 g AI/ha 9 DAT | | |
| FMP37t-h | 634 | 10 | 0 | 0 |
| FMP37t-h | 713 | 10 | 0 | 0 |
| | | Glyphosate 1121 g AI/ha 9 DAT | | |
| FMP37t-h | 634 | 10 | 0 | 0 |
| FMP37t-h | 713 | 10 | 0 | 0 |
| | | Tembotrione 100 g AI/ha 9 DAT | | |
| FMP37t-h | 634 | 0 | 3 | 7 |
| FMP37t-h | 713 | 0 | 6 | 4 |
| | | Glyphosate + tembotrione 1121 g AI/ha + 100 g AI/ha 9 DAT | | |
| FMP37t-h | 634 | 0 | 5 | 5 |
| FMP37t-h | 713 | 0 | 2 | 8 |

All these data confirm that these plants encoding several tolerance genes concerning HPPD inhibitor herbicides, glyphosate and glufosinate-ammonium confer tolerance to any of these herbicides applied alone or in combination with each other.

This is the first time that transgenic plants containing these three tolerance genes at a single locus exhibit an herbicide tolerance to such herbicides at an application rate which is of agronomical relevance.

The invention claimed is:

1. A method for controlling weeds in an area or a field which contains a plant or a seed, which method comprises applying, to the area or the field, a dose of an HPPD inhibitor herbicide which is toxic for said weeds, without significantly affecting the seed or plant, wherein the plant or the seed comprises a chimeric gene comprising a coding sequence operably linked to a plant-expressible promoter, the coding sequence comprises a nucleic acid sequence which encodes a *Blepharisma japonicum* hydroxyphenylpyruvate dioxygenase (HPPD) protein according to SEQ ID No. 4 from amino acid position 2 to amino acid position 382.

2. The method for controlling weeds according to claim 1, characterized in that the HPPD inhibitor herbicide is selected from the group consisting of isoxaflutole, tembotrione, mesotrione, sulcotrione, pyrasulfotole, topramezone, 2-cyano-3-cyclopropyl-1-(2-$SO_2CH_3$-4-$CF_3$phenyl)propane-1,3-dione, 2-cyano-3-cyclopropyl-1-(2-$SO_2CH_3$-4-2,3 $Cl_2$ phenyl)propane-1,3-dione, bicyclopyrone, benzobicyclon, tefuryltrione, diketonitrile, and pyrazoxyfen.

3. A method for obtaining oil or meal comprising growing a plant comprising a chimeric gene comprising a coding sequence operably linked to a plant-expressible promoter, the coding sequence comprises a nucleic acid sequence which encodes a *Blepharisma japonicum* hydroxyphenylpyruvate dioxygenase (HPPD) protein according to SEQ ID No. 4 from amino acid position 2 to amino acid position 382 treating the plant with an HPPD inhibitor herbicide, harvesting grains from the plant, and milling the grains to make meal, and optionally extracting oil from the grains.

4. The method of claim 1, wherein the method is for controlling weeds in an area or a field which contains said plant.

5. The method of claim 1, wherein the method is for controlling weeds in an area or a field which contains said seed.

6. The method of claim 1, wherein the chimeric gene comprises the nucleotide sequence of SEQ ID No. 1 from nucleotide position 4 to nucleotide position 1149, or SEQ ID No. 3 from nucleotide position 400 to nucleotide position 1542.

7. The method of claim 1, wherein the chimeric gene comprises, upstream of the HPPD coding sequence, a nucleic acid sequence which encodes a transit peptide active in plants so that a transit peptide/HPPD fusion protein is encoded by said chimeric gene.

8. The method of claim 1, wherein the plant or the seed further comprises a chimeric gene encoding a prephenate dehydrogenase (PDH) enzyme.

9. The method of claim 1, wherein the plant or the seed further comprises one or more chimeric genes conferring tolerance to
   (a) a growth regulator herbicide; or
   (b) a herbicide inhibiting enzyme, wherein the enzyme is selected from the group consisting of (i) acetolactate synthase, (ii) 5-enolpyruvylshikimate (EPSP) synthase and (iii) glutamine synthase; or
   (c) a combination thereof.

10. The method of claim 9, wherein the growth regulator herbicide is selected from the group consisting of 2,4-D and dicamba.

11. The method of claim 3, wherein the plant is selected from the group consisting of soya, corn, cotton, and grain.

* * * * *

SEQUENCE LISTING

<160> NUMBER OF SEQ ID NOS: 23

<210> SEQ ID NO 1
<211> LENGTH: 1149
<212> TYPE: DNA
<213> ORGANISM: Blepharisma japonicum

<400> SEQUENCE: 1

```
atgacttatt acgacaagca agaaacgcgt ccagatcttg gcgaattcta tggtttccat      60
cacgttcgtt tttacgtctc caactcagag caagccgctt cgttctacac atctcgcttt     120
gggttttctc cggttgccta tgaaggattg gaaacaggaa accaaaaatt ctgtaccaat     180
gtcgtccgaa gcaaccatgt agtcatcgct tttacctcag ctctcactcc tgaagacaat     240
gaagtgaacc gtcacgttgg caagcatagt gatggagttc aagacattgc ctttagtgta     300
agtgacgcaa gagggatgta tgagaaagcg atagctaaag gctgtaaaag cttccgtgag     360
ccacaggttt tacaagatca atttggatct gttataatag cgtctctcca gacttatgga     420
gacactgttc acacattagt ccaaaatgtc gactatacag gacccttttt gcctggcttc     480
agagcaatca caaagatga tccattaaac tctgcctttc ctcaggtaaa ttatgacatt     540
attgatcatg ttgtaggaaa tcagcctggt ggcgatatga ctcctacagt agaatggtat     600
gagaaatatc tagaatttca tcgatattgg tctgctgatg agtctgtaat ccataccgat     660
tattcagcat taaggtctgt tgtggttgct gattgggatg aagtgatcaa aatgcctatt     720
aatgagcctg ctgatggact tagaaaaagt caaatccaag aatatgtcga atattatggt     780
ggagcaggcg tacaacatat tgccttaaaa gtcaatgata ttatttcagt aataagcacc     840
ttaagggcta gaggtgtgga attcttagaa gttcctccta aatattatga tagcttaaga     900
aaaagacttg cgcattctgc ggtacaaatt gaagaagact aaaaagaat tgaagacctt     960 catattttgg ttgactttga cgaccgtggg tatttacttc agattttcac aaaaccagta    1020
gaagacagac ctactctgtt ttatgaaatt attcaaagac ataataacaa tggattcgga    1080
attggaaatt ttaaagcccct atttgaatca ttggaacaag agcaagaaag aagaggtaat    1140
ttgatctaa                                                            1149
```

<210> SEQ ID NO 2
<211> LENGTH: 1170
<212> TYPE: DNA
<213> ORGANISM: Artificial sequence
<220> FEATURE:
<223> OTHER INFORMATION: Nucleic acid sequence encoding Blepharisma japonicum HPPD optimized for E. coli, containing at the 5' end a nucleic acid encoding an alanine and 6 histidine amino acids.
<220> FEATURE:
<221> NAME/KEY: misc_feature
<222> LOCATION: (4)..(6)
<223> OTHER INFORMATION: Sequence coding for Ala
<220> FEATURE:
<221> NAME/KEY: misc_feature
<222> LOCATION: (7)..(24)
<223> OTHER INFORMATION: Sequence encoding an His tag containing 6 His
<220> FEATURE:
<221> NAME/KEY: misc_feature
<222> LOCATION: (7)..(24)
<223> OTHER INFORMATION: Sequence encoding an HIS Tag containing 6 HIS

<400> SEQUENCE: 2

```
atggcgcatc atcatcacca tcacacgtat tatgacaaac aggaaacccg ccctgatctg      60
ggagagtttt atggctttca ccacgtacgc ttttacgtga gcaatagtga gcaagctgcc     120
agcttttaca cgtcacgctt tgggttttct ccagtggcct atgaaggcct ggaaaccggt     180
aaccagaagt tctgtacgaa cgtggtacgc agcaatcatg tggtgatagc gtttaccagt     240
gctctgactc ccgaagacaa cgaagttaac cggcatgtag gcaaacattc ggatggcgtt     300
caggatattg cgtttagtgt gtctgatgct cgtgggatgt acgagaaagc catagcgaaa     360
ggctgcaaat cctttcgcga accccaagta ctgcaagatc agtttggtag cgttatcatt     420
```

```
gcctccctcc agacatatgg tgatacagtg catacgcttg ttcaaaacgt tgactatact    480
ggtccgttct taccgggttt tcgcgctatt accaaagacg atccgctcaa ttcggcgttc    540
ccacaagtga actatgacat catcgatcac gtggtgggta atcagccggg tggagatatg    600 accccctactg tggaatggta cgaaaagtat ctcgaattcc accgctactg gagtgccgat    660
gaaagcgtca ttcacaccga ttatagcgcg ttacggtcgg ttgtcgtagc cgactgggat    720
gaagtgatca aaatgccgat taacgaacca gcggatggct tgcgtaagtc gcagattcag    780
gagtatgtcg agtactatgg tggggcagga gtgcaacata tcgcactgaa agtcaatgac    840
atcatttccg tcatctcaac gttgcgtgca cgtggcgttg agttcctgga agttccgccg    900
aagtactatg atagccttcg caaacgcctg gcacattcag cggtccagat cgaagaagac    960
ctgaaacgta ttgaggactt gcatattctg gttgatttcg acgatcgtgg ttaccttta    1020 cagattttca ccaaaccggt cgaagatcgt cctaccctgt tctacgagat cattcagcgc   1080
cacaataaca atggctttgg cattggcaac ttcaaagcac tgtttgaatc tctggagcaa   1140
gaacaggaac gtcgcgggaa tctgatctaa                                   1170

<210> SEQ ID NO 3
<211> LENGTH: 1545
<212> TYPE: DNA
<213> ORGANISM: Artificial sequence
<220> FEATURE:
<223> OTHER INFORMATION: Nucleic acid sequence encoding Blepharisma
      japonicum HPPD optimized for Nicotiana tobaccum containing at the
      5' end a nucleic acid sequence encoding an optimized transit
      peptide and an HIS Tag
<220> FEATURE:
<221> NAME/KEY: transit_peptide
<222> LOCATION: (1)..(375)
<223> OTHER INFORMATION: Optimized transit peptide to chloroplasts
<220> FEATURE:
<221> NAME/KEY: misc_feature
<222> LOCATION: (376)..(378)
<223> OTHER INFORMATION: sequence encoding a Met
<220> FEATURE:
<221> NAME/KEY: misc_feature
<222> LOCATION: (379)..(381)
<223> OTHER INFORMATION: sequence encoding an Ala
<220> FEATURE:
<221> NAME/KEY: misc_feature
<222> LOCATION: (382)..(399)
<223> OTHER INFORMATION: sequence encoding an HIS Tag made of 6 HIS

<400> SEQUENCE: 3
atggcttcta tttcttcttc tgtggctact gtttctagga ctgctccagc tcaagctaat     60
atggtggctc cattcacagg cttgaaatcc aatgctgctt tcccaactac taagaaggct    120
aacgatttct ctactctccc atctaatggt ggaagggttc agtgtatgca agtttggcca    180
gcttacggaa ataagaagtt cgagactctt tcttaccttc caccactttc tatggctcca    240
actgtgatga tggcttcttc tgctactgct gttgctccat ccaaggatt gaagtctact    300 gcttctttgc cagttgctag aaggtcatct cgttctcttg aaacgtttc taacggtgga    360 aggattagat gtgctatggc tcatcatcat caccatcaca cttactacga taagcaagag    420
actagaccag atcttggaga gttctacgga ttccaccatg ttaggttcta cgtgtctaat    480
tctgagcaag ctgcttcttt ctacacttcc cgtttcggat tttctccagt tgcttacgaa    540
ggacttgaga ctggaaatca gaagttctgc actaacgttg ttaggtctaa ccacgtggtg    600 attgcttta cttctgctct cactccagag gataatgagg ttaacaggca tgttggaaag    660
cactctgatg gtgttcagga tattgctttc tctgtgtctg atgctagagg aatgtacgag    720
```

```
aaggctattg ctaagggatg caagtctttc agagagccac aagttcttca agatcagttc    780
ggatccgtga ttattgcttc ccttcagact tacggtgata ctgttcacac tctcgttcag    840
aacgttgatt acactggacc attccttcca ggtttcaggg ctatcactaa ggatgatcca    900
cttaactctg ctttcccaca ggtgaactac gatatcattg atcacgttgt gggaaatcag    960
ccaggtggag atatgactcc aactgttgag tggtacgaga agtaccttga gtttcacagg   1020
tattggagtg ctgatgagtc tgtgatccac actgattact ctgctcttag atctgttgtt   1080
gtggctgatt gggatgaggt tatcaagatg cctattaacg aaccagctga tggacttagg   1140
aagtcccaga ttcaagagta cgttgagtat tatggtggag ctggtgttca acacattgct   1200
ctcaaggtga acgatatcat ttccgtgatt ccactctta  gagctagagg agttgagttt   1260
cttgaagtcc caccaaagta ctacgattct ctcagaaaga ggcttgctca ttctgctgtt   1320
cagatcgaag aggatcttaa acgtattgag gaccttcaca tcctcgtgga ttttgatgat   1380
agggatacc  ttctccagat tttcactaag ccagttgagg ataggccaac tttgttctac   1440
gagatcatcc aaaggcataa caacaacgga ttcggaatcg gaaatttcaa ggctcttttc   1500
gagtctcttg agcaagaaca agagagaagg ggaaacctca tctga                   1545
```

<210> SEQ ID NO 4
<211> LENGTH: 382
<212> TYPE: PRT
<213> ORGANISM: Blepharisma japonicum

<400> SEQUENCE: 4

```
Met Thr Tyr Tyr Asp Lys Gln Glu Thr Arg Pro Asp Leu Gly Glu Phe
1               5                   10                  15

Tyr Gly Phe His His Val Arg Phe Tyr Val Ser Asn Ser Glu Gln Ala
            20                  25                  30

Ala Ser Phe Tyr Thr Ser Arg Phe Gly Phe Ser Pro Val Ala Tyr Glu
        35                  40                  45

Gly Leu Glu Thr Gly Asn Gln Lys Phe Cys Thr Asn Val Val Arg Ser
    50                  55                  60

Asn His Val Val Ile Ala Phe Thr Ser Ala Leu Thr Pro Glu Asp Asn
65                  70                  75                  80

Glu Val Asn Arg His Val Gly Lys His Ser Asp Gly Val Gln Asp Ile
                85                  90                  95

Ala Phe Ser Val Ser Asp Ala Arg Gly Met Tyr Glu Lys Ala Ile Ala
            100                 105                 110

Lys Gly Cys Lys Ser Phe Arg Glu Pro Gln Val Leu Gln Asp Gln Phe
        115                 120                 125

Gly Ser Val Ile Ile Ala Ser Leu Gln Thr Tyr Gly Asp Thr Val His
    130                 135                 140

Thr Leu Val Gln Asn Val Asp Tyr Thr Gly Pro Phe Leu Pro Gly Phe
145                 150                 155                 160

Arg Ala Ile Thr Lys Asp Asp Pro Leu Asn Ser Ala Phe Pro Gln Val
                165                 170                 175

Asn Tyr Asp Ile Ile Asp His Val Val Gly Asn Gln Pro Gly Gly Asp
            180                 185                 190

Met Thr Pro Thr Val Glu Trp Tyr Glu Lys Tyr Leu Glu Phe His Arg
        195                 200                 205

Tyr Trp Ser Ala Asp Glu Ser Val Ile His Thr Asp Tyr Ser Ala Leu
    210                 215                 220
```

```
Arg Ser Val Val Val Ala Asp Trp Asp Glu Val Ile Lys Met Pro Ile
225                 230                 235                 240

Asn Glu Pro Ala Asp Gly Leu Arg Lys Ser Gln Ile Gln Glu Tyr Val
            245                 250                 255

Glu Tyr Tyr Gly Gly Ala Gly Val Gln His Ile Ala Leu Lys Val Asn
                260                 265                 270

Asp Ile Ile Ser Val Ile Ser Thr Leu Arg Ala Arg Gly Val Glu Phe
            275                 280                 285

Leu Glu Val Pro Pro Lys Tyr Tyr Asp Ser Leu Arg Lys Arg Leu Ala
        290                 295                 300

His Ser Ala Val Gln Ile Glu Glu Asp Leu Lys Arg Ile Glu Asp Leu
305                 310                 315                 320

His Ile Leu Val Asp Phe Asp Asp Arg Gly Tyr Leu Leu Gln Ile Phe
                325                 330                 335

Thr Lys Pro Val Glu Asp Arg Pro Thr Leu Phe Tyr Glu Ile Ile Gln
            340                 345                 350

Arg His Asn Asn Asn Gly Phe Gly Ile Gly Asn Phe Lys Ala Leu Phe
        355                 360                 365

Glu Ser Leu Glu Gln Glu Gln Glu Arg Arg Gly Asn Leu Ile
370                 375                 380
```

<210> SEQ ID NO 5
<211> LENGTH: 389
<212> TYPE: PRT
<213> ORGANISM: Artificial sequence
<220> FEATURE:
<223> OTHER INFORMATION: Protein encoded by SEQ ID No. 2
<220> FEATURE:
<221> NAME/KEY: MISC_FEATURE
<222> LOCATION: (2)..(2)
<223> OTHER INFORMATION: Ala
<220> FEATURE:
<221> NAME/KEY: MISC_FEATURE
<222> LOCATION: (3)..(8)
<223> OTHER INFORMATION: HIS Tag made of 6 HIS

<400> SEQUENCE: 5

```
Met Ala His His His His His His Thr Tyr Tyr Asp Lys Gln Glu Thr
1               5                   10                  15

Arg Pro Asp Leu Gly Glu Phe Tyr Gly Phe His His Val Arg Phe Tyr
            20                  25                  30

Val Ser Asn Ser Glu Gln Ala Ala Ser Phe Tyr Thr Ser Arg Phe Gly
        35                  40                  45

Phe Ser Pro Val Ala Tyr Glu Gly Leu Glu Thr Gly Asn Gln Lys Phe
    50                  55                  60

Cys Thr Asn Val Val Arg Ser Asn His Val Val Ile Ala Phe Thr Ser
65                  70                  75                  80

Ala Leu Thr Pro Glu Asp Asn Glu Val Asn Arg His Val Gly Lys His
                85                  90                  95

Ser Asp Gly Val Gln Asp Ile Ala Phe Ser Val Ser Asp Ala Arg Gly
            100                 105                 110

Met Tyr Glu Lys Ala Ile Ala Lys Gly Cys Lys Ser Phe Arg Glu Pro
        115                 120                 125

Gln Val Leu Gln Asp Gln Phe Gly Ser Val Ile Ile Ala Ser Leu Gln
    130                 135                 140

Thr Tyr Gly Asp Thr Val His Thr Leu Val Gln Asn Val Asp Tyr Thr
145                 150                 155                 160

Gly Pro Phe Leu Pro Gly Phe Arg Ala Ile Thr Lys Asp Asp Pro Leu
```

```
                    165                 170                 175
Asn Ser Ala Phe Pro Gln Val Asn Tyr Asp Ile Ile Asp His Val Val
                180                 185                 190
Gly Asn Gln Pro Gly Gly Asp Met Thr Pro Thr Val Glu Trp Tyr Glu
                195                 200                 205
Lys Tyr Leu Glu Phe His Arg Tyr Trp Ser Ala Asp Glu Ser Val Ile
            210                 215                 220
His Thr Asp Tyr Ser Ala Leu Arg Ser Val Val Ala Asp Trp Asp
225                 230                 235                 240
Glu Val Ile Lys Met Pro Ile Asn Glu Pro Ala Asp Gly Leu Arg Lys
                245                 250                 255
Ser Gln Ile Gln Glu Tyr Val Glu Tyr Tyr Gly Ala Gly Val Gln
                260                 265                 270
His Ile Ala Leu Lys Val Asn Asp Ile Ile Ser Val Ile Ser Thr Leu
            275                 280                 285
Arg Ala Arg Gly Val Glu Phe Leu Glu Val Pro Pro Lys Tyr Tyr Asp
        290                 295                 300
Ser Leu Arg Lys Arg Leu Ala His Ser Ala Val Gln Ile Glu Glu Asp
305                 310                 315                 320
Leu Lys Arg Ile Glu Asp Leu His Ile Leu Val Asp Phe Asp Asp Arg
                325                 330                 335
Gly Tyr Leu Leu Gln Ile Phe Thr Lys Pro Val Glu Asp Arg Pro Thr
            340                 345                 350
Leu Phe Tyr Glu Ile Ile Gln Arg His Asn Asn Asn Gly Phe Gly Ile
            355                 360                 365
Gly Asn Phe Lys Ala Leu Phe Glu Ser Leu Glu Gln Glu Gln Glu Arg
        370                 375                 380
Arg Gly Asn Leu Ile
385

<210> SEQ ID NO 6
<211> LENGTH: 507
<212> TYPE: PRT
<213> ORGANISM: Artificial sequence
<220> FEATURE:
<223> OTHER INFORMATION: Blepharisma japonicum HPPD amino acid sequence
      (SEQ ID No. 4) fused with OTP (optimized transit peptide (WO
      2009/144079))
<220> FEATURE:
<221> NAME/KEY: TRANSIT
<222> LOCATION: (1)..(125)
<223> OTHER INFORMATION: Optimized transit peptide to chloroplasts

<400> SEQUENCE: 6

Met Ala Ser Ile Ser Ser Ser Val Ala Thr Val Ser Arg Thr Ala Pro
1               5                   10                  15
Ala Gln Ala Asn Met Val Ala Pro Phe Thr Gly Leu Lys Ser Asn Ala
                20                  25                  30
Ala Phe Pro Thr Thr Lys Lys Ala Asn Asp Phe Ser Thr Leu Pro Ser
            35                  40                  45
Asn Gly Gly Arg Val Gln Cys Met Gln Val Trp Pro Ala Tyr Gly Asn
        50                  55                  60
Lys Lys Phe Glu Thr Leu Ser Tyr Leu Pro Leu Ser Met Ala Pro
65                  70                  75                  80
Thr Val Met Met Ala Ser Ser Ala Thr Ala Val Ala Pro Phe Gln Gly
                85                  90                  95
Leu Lys Ser Thr Ala Ser Leu Pro Val Ala Arg Arg Ser Ser Arg Ser
```

```
            100                 105                 110
Leu Gly Asn Val Ser Asn Gly Gly Arg Ile Arg Cys Ala Met Thr Tyr
        115                 120                 125

Tyr Asp Lys Gln Glu Thr Arg Pro Asp Leu Gly Glu Phe Tyr Gly Phe
        130                 135                 140

His His Val Arg Phe Tyr Val Ser Asn Ser Glu Gln Ala Ala Ser Phe
145                 150                 155                 160

Tyr Thr Ser Arg Phe Gly Phe Ser Pro Val Ala Tyr Glu Gly Leu Glu
                165                 170                 175

Thr Gly Asn Gln Lys Phe Cys Thr Asn Val Val Arg Ser Asn His Val
        180                 185                 190

Val Ile Ala Phe Thr Ser Ala Leu Thr Pro Glu Asp Asn Glu Val Asn
        195                 200                 205

Arg His Val Gly Lys His Ser Asp Gly Val Gln Asp Ile Ala Phe Ser
        210                 215                 220

Val Ser Asp Ala Arg Gly Met Tyr Glu Lys Ala Ile Ala Lys Gly Cys
225                 230                 235                 240

Lys Ser Phe Arg Glu Pro Gln Val Leu Gln Asp Gln Phe Gly Ser Val
                245                 250                 255

Ile Ile Ala Ser Leu Gln Thr Tyr Gly Asp Thr Val His Thr Leu Val
                260                 265                 270

Gln Asn Val Asp Tyr Thr Gly Pro Phe Leu Pro Gly Phe Arg Ala Ile
        275                 280                 285

Thr Lys Asp Asp Pro Leu Asn Ser Ala Phe Pro Gln Val Asn Tyr Asp
        290                 295                 300

Ile Ile Asp His Val Val Gly Asn Gln Pro Gly Gly Asp Met Thr Pro
305                 310                 315                 320

Thr Val Glu Trp Tyr Glu Lys Tyr Leu Glu Phe His Arg Tyr Trp Ser
                325                 330                 335

Ala Asp Glu Ser Val Ile His Thr Asp Tyr Ser Ala Leu Arg Ser Val
                340                 345                 350

Val Val Ala Asp Trp Asp Glu Val Ile Lys Met Pro Ile Asn Glu Pro
        355                 360                 365

Ala Asp Gly Leu Arg Lys Ser Gln Ile Gln Glu Tyr Val Glu Tyr Tyr
        370                 375                 380

Gly Gly Ala Gly Val Gln His Ile Ala Leu Lys Val Asn Asp Ile Ile
385                 390                 395                 400

Ser Val Ile Ser Thr Leu Arg Ala Arg Gly Val Glu Phe Leu Glu Val
                405                 410                 415

Pro Pro Lys Tyr Tyr Asp Ser Leu Arg Lys Arg Leu Ala His Ser Ala
                420                 425                 430

Val Gln Ile Glu Glu Asp Leu Lys Arg Ile Glu Asp Leu His Ile Leu
        435                 440                 445

Val Asp Phe Asp Asp Arg Gly Tyr Leu Leu Gln Ile Phe Thr Lys Pro
        450                 455                 460

Val Glu Asp Arg Pro Thr Leu Phe Tyr Glu Ile Ile Gln Arg His Asn
465                 470                 475                 480

Asn Asn Gly Phe Gly Ile Gly Asn Phe Lys Ala Leu Phe Glu Ser Leu
                485                 490                 495

Glu Gln Glu Gln Glu Arg Arg Gly Asn Leu Ile
                500                 505
```

<210> SEQ ID NO 7

```
<211> LENGTH: 514
<212> TYPE: PRT
<213> ORGANISM: Artificial sequence
<220> FEATURE:
<223> OTHER INFORMATION: Protein encoded by SEQ ID No. 3
<220> FEATURE:
<221> NAME/KEY: TRANSIT
<222> LOCATION: (1)..(125)
<223> OTHER INFORMATION: Optimized transit peptide to chloroplasts
<220> FEATURE:
<221> NAME/KEY: MISC_FEATURE
<222> LOCATION: (127)..(127)
<223> OTHER INFORMATION: Ala
<220> FEATURE:
<221> NAME/KEY: MISC_FEATURE
<222> LOCATION: (128)..(133)
<223> OTHER INFORMATION: HIS Tag made of 6 HIS

<400> SEQUENCE: 7
```

Met Ala Ser Ile Ser Ser Val Ala Thr Val Ser Arg Thr Ala Pro
1               5                   10                  15

Ala Gln Ala Asn Met Val Ala Pro Phe Thr Gly Leu Lys Ser Asn Ala
            20                  25                  30

Ala Phe Pro Thr Thr Lys Lys Ala Asn Asp Phe Ser Thr Leu Pro Ser
        35                  40                  45

Asn Gly Gly Arg Val Gln Cys Met Gln Val Trp Pro Ala Tyr Gly Asn
    50                  55                  60

Lys Lys Phe Glu Thr Leu Ser Tyr Leu Pro Pro Leu Ser Met Ala Pro
65                  70                  75                  80

Thr Val Met Met Ala Ser Ser Ala Thr Ala Val Ala Pro Phe Gln Gly
                85                  90                  95

Leu Lys Ser Thr Ala Ser Leu Pro Val Ala Arg Arg Ser Ser Arg Ser
            100                 105                 110

Leu Gly Asn Val Ser Asn Gly Gly Arg Ile Arg Cys Ala Met Ala His
        115                 120                 125

His His His His His Thr Tyr Tyr Asp Lys Gln Glu Thr Arg Pro Asp
    130                 135                 140

Leu Gly Glu Phe Tyr Gly Phe His His Val Arg Phe Tyr Val Ser Asn
145                 150                 155                 160

Ser Glu Gln Ala Ala Ser Phe Tyr Thr Ser Arg Phe Gly Phe Ser Pro
                165                 170                 175

Val Ala Tyr Glu Gly Leu Glu Thr Gly Asn Gln Lys Phe Cys Thr Asn
            180                 185                 190

Val Val Arg Ser Asn His Val Val Ile Ala Phe Thr Ser Ala Leu Thr
        195                 200                 205

Pro Glu Asp Asn Glu Val Asn Arg His Val Gly Lys His Ser Asp Gly
    210                 215                 220

Val Gln Asp Ile Ala Phe Ser Val Ser Asp Ala Arg Gly Met Tyr Glu
225                 230                 235                 240

Lys Ala Ile Ala Lys Gly Cys Lys Ser Phe Arg Glu Pro Gln Val Leu
                245                 250                 255

Gln Asp Gln Phe Gly Ser Val Ile Ile Ala Ser Leu Gln Thr Tyr Gly
            260                 265                 270

Asp Thr Val His Thr Leu Val Gln Asn Val Asp Tyr Thr Gly Pro Phe
        275                 280                 285

Leu Pro Gly Phe Arg Ala Ile Thr Lys Asp Asp Pro Leu Asn Ser Ala
    290                 295                 300

Phe Pro Gln Val Asn Tyr Asp Ile Ile Asp His Val Val Gly Asn Gln
305                 310                 315                 320

```
Pro Gly Gly Asp Met Thr Pro Thr Val Glu Trp Tyr Glu Lys Tyr Leu
            325                 330                 335

Glu Phe His Arg Tyr Trp Ser Ala Asp Glu Ser Val Ile His Thr Asp
        340                 345                 350

Tyr Ser Ala Leu Arg Ser Val Val Ala Asp Trp Asp Glu Val Ile
        355                 360                 365

Lys Met Pro Ile Asn Glu Pro Ala Asp Gly Leu Arg Lys Ser Gln Ile
        370                 375                 380

Gln Glu Tyr Val Glu Tyr Tyr Gly Gly Ala Gly Val Gln His Ile Ala
385                 390                 395                 400

Leu Lys Val Asn Asp Ile Ile Ser Val Ile Ser Thr Leu Arg Ala Arg
                405                 410                 415

Gly Val Glu Phe Leu Glu Val Pro Pro Lys Tyr Tyr Asp Ser Leu Arg
                420                 425                 430

Lys Arg Leu Ala His Ser Ala Val Gln Ile Glu Glu Asp Leu Lys Arg
            435                 440                 445

Ile Glu Asp Leu His Ile Leu Val Asp Phe Asp Asp Arg Gly Tyr Leu
        450                 455                 460

Leu Gln Ile Phe Thr Lys Pro Val Glu Asp Arg Pro Thr Leu Phe Tyr
465                 470                 475                 480

Glu Ile Ile Gln Arg His Asn Asn Gly Phe Gly Ile Gly Asn Phe
                485                 490                 495

Lys Ala Leu Phe Glu Ser Leu Glu Gln Glu Gln Glu Arg Arg Gly Asn
            500                 505                 510

Leu Ile

<210> SEQ ID NO 8
<211> LENGTH: 1422
<212> TYPE: DNA
<213> ORGANISM: Arabidopsis thaliana

<400> SEQUENCE: 8
atgtgtctat cgttagcttc tacagctcaa cgaaacacac agttccgtag cagagtttta      60
gttttagcag agttggtgaa atcaatgggc caccaaaacg ccgccgtttc agagaatcaa     120
aaccatgatg acggcgctgc gtcgtcgccg ggattcaagc tcgtcggatt ttccaagttc     180
gtaagaaaga atccaaagtc tgataaattc aaggttaagc gcttccatca catcgagttc     240
tggtgcggcg acgcaaccaa cgtcgctcgt cgcttctcct ggggtctggg gatgagattc     300
tccgccaaat ccgatctttc caccggaaac atggttcacg cctcttacct actcacctcc     360
ggtgacctcc gattcctttt cactgctcct tactctccgt ctctctccgc cggagagatt     420
aaaccgacaa ccacagcttc tatcccaagt ttcgatcacg gctcttgtcg ttccttcttc     480
tcttcacatg gtctcggtgt tagagccgtt gcgattgaag tagaagacgc agagtcagct     540
ttctccatca gtgtagctaa tggcgctatt ccttcgtcgc ctcctatcgt cctcaatgaa     600
gcagttacga tcgctgaggt taaactatac ggcgatgttg ttctccgata tgttagttac     660
aaagcagaag ataccgaaaa atccgaattc ttgccagggt tcgagcgtgt agaggatgcg     720
tcgtcgttcc cattggatta tggtatccgg cggcttgacc acgccgtggg aaacgttcct     780
gagcttggtc cggctttaac ttatgtagcg gggttcactg gttttcacca attcgcagag     840
ttcacagcag acgacgttgg aaccgccgag agcggtttaa attcagcggt cctggctagc     900
aatgatgaaa tggttcttct accgattaac gagccagtgc acggaacaaa gaggaagagt     960
```

```
cagattcaga cgtatttgga acataacgaa ggcgcagggc tacaacatct ggctctgatg    1020
agtgaagaca tattcaggac cctgagagag atgaggaaga ggagcagtat tggaggattc    1080
gacttcatgc cttctcctcc gcctacttac taccagaatc tcaagaaacg ggtcggcgac    1140
gtgctcagcg atgatcagat caaggagtgt gaggaattag ggattcttgt agacagagat    1200
gatcaaggga cgttgcttca aatcttcaca aaaccactag gtgacaggcc gacgatattt    1260
atagagataa tccagagagt aggatgcatg atgaaagatg aggaagggaa ggcttaccag    1320
agtggaggat gtggtggttt tggcaaaggc aatttctctg agctcttcaa gtccattgaa    1380
gaatacgaaa agactcttga agccaaacag ttagtgggat ga                       1422
```

<210> SEQ ID NO 9
<211> LENGTH: 445
<212> TYPE: PRT
<213> ORGANISM: Arabidopsis thaliana

<400> SEQUENCE: 9

```
Met Gly His Gln Asn Ala Ala Val Ser Glu Asn Gln Asn His Asp Asp
1               5                   10                  15

Gly Ala Ala Ser Ser Pro Gly Phe Lys Leu Val Gly Phe Ser Lys Phe
            20                  25                  30

Val Arg Lys Asn Pro Lys Ser Asp Lys Phe Lys Val Lys Arg Phe His
        35                  40                  45

His Ile Glu Phe Trp Cys Gly Asp Ala Thr Asn Val Ala Arg Arg Phe
    50                  55                  60

Ser Trp Gly Leu Gly Met Arg Phe Ser Ala Lys Ser Asp Leu Ser Thr
65                  70                  75                  80

Gly Asn Met Val His Ala Ser Tyr Leu Leu Thr Ser Gly Asp Leu Arg
                85                  90                  95

Phe Leu Phe Thr Ala Pro Tyr Ser Pro Ser Leu Ser Ala Gly Glu Ile
            100                 105                 110

Lys Pro Thr Thr Thr Ala Ser Ile Pro Ser Phe Asp His Gly Ser Cys
        115                 120                 125

Arg Ser Phe Phe Ser Ser His Gly Leu Gly Val Arg Ala Val Ala Ile
    130                 135                 140

Glu Val Glu Asp Ala Glu Ser Ala Phe Ser Ile Ser Val Ala Asn Gly
145                 150                 155                 160

Ala Ile Pro Ser Ser Pro Ile Val Leu Asn Glu Ala Val Thr Ile
            165                 170                 175

Ala Glu Val Lys Leu Tyr Gly Asp Val Val Leu Arg Tyr Val Ser Tyr
        180                 185                 190

Lys Ala Glu Asp Thr Glu Lys Ser Glu Phe Leu Pro Gly Phe Glu Arg
    195                 200                 205

Val Glu Asp Ala Ser Ser Phe Pro Leu Asp Tyr Gly Ile Arg Arg Leu
210                 215                 220

Asp His Ala Val Gly Asn Val Pro Glu Leu Gly Pro Ala Leu Thr Tyr
225                 230                 235                 240

Val Ala Gly Phe Thr Gly Phe His Gln Phe Ala Glu Phe Thr Ala Asp
            245                 250                 255

Asp Val Gly Thr Ala Glu Ser Gly Leu Asn Ser Ala Val Leu Ala Ser
        260                 265                 270

Asn Asp Glu Met Val Leu Leu Pro Ile Asn Glu Pro Val His Gly Thr
    275                 280                 285

Lys Arg Lys Ser Gln Ile Gln Thr Tyr Leu Glu His Asn Glu Gly Ala
```

```
                290                 295                 300
Gly Leu Gln His Leu Ala Leu Met Ser Glu Asp Ile Phe Arg Thr Leu
305                 310                 315                 320

Arg Glu Met Arg Lys Arg Ser Ser Ile Gly Gly Phe Asp Phe Met Pro
                325                 330                 335

Ser Pro Pro Thr Tyr Tyr Gln Asn Leu Lys Lys Arg Val Gly Asp
                340                 345                 350

Val Leu Ser Asp Asp Gln Ile Lys Glu Cys Glu Glu Leu Gly Ile Leu
                355                 360                 365

Val Asp Arg Asp Asp Gln Gly Thr Leu Leu Gln Ile Phe Thr Lys Pro
                370                 375                 380

Leu Gly Asp Arg Pro Thr Ile Phe Ile Glu Ile Ile Gln Arg Val Gly
385                 390                 395                 400

Cys Met Met Lys Asp Glu Glu Gly Lys Ala Tyr Gln Ser Gly Gly Cys
                405                 410                 415

Gly Gly Phe Gly Lys Gly Asn Phe Ser Glu Leu Phe Lys Ser Ile Glu
                420                 425                 430

Glu Tyr Glu Lys Thr Leu Glu Ala Lys Gln Leu Val Gly
                435                 440                 445

<210> SEQ ID NO 10
<211> LENGTH: 450
<212> TYPE: PRT
<213> ORGANISM: Artificial sequence
<220> FEATURE:
<223> OTHER INFORMATION: Protein encoded by SEQ ID No. 8 plus an
      additional alanine directly downstream of the initial amino acid
      methionine followed by 6 histidine amino acids
<220> FEATURE:
<221> NAME/KEY: MISC_FEATURE
<222> LOCATION: (2)..(2)
<223> OTHER INFORMATION: Ala
<220> FEATURE:
<221> NAME/KEY: MISC_FEATURE
<222> LOCATION: (3)..(8)
<223> OTHER INFORMATION: His Tag made of 6 His

<400> SEQUENCE: 10

Met Ala His His His His His His Gln Asn Ala Ala Val Ser Glu Asn
1               5                   10                  15

Gln Asn His Asp Asp Gly Ala Ala Ser Ser Pro Gly Phe Lys Leu Val
                20                  25                  30

Gly Phe Ser Lys Phe Val Arg Lys Asn Pro Lys Ser Asp Lys Phe Lys
                35                  40                  45

Val Lys Arg Phe His His Ile Glu Phe Trp Cys Gly Asp Ala Thr Asn
50                  55                  60

Val Ala Arg Arg Phe Ser Trp Gly Leu Gly Met Arg Phe Ser Ala Lys
65                  70                  75                  80

Ser Asp Leu Ser Thr Gly Asn Met Val His Ala Ser Tyr Leu Leu Thr
                85                  90                  95

Ser Gly Asp Leu Arg Phe Leu Phe Thr Ala Pro Tyr Ser Pro Ser Leu
                100                 105                 110

Ser Ala Gly Glu Ile Lys Pro Thr Thr Thr Ala Ser Ile Pro Ser Phe
                115                 120                 125

Asp His Gly Ser Cys Arg Ser Phe Phe Ser Ser His Gly Leu Gly Val
                130                 135                 140

Arg Ala Val Ala Ile Glu Val Glu Asp Ala Glu Ser Ala Phe Ser Ile
145                 150                 155                 160
```

```
Ser Val Ala Asn Gly Ala Ile Pro Ser Ser Pro Pro Ile Val Leu Asn
            165                 170                 175

Glu Ala Val Thr Ile Ala Glu Val Lys Leu Tyr Gly Asp Val Val Leu
        180                 185                 190

Arg Tyr Val Ser Tyr Lys Ala Glu Asp Thr Glu Lys Ser Glu Phe Leu
            195                 200                 205

Pro Gly Phe Glu Arg Val Glu Asp Ala Ser Ser Phe Pro Leu Asp Tyr
        210                 215                 220

Gly Ile Arg Arg Leu Asp His Ala Val Gly Asn Val Pro Glu Leu Gly
225                 230                 235                 240

Pro Ala Leu Thr Tyr Val Ala Gly Phe Thr Gly Phe His Gln Phe Ala
            245                 250                 255

Glu Phe Thr Ala Asp Asp Val Gly Thr Ala Glu Ser Gly Leu Asn Ser
            260                 265                 270

Ala Val Leu Ala Ser Asn Asp Glu Met Val Leu Leu Pro Ile Asn Glu
            275                 280                 285

Pro Val His Gly Thr Lys Arg Lys Ser Gln Ile Gln Thr Tyr Leu Glu
        290                 295                 300

His Asn Glu Gly Ala Gly Leu Gln His Leu Ala Leu Met Ser Glu Asp
305                 310                 315                 320

Ile Phe Arg Thr Leu Arg Glu Met Arg Lys Arg Ser Ile Gly Gly
                325                 330                 335

Phe Asp Phe Met Pro Ser Pro Pro Thr Tyr Tyr Gln Asn Leu Lys
            340                 345                 350

Lys Arg Val Gly Asp Val Leu Ser Asp Gln Ile Lys Glu Cys Glu
            355                 360                 365

Glu Leu Gly Ile Leu Val Asp Arg Asp Gln Gly Thr Leu Leu Gln
        370                 375                 380

Ile Phe Thr Lys Pro Leu Gly Asp Arg Pro Thr Ile Phe Ile Glu Ile
385                 390                 395                 400

Ile Gln Arg Val Gly Cys Met Met Lys Asp Glu Glu Lys Ala Tyr
            405                 410                 415

Gln Ser Gly Gly Cys Gly Gly Phe Gly Lys Gly Asn Phe Ser Glu Leu
            420                 425                 430

Phe Lys Ser Ile Glu Glu Tyr Glu Lys Thr Leu Glu Ala Lys Gln Leu
        435                 440                 445

Val Gly
    450

<210> SEQ ID NO 11
<211> LENGTH: 568
<212> TYPE: PRT
<213> ORGANISM: Artificial sequence
<220> FEATURE:
<223> OTHER INFORMATION: Protein of SEQ ID No. 9 plus the Optimized
      Transit Peptide sequence located at the N-terminal extremity of
      the protein.
<220> FEATURE:
<221> NAME/KEY: TRANSIT
<222> LOCATION: (1)..(125)
<223> OTHER INFORMATION: Optimized transit peptide to chloroplasts

<400> SEQUENCE: 11

Met Ala Ser Ile Ser Ser Ser Val Ala Thr Val Ser Arg Thr Ala Pro
1               5                   10                  15

Ala Gln Ala Asn Met Val Ala Pro Phe Thr Gly Leu Lys Ser Asn Ala
            20                  25                  30
```

```
Ala Phe Pro Thr Thr Lys Lys Ala Asn Asp Phe Ser Thr Leu Pro Ser
            35                  40                  45

Asn Gly Gly Arg Val Gln Cys Met Gln Val Trp Pro Ala Tyr Gly Asn
 50                  55                  60

Lys Lys Phe Glu Thr Leu Ser Tyr Leu Pro Pro Leu Ser Met Ala Pro
 65                  70                  75                  80

Thr Val Met Met Ala Ser Ser Ala Thr Ala Val Ala Pro Phe Gln Gly
                 85                  90                  95

Leu Lys Ser Thr Ala Ser Leu Pro Val Ala Arg Arg Ser Ser Arg Ser
                100                 105                 110

Leu Gly Asn Val Ser Asn Gly Gly Arg Ile Arg Cys Ala Met Gln Asn
                115                 120                 125

Ala Ala Val Ser Glu Asn Gln Asn His Asp Asp Gly Ala Ala Ser Ser
            130                 135                 140

Pro Gly Phe Lys Leu Val Gly Phe Ser Lys Phe Val Arg Lys Asn Pro
145                 150                 155                 160

Lys Ser Asp Lys Phe Lys Val Lys Arg Phe His His Ile Glu Phe Trp
                165                 170                 175

Cys Gly Asp Ala Thr Asn Val Ala Arg Arg Phe Ser Trp Gly Leu Gly
                180                 185                 190

Met Arg Phe Ser Ala Lys Ser Asp Leu Ser Thr Gly Asn Met Val His
            195                 200                 205

Ala Ser Tyr Leu Leu Thr Ser Gly Asp Leu Arg Phe Leu Phe Thr Ala
            210                 215                 220

Pro Tyr Ser Pro Ser Leu Ser Ala Gly Glu Ile Lys Pro Thr Thr Thr
225                 230                 235                 240

Ala Ser Ile Pro Ser Phe Asp His Gly Ser Cys Arg Ser Phe Phe Ser
                245                 250                 255

Ser His Gly Leu Gly Val Arg Ala Val Ala Ile Glu Val Glu Asp Ala
                260                 265                 270

Glu Ser Ala Phe Ser Ile Ser Val Ala Asn Gly Ala Ile Pro Ser Ser
            275                 280                 285

Pro Pro Ile Val Leu Asn Glu Ala Val Thr Ile Ala Glu Val Lys Leu
290                 295                 300

Tyr Gly Asp Val Val Leu Arg Tyr Val Ser Tyr Lys Ala Glu Asp Thr
305                 310                 315                 320

Glu Lys Ser Glu Phe Leu Pro Gly Phe Glu Arg Val Glu Asp Ala Ser
                325                 330                 335

Ser Phe Pro Leu Asp Tyr Gly Ile Arg Arg Leu Asp His Ala Val Gly
                340                 345                 350

Asn Val Pro Glu Leu Gly Pro Ala Leu Thr Tyr Val Ala Gly Phe Thr
                355                 360                 365

Gly Phe His Gln Phe Ala Glu Phe Thr Ala Asp Asp Val Gly Thr Ala
            370                 375                 380

Glu Ser Gly Leu Asn Ser Ala Val Leu Ala Ser Asn Asp Glu Met Val
385                 390                 395                 400

Leu Leu Pro Ile Asn Glu Pro Val His Gly Thr Lys Arg Lys Ser Gln
                405                 410                 415

Ile Gln Thr Tyr Leu Glu His Asn Glu Gly Ala Gly Leu Gln His Leu
                420                 425                 430

Ala Leu Met Ser Glu Asp Ile Phe Arg Thr Leu Arg Glu Met Arg Lys
            435                 440                 445

Arg Ser Ser Ile Gly Gly Phe Asp Phe Met Pro Ser Pro Pro Pro Thr
```

```
                450                 455                 460
Tyr Tyr Gln Asn Leu Lys Lys Arg Val Gly Asp Val Leu Ser Asp Asp
465                 470                 475                 480

Gln Ile Lys Glu Cys Glu Leu Gly Ile Leu Val Asp Arg Asp Asp
                485                 490                 495

Gln Gly Thr Leu Leu Gln Ile Phe Thr Lys Pro Leu Gly Asp Arg Pro
                500                 505                 510

Thr Ile Phe Ile Glu Ile Ile Gln Arg Val Gly Cys Met Met Lys Asp
                515                 520                 525

Glu Glu Gly Lys Ala Tyr Gln Ser Gly Gly Cys Gly Gly Phe Gly Lys
                530                 535                 540

Gly Asn Phe Ser Glu Leu Phe Lys Ser Ile Glu Glu Tyr Glu Lys Thr
545                 550                 555                 560

Leu Glu Ala Lys Gln Leu Val Gly
                565

<210> SEQ ID NO 12
<211> LENGTH: 575
<212> TYPE: PRT
<213> ORGANISM: Artificial sequence
<220> FEATURE:
<223> OTHER INFORMATION: Protein of SEQ ID No. 10 plus the Optimized
      Transit Peptide sequence directly located at the N-terminal
      extremity of the protein.
<220> FEATURE:
<221> NAME/KEY: TRANSIT
<222> LOCATION: (1)..(125)
<223> OTHER INFORMATION: Optimized transit peptide to chloroplasts
<220> FEATURE:
<221> NAME/KEY: MISC_FEATURE
<222> LOCATION: (126)..(126)
<223> OTHER INFORMATION: Met
<220> FEATURE:
<221> NAME/KEY: MISC_FEATURE
<222> LOCATION: (127)..(127)
<223> OTHER INFORMATION: Ala
<220> FEATURE:
<221> NAME/KEY: MISC_FEATURE
<222> LOCATION: (128)..(133)
<223> OTHER INFORMATION: His Tag made of 6 His

<400> SEQUENCE: 12

Met Ala Ser Ile Ser Ser Val Ala Thr Val Ser Arg Thr Ala Pro
1               5                   10                  15

Ala Gln Ala Asn Met Val Ala Pro Phe Thr Gly Leu Lys Ser Asn Ala
                20                  25                  30

Ala Phe Pro Thr Thr Lys Lys Ala Asn Asp Phe Ser Thr Leu Pro Ser
                35                  40                  45

Asn Gly Gly Arg Val Gln Cys Met Gln Val Trp Pro Ala Tyr Gly Asn
                50                  55                  60

Lys Lys Phe Glu Thr Leu Ser Tyr Leu Pro Pro Leu Ser Met Ala Pro
65                  70                  75                  80

Thr Val Met Met Ala Ser Ser Ala Thr Ala Val Ala Pro Phe Gln Gly
                85                  90                  95

Leu Lys Ser Thr Ala Ser Leu Pro Val Ala Arg Arg Ser Ser Arg Ser
                100                 105                 110

Leu Gly Asn Val Ser Asn Gly Gly Arg Ile Arg Cys Ala Met Ala His
                115                 120                 125

His His His His His Gln Asn Ala Ala Val Ser Glu Asn Gln Asn His
                130                 135                 140

Asp Asp Gly Ala Ala Ser Ser Pro Gly Phe Lys Leu Val Gly Phe Ser
```

```
                    145                 150                 155                 160
                Lys Phe Val Arg Lys Asn Pro Lys Ser Asp Lys Phe Lys Val Lys Arg
                                165                 170                 175
                Phe His His Ile Glu Phe Trp Cys Gly Asp Ala Thr Asn Val Ala Arg
                                180                 185                 190
                Arg Phe Ser Trp Gly Leu Gly Met Arg Phe Ser Ala Lys Ser Asp Leu
                                195                 200                 205
                Ser Thr Gly Asn Met Val His Ala Ser Tyr Leu Leu Thr Ser Gly Asp
                    210                 215                 220
                Leu Arg Phe Leu Phe Thr Ala Pro Tyr Ser Pro Ser Leu Ser Ala Gly
                225                 230                 235                 240
                Glu Ile Lys Pro Thr Thr Ala Ser Ile Pro Ser Phe Asp His Gly
                                245                 250                 255
                Ser Cys Arg Ser Phe Phe Ser Ser His Gly Leu Gly Val Arg Ala Val
                                260                 265                 270
                Ala Ile Glu Val Glu Asp Ala Glu Ser Ala Phe Ser Ile Ser Val Ala
                                275                 280                 285
                Asn Gly Ala Ile Pro Ser Ser Pro Ile Val Leu Asn Glu Ala Val
                    290                 295                 300
                Thr Ile Ala Glu Val Lys Leu Tyr Gly Asp Val Val Leu Arg Tyr Val
                305                 310                 315                 320
                Ser Tyr Lys Ala Glu Asp Thr Glu Lys Ser Glu Phe Leu Pro Gly Phe
                                325                 330                 335
                Glu Arg Val Glu Asp Ala Ser Ser Phe Pro Leu Asp Tyr Gly Ile Arg
                                340                 345                 350
                Arg Leu Asp His Ala Val Gly Asn Val Pro Glu Leu Gly Pro Ala Leu
                                355                 360                 365
                Thr Tyr Val Ala Gly Phe Thr Gly Phe His Gln Phe Ala Glu Phe Thr
                                370                 375                 380
                Ala Asp Asp Val Gly Thr Ala Glu Ser Gly Leu Asn Ser Ala Val Leu
                385                 390                 395                 400
                Ala Ser Asn Asp Glu Met Val Leu Leu Pro Ile Asn Glu Pro Val His
                                405                 410                 415
                Gly Thr Lys Arg Lys Ser Gln Ile Gln Thr Tyr Leu Glu His Asn Glu
                                420                 425                 430
                Gly Ala Gly Leu Gln His Leu Ala Leu Met Ser Glu Asp Ile Phe Arg
                                435                 440                 445
                Thr Leu Arg Glu Met Arg Lys Arg Ser Ser Ile Gly Gly Phe Asp Phe
                    450                 455                 460
                Met Pro Ser Pro Pro Thr Tyr Tyr Gln Asn Leu Lys Lys Arg Val
                465                 470                 475                 480
                Gly Asp Val Leu Ser Asp Gln Ile Lys Glu Cys Glu Glu Leu Gly
                                485                 490                 495
                Ile Leu Val Asp Arg Asp Asp Gln Gly Thr Leu Leu Gln Ile Phe Thr
                                500                 505                 510
                Lys Pro Leu Gly Asp Arg Pro Thr Ile Phe Ile Glu Ile Ile Gln Arg
                                515                 520                 525
                Val Gly Cys Met Met Lys Asp Glu Glu Gly Lys Ala Tyr Gln Ser Gly
                                530                 535                 540
                Gly Cys Gly Gly Phe Gly Lys Gly Asn Phe Ser Glu Leu Phe Lys Ser
                545                 550                 555                 560
                Ile Glu Glu Tyr Glu Lys Thr Leu Glu Ala Lys Gln Leu Val Gly
                                565                 570                 575
```

<210> SEQ ID NO 13
<211> LENGTH: 26
<212> TYPE: DNA
<213> ORGANISM: Artificial sequence
<220> FEATURE:
<223> OTHER INFORMATION: Primer XhoI-OTP-for

<400> SEQUENCE: 13
ctcgagatgg cttcgatctc ctcctc                                        26

<210> SEQ ID NO 14
<211> LENGTH: 26
<212> TYPE: DNA
<213> ORGANISM: Artificial sequence
<220> FEATURE:
<223> OTHER INFORMATION: Primer NcoI-OTP-rev

<400> SEQUENCE: 14
cccatggcgc accggattct tccgcc                                        26

<210> SEQ ID NO 15
<211> LENGTH: 1152
<212> TYPE: DNA
<213> ORGANISM: Artificial sequence
<220> FEATURE:
<223> OTHER INFORMATION: Nucleic acid sequence encoding Blepharisma
      japonicum HPPD optimized for dicotyledoneous plants

<400> SEQUENCE: 15
atggctactt actacgataa gcaagagact agaccagatc ttggagagtt ctacggattc      60
caccatgtta ggttctacgt gtctaattct gagcaagctg cttctttcta cacttcccgt     120
ttcggatttt ctccagttgc ttacgaagga cttgagactg aaatcagaa gttctgcact      180 aacgttgtta ggtctaacca cgtggtgatt gcttttactt ctgctctcac tccagaggat     240
aatgaggtta acaggcatgt tggaaagcac tctgatggtg ttcaggatat tgctttctct     300
gtgtctgatg ctagaggaat gtacgagaag gctattgcta agggatgcaa gtctttcaga     360
gagccacaag ttcttcaaga tcagttcgga tcagtgatta ttgcttccct tcagacttac     420
ggtgatactg ttcacactct cgttcagaac gttgattaca ctggaccatt ccttccaggt     480
ttcagggcta tcactaagga tgatccactt aactctgctt ccccacaggt gaactacgat     540
atcattgatc acgttgtggg aaaatcagcca ggtggagata tgactccaac tgttgagtgg     600
tacgagaagt accttgagtt tcacaggtat tggagtgctg atgagtctgt gatccacact     660
gattactctg ctcttagatc tgttgttgtg gctgattggg atgaggttat caagatgcct     720
attaacgaac cagctgatgg acttaggaag tcccagattc aagagtacgt tgagtattat     780
ggtggagctg gtgttcaaca cattgctctc aaggtgaacg atatcattc cgtgatttcc      840 actcttagag ctagaggagt tgagtttctt gaagtcccac caagtacta cgattctctc      900 agaaagaggc ttgctcattc tgctgttcag atcgaagagg atcttaaacg tattgaggac     960
cttcacatcc tcgtggattt tgatgatagg ggatacctc tccagatttt cactaagcca     1020
gttgaggata ggccaacttt gttctacgag atcatccaaa ggcataacaa caacggattc     1080
ggaatcggaa atttcaaggc tcttttcgag tctcttgagc aagaacaaga gagaagggga     1140
aacctcatct ga                                                       1152

<210> SEQ ID NO 16
<211> LENGTH: 1152

<212> TYPE: DNA
<213> ORGANISM: Artificial sequence
<220> FEATURE:
<223> OTHER INFORMATION: Nucleic acid sequence encoding Blepharisma
      japonicum HPPD optimized for Zea mays plants

<400> SEQUENCE: 16

```
atggccacct actacgacaa gcaggagact agaccggacc tgggcgagtt ctacgggttc      60
catcacgtgc gcttctacgt gagcaacagc gagcaggctg ccagcttcta caccagccgc    120
ttcggcttca gcccggtggc ctacgagggc cttgagactg caaccagaa gttctgcacc     180
aacgtcgtgc gcagcaacca tgtggtgatc gccttcacca cgccctgac ccccgaggac     240
aacgaggtga accgccacgt gggcaagcac agcgacggcg tgcaggatat cgccttcagc    300
gtgagcgacg ccaggggcat gtacgagaag gctatcgcca agggctgcaa gagcttccgc    360
gagcctcagg tgctgcagga ccagttcggc agcgtgatca tcgccagcct gcagacctac    420
ggcgacactg tgcacaccct ggtgcagaac gtggactaca ccggcccgtt cctcccgggc    480
ttccgcgcca tcaccaagga cgaccgctg aacagcgcct ccccccaggt gaactacgac     540
atcatcgacc acgtggtggg caaccagcca ggcggcgaca tgaccccaac cgtcgagtgg    600
tacgagaagt accttgagtt ccaccgctac tggtccgccg acgagagcgt gatccacacc    660
gactacagcg ccctgcgcag cgtggtggtg gccgactggg acgaggtgat caagatgccg    720
atcaacgagc cggctgacgg cctgcgcaag agccagatcc aggagtacgt tgagtactac    780
ggggcgctg gcgtccagca tatcgccctg aaggtgaacg acatcatcag cgtgatcagc    840
actctgcgcg ccaggggcgt cgagttcctt gaggtgccgc gaagtacta cgacagcctc    900
cgcaagcgcc tggcccacag cgccgtgcag atcgaggagg acctgaagcg catcgaggac    960
ctgcacatcc tggtggactt cgacgaccgc ggctacctgc tgcagatctt caccaagccg   1020
gtcgaggacc gcccgaccct gttctacgag atcatccagc gccacaacaa caacggcttc   1080
ggcatcggca acttcaaggc cctgttcgag agccttgagc aggagcagga gaggcgcggc   1140
aacctgatct ga                                                       1152
```

<210> SEQ ID NO 17
<211> LENGTH: 1152
<212> TYPE: DNA
<213> ORGANISM: Artificial sequence
<220> FEATURE:
<223> OTHER INFORMATION: Nucleic acid sequence encoding Blepharisma
      japonicum HPPD optimized for Brassica napus plants

<400> SEQUENCE: 17

```
atggcaacct attacgataa gcaagaaact cggccagact tgggagagtt ctacggtttc      60
catcatgtca gattttatgt ttccaatagc gaacaggccg cttcatttta cacttctagg    120
ttcggcttta gccctgtagc gtacgaaggc cttgaaactg gtaaccagaa gttttgtact    180
aacgttgtgc gttcaaacca tgtggtgatt gcgtttacta cgccttgac gcctgaagat     240
aatgaggtta accgtcatgt gggtaagcac tctgacggtg tccaagatat cgctttcagc    300
gttagcgatg cgcgtggaat gtatgaaaag gctattgcta agggttgtaa gtcgtttcgt    360
gaaccacagg tacttcagga ccagttcgga tctgttatca tcgctagtct ccagacttac    420
ggcgatacag ttcatactct tgtccaaaac gttgattata ccggaccatt cttaccaggc    480
ttcagggcta tcaccaagga cgaccgtttg aactccgcct ttcctcaagt gaattatgat    540
ataattgatc atgtcgtggg gaaccagccg ggtggagata tgactcccac tgttgagtgg    600
```

| | |
|---|---|
| tatgagaagt acctcgaatt tcacagatac tggagtgccg atgagagtgt gattcatact | 660 |
| gattactccg cgcttagatc ggttgtcgtc gcggattggg atgaggtcat caaaatgccc | 720 |
| attaacgaac cggctgatgg ccttcgaaaa tcgcaaatac aggagtacgt ggaatactat | 780 |
| gggggtgctg gtgtccagca catcgccttg aaagttaacg acataatttc tgttatttct | 840 |
| accctgcgtg ctagaggggt ggagttcctg gaagtgcctc cgaagtatta cgacagctta | 900 |
| agaaaaagac tagctcacag cgccgtgcag atcgaggaag accttaaaag gattgaagac | 960 |
| cttcatatcc tcgttgactt cgatgatagg ggatacttat tgcagatatt taccaagccg | 1020 |
| gttgaggata ggcctacact tttctatgag attattcagc gccataacaa caacggtttc | 1080 |
| ggtattggaa atttcaaagc tctctttgag agtcttgaac aggagcagga gcgtagggga | 1140 |
| aacctcatct ga | 1152 |

<210> SEQ ID NO 18
<211> LENGTH: 1152
<212> TYPE: DNA
<213> ORGANISM: Artificial sequence
<220> FEATURE:
<223> OTHER INFORMATION: Nucleic acid sequence encoding Blepharisma
   japonicum HPPD optimized for Beta vulgaris plants

<400> SEQUENCE: 18

| | |
|---|---|
| atggcaacat actacgataa gcaggaaacc cgacccgact tgggtgagtt ttacggattc | 60 |
| catcatgtgc gttcctacgt gtccaatagc gaacaagccg cttccttcta tacgagtaga | 120 |
| tttggttttt caccggtagc ctacgagggt ctggagactg gtaatcaaaa gttttgcaca | 180 |
| aatgtagtac gttcgaatca tgtggttatc gcatttactt cagcccttac accagaagac | 240 |
| aatgaagtca acaggcacgt ggggaagcat agcgacggtg ttcaagatat cgcatttagc | 300 |
| gtctcggacg cgaggggtat gtatgagaag gcaatcgcga aggggtgtaa gagttttaga | 360 |
| gaaccgcaag tgcttcaaga tcaattcggt tctgttatta tcgcctcttt acagacctac | 420 |
| ggggatactg ttcatacgct tgtccagaat gtcgattaca caggaccatt tcttcctggt | 480 |
| tttagggcta ttactaaaga tgacccattg aattctgctt cccgcaggt taattatgac | 540 |
| attatcgatc acgtcgttgg taatcagcct ggaggggata tgcacccac tgtcgagtgg | 600 |
| tatgagaagt atttggaatt tcaccggtat tggagtgctg acgagtcagt aatacatacc | 660 |
| gattattcag cactccgaag cgttgtagtc gctgactggg atgaggtaat taaaatgcca | 720 |
| atcaacgagc cagcagacgg tttgagaaag agtcagatac aggagtatgt tgaatactac | 780 |
| ggggtgcag gagtacaaca cattgcgctc aaggtgaacg atattatcag cgttattagc | 840 |
| actcttaggg ctaggggagt cgagtttctt gaagtaccgc caaaatatta tgatagcttg | 900 |
| agaaaaagat tagctcattc agctgttcaa attgaagaag acctcaaaag gattgaggac | 960 |
| ctacatattt tagtggactt tgatgataga ggttatttgc tccagatctt cacaaaacca | 1020 |
| gttgaggata gacctactct tttttatgag atcatacaac gacataataa taacggtttc | 1080 |
| ggaattggaa acttcaaggc tctttttcgaa tccttggaac aagaacaaga acggcgaggt | 1140 |
| aaccttatct ga | 1152 |

<210> SEQ ID NO 19
<211> LENGTH: 1152
<212> TYPE: DNA
<213> ORGANISM: Artificial sequence
<220> FEATURE:
<223> OTHER INFORMATION: Nucleic acid sequence encoding Blepharisma
   japonicum HPPD optimized for Gossypium hirsutum plants

<400> SEQUENCE: 19

```
atggccacct attatgacaa gcaagaaacc agaccagatc taggggaatt ctacggtttc      60
catcatgttc gattctatgt tagcaactct gagcaagctg caagtttcta cacatcaagg     120
tttggatttt cgccagtggc atatgaaggc ctggagactg gaaatcaaaa gttttgtaca     180
aatgtggttc gttctaatca tgtcgtgatc gcttttactt cagctctgac accggaggac     240
aacgaagtga acaggcacgt tggaaagcat agtgatggtg tgcaggacat agcttttct      300
gtttcggatg cgcgaggtat gtacgaaaag gccatcgcca agggatgtaa atccttcagg     360
gaaccacagg tgttgcaaga tcaatttgga agtgtgataa ttgcatcgtt gcaaacttac     420
ggggacacag tccacacttt ggtccaaaat gtggattaca ctggacccct tcttccaggg     480
tttcgagcaa taactaagga tgaccctctg aattcagctt ccccacaggt caattatgat     540
ataattgatc acgttgttgg caaccaacca ggaggcgaca tgactcctac tgtggaatgg     600
tatgagaaat acttggaatt tcacagatac tggtccgccg atgaaagcgt gatccatacc     660
gattactctg cgctgagatc ggtggtggtc gctgactggg acgaggttat taaaatgcct     720
attaatgaac ctgcggatgg tcttaggaag tctcaaatcc aagaatacgt agagtactat     780
ggaggggccg gggtccaaca cattgccttg aaggtgaatg atatcataag cgtaatttcc     840
actctaaggg cacgaggagt ggagttcttg gaggttcctc cgaagtacta cgattctctt     900
agaaagaggc ttgcccattc tgccgtccag atagaggagg atcttaaaag gattgaagac     960
ctacatattc ttgttgattt tgacgatagg ggttacttgt tgcaaatttt cacaaagcct    1020
gttgaggaca gacctactct gttctacgaa atcatccaga gacataataa taatggtttt    1080
ggtattggaa atttcaaagc attgtttgaa tctcttgaac aggaacaaga aaggagggc     1140
aacttgattt ga                                                         1152
```

<210> SEQ ID NO 20
<211> LENGTH: 1152
<212> TYPE: DNA
<213> ORGANISM: Artificial sequence
<220> FEATURE:
<223> OTHER INFORMATION: Nucleic acid sequence encoding Blepharisma
japonicum HPPD optimized for Glycine max plants

<400> SEQUENCE: 20

```
atggccacat actatgataa acaggaaacc cgcccagacc taggagaatt ttatggtttt      60
catcatgttc gattttatgt ttccaactca gagcaagctg cttcctttta cacttcgagg     120
tttggattct caccccgttgc ctatgaaggt ctcgaaaccg gtaatcagaa attttgtacc     180
aatgtagtga atcgaacca cgttgtaatt gcttttacaa gtgctctcac gccagaagat     240
aatgaggtga acagacacgt gggcaagcac tcagatggag tgcaagatat tgccttttcc     300
gtttccgacg ctaggggggat gtacgagaag gccatcgcaa gggggtgtaa atcttttagg     360
gaaccgcagg tactccagga tcagtttggt tccgttatca tcgcctctct gcagacttat     420
ggtgacaccg tgcacacact tgttcaaaat gtggactaca cggggccgtt cctcccctgga    480
tttagagcta taacgaagga tgatcctctt aacagtgctt cccccaggt gaactacgat     540
attattgatc acgtagtagg aaaccagcca ggtggagata tgaccccac agtagagtgg     600
tatgagaagt atctggaatt tcaccggtat tggagtgccg acgagtcagt tatccataca     660
gattacagcg ccctcagatc cgtggtggta gctgactggg acgaggttat aaagatgcct     720
atcaatgagc ccgcagatgg attacgcaaa tctcaaattc aagagtatgt agagtattat     780
```

```
ggcggagccg gggttcaaca tattgctcta aaagtaaatg atataatcag tgtcatttca      840
acactccgtg ccagggtgt ggagtttctg gaggtgcccc caaagtacta cgatagcttg       900
aggaaaaggc ttgcacattc agccgtgcaa attgaagaag atttaaagcg gattgaagat      960
ttgcacatat tggtagattt tgacgataga ggatatcttc tccaaatttt cacaaaacca     1020
gtcgaggacc gcccaacact gttttacgag atcattcagc gccataacaa taacggtttt     1080
ggaattggga acttcaaggc gttgtttgag agccttgaac aggagcagga aagaagagga     1140
aacttaatct ga                                                         1152

<210> SEQ ID NO 21
<211> LENGTH: 1152
<212> TYPE: DNA
<213> ORGANISM: Artificial sequence
<220> FEATURE:
<223> OTHER INFORMATION: Nucleic acid sequence encoding Blepharisma
      japonicum HPPD optimized for Hordeum vulgare plants

<400> SEQUENCE: 21
atggccactt attacgacaa gcaggagaca cggccggact tgggagagtt ttacggattt       60
caccacgtaa ggttttacgt gtctaacagt gagcaagcag ccagcttcta cacctctcgg      120
ttcggctttt caccggtggc gtacgaggga cttgagaccg gtaaccagaa gttctgtacg      180
aatgtggtga ggagcaatca cgttgtgatt gcgtttacat ctgcccttac ccccgaggat      240
aatgaggtca atcgacacgt gggtaaacac tcggacggcg tgcaagatat cgcattctct      300
gtttctgatg cccgggggaat gtatgagaag gccatcgcca agggctgcaa gtccttccgc      360
gagccacagg tcctacaaga ccagttcggc tccgtcatta tcgcctcact tcagacctac      420
ggggacaccg tgcatacgct cgttcagaac gtggactaca ccgggccctt cctcccaggc      480
tttcgggcca tcacaaagga tgacccgcta aactccgcct tcccccaggt gaattatgac      540
attatcgatc acgttgtagg caatcagccc ggcggtgata tgaccccgac agtggagtgg      600
tacgagaagt atttggagtt tcatcgctat tggtcggcgg acgagtcagt gatacacacc      660
gactacagcg ccctcaggag cgtggtggtc gccgattggg atgaggtgat caagatgccg      720
atcaacgagc ccgcggatgg gctaaggaaa agccagatcc aagagtacgt cgagtattat      780
ggcggagccg gtgtccagca cattgcgctc aaggttaacg acataatctc ggtgatctcc      840
accctccgcg ccagggggcgt ggagttccta gaggtgccac ctaaatacta cgattctttg     900
cgcaagcggc tcgcgcattc cgctgtccag atcgaggaag atttaaagag gatagaggat     960
ctacatatac tggttgatt cgatgaccgc ggctacctcc tgcagatctt tacgaagcct     1020
gtcgaggatc gtcccacgct cttctacgag attatccaaa ggcataataa caacggtttt     1080
gggatcggca acttcaaggc tttgttcgaa tccctagagc aggagcagga gcgtagggga     1140
aacctgatct ga                                                         1152

<210> SEQ ID NO 22
<211> LENGTH: 1152
<212> TYPE: DNA
<213> ORGANISM: Artificial sequence
<220> FEATURE:
<223> OTHER INFORMATION: Nucleic acid sequence encoding Blepharisma
      japonicum HPPD optimized for Oryza sativa plants

<400> SEQUENCE: 22
atggccacct actacgacaa acaggagacc cgccccgatc ttggtgaatt ttatggtttc       60
```

```
catcatgtga ggttttacgt ctccaacagc gagcaagccg cgtcgtttta cacctcgcgg      120
tttggctttt ccccggtagc ttacgaaggg ctcgaaacag gtaaccagaa attctgtacg      180
aacgtcgtcc ggagcaatca tgttgtgata gcctttacgt ccgcgcttac gccagaggac      240
aacgaagtga accgccacgt cgggaagcac agcgatggtg tccaggatat tgcgttcagc      300
gtctcagatg cccgcgggat gtacgaaaag gccatcgcaa agggctgcaa gtcattccgc      360
gagccccagg tgttgcaaga ccagttcggg tccgtgatta tagcgtcact acagacgtac      420
ggggacaccg tacacactct cgtacagaat gttgactata ccgggccgtt cttaccaggc      480
tttagggcta taacgaagga cgaccctctg aactctgctt tcccacaggt caattacgac      540
ataatagacc acgtagtcgg caatcagcca ggcggagata tgaccccac agttgagtgg      600 tacgagaaat atcttgaatt ccatagatac tggagtgccg atgaatcggt cattcatact      660
gattactctg ccttgcggtc agtcgtggtg gccgactggg acgaggtcat taagatgccc      720
atcaacgaac ctgcgacgg attgcgaaag tctcaaatcc aggagtacgt ggaatattac      780
ggcggtgcag gggttcagca tattgctctt aaagtcaatg acattatctc agtgatctcg      840
acgcttcgcg cacgcggcgt agagttttg gaagtgccac caaatacta cgatagtctg      900 aggaagcgtc tcgcgcattc tgccgtccag atcgaggaag acctcaaaag gattgaggat      960
ctacacatat tggtggattt tgacgatagg gggtacctcc tgcagatttt cactaaacca     1020
gttgaagacc ggccgacttt gttctacgaa atcattcagc ggcataacaa caacgggttt     1080
ggtattggta actttaaggc tctctttgag agtcttgagc aggaacaaga gcgcagggga     1140
aacctcatct ga                                                         1152

<210> SEQ ID NO 23
<211> LENGTH: 1152
<212> TYPE: DNA
<213> ORGANISM: Artificial sequence
<220> FEATURE:
<223> OTHER INFORMATION: Nucleic acid sequence encoding Blepharisma
      japonicum HPPD optimized for Triticum aestivum plants

<400> SEQUENCE: 23
atggcgacgt actacgacaa acaagagacc agaccagacc ttggggagtt ctacggcttc       60
catcacgtta ggttttatgt ctcaaattct gagcaggccg cctctttcta tacatcgagg      120 ttcggttct caccggtcgc ctacgagggg ctggagaccg caaccagaa gttctgtacg      180 aacgttgtcc ggagtaacca cgtcgtgata gcatttacga gcgccttgac tccagaggac      240
aacgaggtta accgccacgt tggcaagcat tccgatggtg tacaggacat tgccttcagc      300
gtctctgacg ccaggggtat gtacgagaaa gcaatagcga agggatgtaa gagcttccgt      360
gagcctcagg ttttgcagga tcaattcgga tcggtcatca tcgcttcttt gcagacctac      420
ggggacaccg tccataccct cgtgcaaaac gtcgactata cgggcccgtt cctcccaggg      480
ttcagagcga ttaccaagga cgatcctctg aactcggcct tcccgcaagt caactacgac      540
atcattgatc atgtcgtcgg caatcaacca ggcggcgaca tgacgccgac tgtcgagtgg      600
tacgagaagt accttgagtt tcataggtat tggtccgcgg atgagagcgt catccacact      660
gactatagcg cccttaggtc tgttgtcgtt gccgactggg atgaggtcat caaaatgccg      720
atcaacgagc ccgctgacgg tctacgcaaa tctcagatcc aggaatacgt cgagtactac      780
ggtggagcag gggtgcaaca tattgcccta aaggtcaatg atataatctc cgttattagc      840
acactccgcg ccaggggagt ggaattctta gaggtacctc cgaaatacta cgactctttg      900
```

```
aggaagaggt tggctcatag tgccgtccaa atcgaggagg atctgaaaag aatcgaggac       960
ttgcatattc tcgttgactt tgacgatagg ggttatctac tccaaatctt tactaagccg      1020
gtcgaggaca gaccgaccct gttctacgag atcatccaac gtcacaacaa caacggcttc      1080
ggaattggca acttcaaggc cctgtttgaa tctctggaac aggagcagga gcgacggggg      1140
aatctaattt ga                                                          1152
```